United States Patent
Zarnitsyn et al.

(10) Patent No.: US 9,931,330 B2
(45) Date of Patent: *Apr. 3, 2018

(54) METHODS AND DEVICES FOR THE TREATMENT OF OCULAR DISEASES IN HUMAN SUBJECTS

(71) Applicant: CLEARSIDE BIOMEDICAL, INC., Alpharetta, GA (US)

(72) Inventors: Vladimir Zarnitsyn, Atlanta, GA (US); Samirkumar Patel, Atlanta, GA (US); Daniel White, Suwanee, GA (US); Glenn Noronha, Atlanta, GA (US); Brian Burke, Cary, NC (US)

(73) Assignee: CLEARSIDE BIOMEDICAL, INC., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/673,073

(22) Filed: Aug. 9, 2017

(65) Prior Publication Data
US 2017/0333416 A1 Nov. 23, 2017

Related U.S. Application Data

(63) Continuation of application No. 15/454,636, filed on Mar. 9, 2017, which is a continuation of application
(Continued)

(51) Int. Cl.
*A61K 31/4439* (2006.01)
*A61K 47/26* (2006.01)
(Continued)

(52) U.S. Cl.
CPC ........ *A61K 31/4439* (2013.01); *A61K 9/0019* (2013.01); *A61K 9/0048* (2013.01);
(Continued)

(58) Field of Classification Search
CPC .. A61K 31/4439; A61K 9/0048; A61K 47/26; A61K 45/06; A61K 31/573;
(Continued)

(56) References Cited

U.S. PATENT DOCUMENTS

| 2,187,259 A | 1/1940 | Barnhart |
| 2,841,145 A | 7/1958 | Epps |

(Continued)

FOREIGN PATENT DOCUMENTS

| CA | 2639322 | 3/2009 |
| CN | 1706365 | 12/2005 |

(Continued)

OTHER PUBLICATIONS

Brown, David M., "Aflibercept for Treatment of Diabetic Macular Edema," Retina Today, Jul./Aug. 2011, pp. 59-60.*
(Continued)

*Primary Examiner* — Aradhana Sasan
(74) *Attorney, Agent, or Firm* — Cooley LLP

(57) ABSTRACT

Methods and devices are provided for targeted non-surgical administration of a drug formulation to the suprachoroidal space (SCS) of the eye of a human subject for the treatment of a posterior ocular disorder or a choroidal malady. In one embodiment, the method comprises inserting a hollow microneedle into the eye at an insertion site and infusing a drug formulation through the inserted microneedle and into the suprachoroidal space of the eye, wherein the infused drug formulation flows within the suprachoroidal space away from the insertion site during the infusion. In one embodiment, the fluid drug formulation comprises drug nanoparticles or microparticles.

12 Claims, 40 Drawing Sheets

Related U.S. Application Data

No. 14/441,151, filed as application No. PCT/US2013/069156 on Nov. 8, 2013, now abandoned.

(60) Provisional application No. 61/898,926, filed on Nov. 1, 2013, provisional application No. 61/873,660, filed on Sep. 4, 2013, provisional application No. 61/819,388, filed on May 3, 2013, provisional application No. 61/785,229, filed on Mar. 14, 2013, provisional application No. 61/773,124, filed on Mar. 5, 2013, provisional application No. 61/745,237, filed on Dec. 21, 2012, provisional application No. 61/734,872, filed on Dec. 7, 2012, provisional application No. 61/724,144, filed on Nov. 8, 2012.

(51) Int. Cl.
*A61K 45/06* (2006.01)
*A61K 9/00* (2006.01)
*A61K 47/38* (2006.01)
*A61K 9/16* (2006.01)
*A61K 31/573* (2006.01)
*A61K 47/12* (2006.01)
*A61K 9/10* (2006.01)
*A61K 39/00* (2006.01)
*A61M 37/00* (2006.01)
*C07K 16/22* (2006.01)

(52) U.S. Cl.
CPC ............... *A61K 9/10* (2013.01); *A61K 9/16* (2013.01); *A61K 31/573* (2013.01); *A61K 45/06* (2013.01); *A61K 47/12* (2013.01); *A61K 47/26* (2013.01); *A61K 47/38* (2013.01); *A61M 37/0015* (2013.01); *C07K 16/22* (2013.01); *A61K 2039/505* (2013.01); *A61K 2039/54* (2013.01); *A61K 2300/00* (2013.01); *A61M 2037/0023* (2013.01); *A61M 2037/0061* (2013.01)

(58) Field of Classification Search
CPC . A61K 47/38; A61K 9/10; A61K 9/16; A61K 47/12; A61K 9/0019; C07K 16/22; A61M 37/0015; A61M 2037/0023; A61M 2037/0061
See application file for complete search history.

(56) References Cited

U.S. PATENT DOCUMENTS

| | | |
|---|---|---|
| 2,939,459 A | 6/1960 | Lazarte et al. |
| 3,376,999 A | 4/1968 | De Hart et al. |
| 3,477,432 A | 11/1969 | Shaw |
| 3,739,947 A | 6/1973 | Baumann et al. |
| 3,762,540 A | 10/1973 | Baumann et al. |
| 3,788,320 A | 1/1974 | Dye |
| 3,892,311 A | 7/1975 | Sneider |
| 3,964,482 A | 6/1976 | Gerstel et al. |
| 4,226,328 A | 10/1980 | Beddow |
| 4,377,897 A | 3/1983 | Eichenbaum et al. |
| 4,383,530 A | 5/1983 | Bruno |
| 4,417,887 A | 11/1983 | Koshi |
| 4,501,363 A | 2/1985 | Isbey, Jr. |
| 4,564,016 A | 1/1986 | Maurice et al. |
| 4,601,708 A | 7/1986 | Jordan |
| 4,615,331 A | 10/1986 | Kramann |
| 4,689,040 A | 8/1987 | Thompson |
| 4,708,147 A | 11/1987 | Haaga |
| 4,717,383 A | 1/1988 | Phillips et al. |
| 4,736,850 A | 4/1988 | Bowman et al. |
| 4,755,169 A | 7/1988 | Sarnoff et al. |
| 4,795,432 A | 1/1989 | Karczmer |
| 4,804,371 A | 2/1989 | Vaillancourt |
| 4,826,490 A | 5/1989 | Byrne et al. |
| 4,826,871 A | 5/1989 | Gressel et al. |
| 4,889,529 A | 12/1989 | Haindl |
| 4,941,874 A | 7/1990 | Sandow et al. |
| 4,966,773 A | 10/1990 | Gressel et al. |
| 5,015,240 A | 5/1991 | Soproni et al. |
| 5,066,276 A | 11/1991 | Wang |
| 5,098,389 A | 3/1992 | Cappucci |
| 5,137,447 A | 8/1992 | Hunter |
| 5,164,188 A | 11/1992 | Wong |
| 5,172,807 A | 12/1992 | Dragan et al. |
| 5,181,909 A | 1/1993 | McFarlane |
| 5,273,530 A | 12/1993 | del Cerro et al. |
| 5,279,564 A | 1/1994 | Taylor |
| 5,295,972 A | 3/1994 | Mischenko |
| 5,300,084 A | 4/1994 | Johnson |
| 5,312,361 A | 5/1994 | Zadini et al. |
| 5,354,286 A | 10/1994 | Mesa et al. |
| 5,364,373 A | 11/1994 | Waskonig et al. |
| 5,364,374 A | 11/1994 | Morrison et al. |
| 5,364,734 A | 11/1994 | Morrison et al. |
| 5,397,313 A | 3/1995 | Gross |
| 5,399,159 A | 3/1995 | Chin et al. |
| 5,407,070 A | 4/1995 | Bascos et al. |
| 5,443,505 A | 8/1995 | Wong et al. |
| 5,538,503 A | 7/1996 | Henley et al. |
| 5,547,467 A | 8/1996 | Pliquett et al. |
| 5,632,740 A | 5/1997 | Koch et al. |
| 5,658,256 A | 8/1997 | Shields |
| D383,049 S | 9/1997 | Concari et al. |
| 5,667,491 A | 9/1997 | Pliquett et al. |
| 5,681,825 A | 10/1997 | Lindqvist et al. |
| 5,766,242 A | 6/1998 | Wong et al. |
| 5,767,079 A | 6/1998 | Glaser et al. |
| 5,779,668 A | 7/1998 | Grabenkort |
| 5,788,679 A | 8/1998 | Gravlee, Jr. |
| 5,792,099 A | 8/1998 | DeCamp et al. |
| 5,817,075 A | 10/1998 | Giungo |
| 5,824,072 A | 10/1998 | Wong |
| 5,911,223 A | 6/1999 | Weaver et al. |
| 5,952,378 A | 9/1999 | Stjernschantz et al. |
| 5,968,022 A | 10/1999 | Saito |
| 6,059,111 A | 5/2000 | Davilla et al. |
| 6,083,199 A | 7/2000 | Thorley et al. |
| 6,143,329 A | 11/2000 | Kim |
| 6,280,470 B1 | 8/2001 | Peyman |
| 6,299,603 B1 | 10/2001 | Hecker et al. |
| 6,309,347 B1 | 10/2001 | Takahashi et al. |
| 6,309,374 B1 | 10/2001 | Hecker et al. |
| 6,319,240 B1 | 11/2001 | Beck |
| 6,334,856 B1 | 1/2002 | Allen et al. |
| 6,378,526 B1 | 4/2002 | Bowman et al. |
| 6,387,078 B1 | 5/2002 | Gillespie, III |
| 6,397,849 B1 | 6/2002 | Bowman et al. |
| 6,432,090 B1 | 8/2002 | Brunel |
| 6,503,231 B1 | 1/2003 | Prausnitz et al. |
| 6,524,581 B1 | 2/2003 | Adamis |
| 6,540,725 B1 | 4/2003 | Ponzi |
| 6,551,299 B2 | 4/2003 | Miyoshi et al. |
| 6,611,707 B1 | 8/2003 | Prausnitz et al. |
| 6,622,864 B1 | 9/2003 | Debbs et al. |
| 6,743,211 B1 | 6/2004 | Prausnitz et al. |
| 6,773,916 B1 | 8/2004 | Thiel et al. |
| D499,153 S | 11/2004 | Kuo |
| 6,883,222 B2 | 4/2005 | Landau |
| 6,918,889 B1 | 7/2005 | Brunel |
| 6,929,623 B2 | 8/2005 | Stone |
| 6,936,053 B1 | 8/2005 | Weiss |
| 7,025,774 B2 | 4/2006 | Freeman et al. |
| 7,150,735 B2 | 12/2006 | Hickle |
| 7,207,965 B2 | 4/2007 | Simon |
| 7,207,980 B2 | 4/2007 | Christian et al. |
| 7,211,062 B2 | 5/2007 | Kwon |
| 7,214,212 B2 | 5/2007 | Pommereau et al. |
| 7,226,439 B2 | 6/2007 | Prausnitz et al. |
| 7,316,676 B2 | 1/2008 | Peyman et al. |
| 7,425,207 B2 | 9/2008 | Miller et al. |
| 7,435,237 B2 | 10/2008 | Tan |
| 7,468,057 B2 | 12/2008 | Ponzi |

(56) References Cited

U.S. PATENT DOCUMENTS

| | | |
|---|---|---|
| D590,690 S | 4/2009 | Bertini |
| D598,543 S | 8/2009 | Vogel et al. |
| 7,569,035 B1 | 8/2009 | Wilmot et al. |
| 7,615,041 B2 | 11/2009 | Sullivan et al. |
| 7,678,077 B2 | 3/2010 | Harris et al. |
| 7,678,078 B1 | 3/2010 | Peyman et al. |
| 7,722,581 B2 | 5/2010 | Peyman |
| 7,914,803 B2 | 3/2011 | Chowhan et al. |
| 7,918,814 B2 | 4/2011 | Prausnitz et al. |
| 7,918,874 B2 | 4/2011 | Siegal |
| 7,947,660 B2 | 5/2011 | Clark et al. |
| 7,967,772 B2 | 6/2011 | McKenzie et al. |
| 8,003,124 B2 | 8/2011 | Varner et al. |
| 8,114,110 B2 | 2/2012 | Bednarek et al. |
| 8,137,312 B2 | 3/2012 | Sundar et al. |
| 8,172,830 B2 | 5/2012 | Christian et al. |
| 8,173,617 B2 | 5/2012 | Clark et al. |
| 8,192,408 B2 | 6/2012 | Nazzaro et al. |
| 8,197,435 B2 | 6/2012 | Prausnitz et al. |
| 8,197,443 B2 | 6/2012 | Sundar et al. |
| 8,221,353 B2 | 7/2012 | Cormier et al. |
| 8,235,967 B2 | 8/2012 | Chevallier et al. |
| D667,111 S | 9/2012 | Robinson |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,430,862 B2 | 4/2013 | Peyman et al. |
| 8,448,786 B2 | 5/2013 | Tomes et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,770,361 B2 | 9/2017 | Andino et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1 | 8/2002 | Feinberg et al. |
| 2002/0112981 A1 | 8/2002 | Cooper et al. |
| 2002/0156413 A1 | 10/2002 | Williams et al. |
| 2003/0009113 A1 | 1/2003 | Olson |
| 2003/0083645 A1 | 5/2003 | Angel et al. |
| 2003/0139729 A1 | 7/2003 | Stegmann et al. |
| 2003/0171722 A1 | 9/2003 | Paques et al. |
| 2004/0039253 A1 | 2/2004 | Peyman et al. |
| 2004/0106904 A1 | 6/2004 | Gonnelli et al. |
| 2004/0122359 A1 | 6/2004 | Wenz et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0089545 A1 | 4/2005 | Kuwano et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0171507 A1 | 8/2005 | Christian et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0084942 A1 | 4/2006 | Kim et al. |
| 2006/0086689 A1 | 4/2006 | Raju |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093877 A1 | 4/2007 | Beecham et al. |
| 2007/0151882 A1 | 7/2007 | Cocheteux et al. |
| 2007/0178197 A1 | 8/2007 | Larue et al. |
| 2007/0202186 A1 | 8/2007 | Yamamoto et al. |
| 2007/0224278 A1 | 9/2007 | Lyons et al. |
| 2007/0225654 A1 | 9/2007 | Hess et al. |
| 2007/0233037 A1 | 10/2007 | Gifford et al. |
| 2007/0260201 A1 | 11/2007 | Prausnitz et al. |
| 2007/0270745 A1 | 11/2007 | Nezhat et al. |
| 2007/0270768 A1 | 11/2007 | Dacquay et al. |
| 2007/0282405 A1 | 12/2007 | Wong et al. |
| 2007/0287985 A1 | 12/2007 | Estes et al. |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0071246 A1 | 3/2008 | Nazzaro et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0152694 A1 | 6/2008 | Lobl et al. |
| 2008/0177239 A1 | 7/2008 | Li et al. |
| 2008/0228127 A1 | 9/2008 | Burns et al. |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0088721 A1 | 4/2009 | Bizemont et al. |

(56) References Cited

U.S. PATENT DOCUMENTS

| | | |
|---|---|---|
| 2009/0105749 A1 | 4/2009 | De Juan et al. |
| 2009/0148527 A1 | 6/2009 | Robinson |
| 2009/0259180 A1 | 10/2009 | Choi |
| 2009/0287161 A1 | 11/2009 | Traub et al. |
| 2009/0312782 A1 | 12/2009 | Park |
| 2010/0010452 A1 | 1/2010 | Paques et al. |
| 2010/0012537 A1 | 1/2010 | Farrar et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0256597 A1 | 10/2010 | Prausnitz et al. |
| 2010/0312120 A1 | 12/2010 | Meier |
| 2011/0004265 A1 | 1/2011 | Wenger et al. |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0282298 A1 | 11/2011 | Again et al. |
| 2011/0306923 A1 | 12/2011 | Roy |
| 2012/0004245 A1 | 1/2012 | May et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0041265 A1 | 2/2013 | Sostek et al. |
| 2013/0060202 A1 | 3/2013 | Thorley et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0218269 A1 | 8/2013 | Schachar et al. |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0012226 A1 | 1/2014 | Hochman |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |
| 2014/0135716 A1 | 5/2014 | Clarke et al. |
| 2014/0194834 A1 | 7/2014 | Passaglia et al. |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0276482 A1 | 9/2014 | Astafieva et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0129456 A1 | 5/2015 | Miller et al. |
| 2015/0133415 A1 | 5/2015 | Whitcup |
| 2015/0209180 A1 | 7/2015 | Prausnitz et al. |
| 2015/0258120 A1 | 9/2015 | Zarnitsyn et al. |
| 2015/0320596 A1 | 11/2015 | Gifford, III et al. |
| 2016/0106584 A1 | 4/2016 | Andino et al. |
| 2016/0193080 A1 | 7/2016 | Hammack et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2017/0095369 A1 | 4/2017 | Andino et al. |
| 2017/0224435 A1 | 8/2017 | Godfrey et al. |
| 2017/0224534 A1 | 8/2017 | Andino et al. |
| 2017/0290702 A1 | 10/2017 | Yamamoto et al. |
| 2017/0340560 A1 | 11/2017 | Yamamoto et al. |

FOREIGN PATENT DOCUMENTS

| | | |
|---|---|---|
| CN | 1736474 | 2/2006 |
| CN | 101052434 A | 10/2007 |
| CN | 101351239 A | 1/2009 |
| CN | 201356711 Y | 12/2009 |
| CN | 101959519 A | 1/2011 |
| EA | 006961 | 6/2006 |
| EP | 1568359 | 8/2005 |
| EP | 2193821 | 6/2010 |
| EP | 2307055 | 4/2011 |
| JP | 2001-525826 | 12/2001 |
| JP | 2009-183441 | 8/2009 |
| JP | 2009-531298 | 9/2009 |
| RU | 2344767 | 1/2009 |
| RU | 2353393 | 4/2009 |
| RU | 2428956 | 9/2011 |
| WO | WO 92/08406 | 5/1992 |
| WO | WO 94/01124 | 1/1994 |
| WO | WO 94/12217 | 6/1994 |
| WO | WO 96/09838 | 4/1996 |
| WO | WO 98/51348 | 11/1998 |
| WO | WO 2000/007530 | 2/2000 |
| WO | WO 2000/007565 | 2/2000 |
| WO | WO 2001/041685 | 6/2001 |
| WO | WO 2003/002094 | 1/2003 |
| WO | WO 2003/024507 | 3/2003 |

(56) References Cited

FOREIGN PATENT DOCUMENTS

| WO | WO 2005/011741 | 2/2005 |
|---|---|---|
| WO | WO 2005/069831 | 8/2005 |
| WO | WO 2005/072701 | 8/2005 |
| WO | WO 2005/107845 | 11/2005 |
| WO | WO 2006/004595 | 1/2006 |
| WO | WO 2006/042252 | 4/2006 |
| WO | WO 2006/058189 | 6/2006 |
| WO | WO 2006/128034 | 11/2006 |
| WO | WO 2006/138719 | 12/2006 |
| WO | WO 2007/100745 | 9/2007 |
| WO | WO 2007/131050 | 11/2007 |
| WO | WO 2007/150018 | 12/2007 |
| WO | WO 2008/082637 | 7/2008 |
| WO | WO 2009/105534 | 8/2009 |
| WO | WO 2009/114521 | 9/2009 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/139713 | 11/2011 |
| WO | WO 2012/051575 | 4/2012 |
| WO | WO 2012/118498 | 9/2012 |
| WO | WO 2012/125869 | 9/2012 |
| WO | WO 2012/125872 | 9/2012 |
| WO | WO 2012/162459 | 11/2012 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/074823 | 5/2014 |
| WO | WO 2014/179698 | 11/2014 |
| WO | WO 2014/197317 | 12/2014 |
| WO | WO 2015/015467 | 2/2015 |
| WO | WO 2015/095772 | 6/2015 |
| WO | WO 2015/195842 | 12/2015 |
| WO | WO 2015/196085 | 12/2015 |
| WO | WO 2016/042162 | 3/2016 |
| WO | WO 2016/042163 | 3/2016 |
| WO | WO 2017/120600 | 7/2017 |
| WO | WO 2017/120601 | 7/2017 |
| WO | WO 2017/139375 | 8/2017 |
| WO | WO 2017/190142 | 11/2017 |
| WO | WO 2017/192565 | 11/2017 |

OTHER PUBLICATIONS

Claims filed in copending case U.S. Appl. No. 15/454,636 on Mar. 9, 2017, pp. 1-30.*
Office Action for U.S. Appl. No. 11/743,535, dated Aug. 19, 2010, 7 pages.
Office Action for U.S. Appl. No. 11/743,535, dated Dec. 29, 2009, 6 pages.
International Search Report and Written Opinion for International Application No. PCT/US2007/068055, dated Nov. 7, 2007, 13 pages.
Extended European Search Report for European Application No. 11777924.9, dated Feb. 4, 2015, 7 pages.
Office Action for Russian Application No. 2012147341, dated Feb. 26, 2015, 8 pages.
Office Action for U.S. Appl. No. 12/767,768, dated Jun. 10, 2011, 5 pages.
International Search Report and Written Opinion for International Application No. PCT/US2011/033987, dated Feb. 14, 2012, 7 pages.
Office Action for U.S. Appl. No. 13/447,246, dated Oct. 28, 2013, 5 pages.
Office Action for U.S. Appl. No. 13/453,407, dated Mar. 20, 2013, 5 pages.
Extended Search Report for European Application No. 13833318.2, dated Apr. 1, 2016, 7 pages.
Office Action for U.S. Appl. No. 14/424,685, dated Jun. 10, 2016, 10 pages.

International Search Report and Written Opinion for International Application No. PCT/US2013/056863, dated Nov. 26, 2013, 8 pages.
First Office Action for Chinese Application No. 201380069089.0, dated Nov. 28, 2016, 30 pages.
Office Action for Eurasian Application No. 201590902, dated Apr. 4, 2017, 2 pages.
Supplementary Partial European Search Report for European Application No. 13853777, dated Jul. 4, 2016, 6 pages.
Search Report and Written Opinion for Singapore Application No. 11201503637S, dated Jun. 23, 2016, 9 pages.
Office Action for U.S. Appl. No. 14/441,151, dated Sep. 9, 2016, 18 pages.
International Search Report and Written Opinion for International Application No. PCT/US2013/069156, dated Mar. 10, 2014, 11 pages.
Office Action for U.S. Appl. No. 15/001,610, dated Sep. 8, 2016, 12 pages.
Office Action for U.S. Appl. No. 15/086,485, dated Jul. 28, 2016, 9 pages.
International Search Report and Written Opinion for International Application No. PCT/US2014/040254, dated Oct. 31, 2014, 9 pages.
Office Action for Eurasian Application No. 201592109, dated Apr. 1, 2016, 4 pages.
International Search Report and Written Opinion for International Application No. PCT/US2014/036590, dated Dec. 10, 2014, 10 pages.
Office Action for U.S. Appl. No. 14/268,687, dated May 19, 2016, 6 pages.
Office Action for U.S. Appl. No. 14/523,243, dated Feb. 27, 2015, 14 pages.
International Search Report and Written Opinion for International Application No. PCT/US2015/036299, dated Nov. 10, 2015, 11 pages.
International Search Report and Written Opinion for International Application No. PCT/US2015/036715, dated Jan. 19, 2016, 9 pages.
Office Action for Canadian Application No. 162010, dated Aug. 25, 2015, 1 page.
International Search Report and Written Opinion for International Application No. PCT/US2014/071623, dated Jun. 25, 2015, 18 pages.
Office Action for Chinese Application No. 200780014501.3, dated Mar. 11, 2010, 6 pages.
Office Action for Chinese Application No. 200780014501.3, dated Aug. 26, 2010, 10 pages.
Office Action for European Application No. 07751620.1, dated Sep. 13, 2013, 7 pages.
Extended European Search Report for European Application No. 07751620.1, dated Jan. 15, 2013, 10 pages.
Office Action for European Application No. 07751620.1, dated Dec. 11, 2014, 5 pages.
Invitation pursuant to Article 94(3) and Rule 71(1) for European Application No. 07751620.1, dated Feb. 29, 2016, 3 pages.
Office Action for Japanese Application No. 2008-556462, dated Jul. 24, 2012, 15 pages.
Office Action for India Application No. 3345/KOLNP/2008, dated May 21, 2015, 3 pages.
Office Action for Singapore Application No. 200805936-2, dated Oct. 15, 2012, 7 pages.
Search Report and Written Opinion for Singapore Application No. 200805936-2, dated Jun. 8, 2010, 13 pages.
Supplementary Search Report for Singapore Application No. 200805936-2, dated May 6, 2011, 8 pages.
Supplementary Search Report for Singapore Application No. 200805936-2, dated May 26, 2011, 8 pages.
Office Action for U.S. Appl. No. 11/709,941, dated Jun. 24, 2014, 11 pages.
Office Action for U.S. Appl. No. 11/709,941, dated Mar. 23, 2011, 9 pages.
Office Action for U.S. Appl. No. 11/709,941, dated Feb. 11, 2015, 14 pages.

(56) References Cited

OTHER PUBLICATIONS

Office Action for U.S. Appl. No. 11/709,941, dated Oct. 27, 2011, 8 pages.
Office Action for U.S. Appl. No. 11/709,941, dated Apr. 12, 2016, 25 pages.
International Search Report and Written Opinion for International Application No. PCT/US2007/004874, dated Jun. 4, 2008, 6 pages.
Office Action for Chinese Application No. 201110093644.6, dated Mar. 26, 2012, 11 pages.
Office Action for Chinese Application No. 201110093644.6, dated Sep. 7, 2012, 8 pages.
Office Action for Chinese Application No. 201110093644.6, dated Dec. 14, 2012, 3 pages.
Office Action for U.S. Appl. No. 13/842,218, dated Jul. 5, 2016, 11 pages.
Office Action for U.S. Appl. No. 13/842,288, dated Oct. 6, 2015, 10 pages.
First Office Action for Chinese Application No. 201180060268.9, dated Oct. 10, 2014, 9 pages.
Second Office Action for Chinese Application No. 201180060268.9, dated Jun. 18, 2015, 4 pages.
Third Office Action for Chinese Application No. 201180060268.9, dated Feb. 5, 2016, 6 pages.
Office Action for Japanese Application No. 2013-534049, dated Sep. 1, 2015, 11 pages.
Office Action for U.S. Appl. No. 13/273,775, dated Feb. 12, 2015, 13 pages.
Office Action for U.S. Appl. No. 13/273,775, dated Jul. 3, 2014, 12 pages.
International Search Report and Written Opinion for International Application No. PCT/US2011/056433, dated Apr. 25, 2012, 17 pages.
Office Action for Chinese Application No. 201510144330.2, dated Apr. 5, 2016, 17 pages.
Abbott Medical Optics (HEALON5@OVD on http://abbottmedicaloptics.com/products/cataract/ovds/healon5-viscoelastic (2004).
Anthem, Medical Policy, Suprachoroidal Injection of a Pharmacologic Agent, Nov. 14, 2013, Retrieved from the Internet: <URL: http://www.anthem.com/medicalpolicies/policies/mp_pw_b076412.htm>, 3 pages.
Beer, P. J. et al., "Photographic Evidence of Vitreous Wicks After Intravitreal Injections," Retina Today, 2(2):24-39 (Mar. 2007).
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.
Careforde Healthcare, B Braun Glass Loss-Of-Resistance Syringes # 332155—5cc Glass Loss-Of-Resistance Syringe, Luer Lock Metal Tip, 10/cs, [online], <http://careforde.com/b-braun-glass-loss-of-resistance-syringes-332155-5cc-glass-loss of-r . . . > (2014), 2 pages.
Careforde Healthcare, B Braun Glass Loss-Of-Resistance Syringes # 332158—10cc Glass Loss-Of-Resistance Syringe, Luer Slip Metal Tip, 10/cs, (2014), 2 pages.
Careforde Healthcare, B Braun Perifix Plastic Loss-Of-Resistance Syringes #332152—8cc Plastic Luer Lock Loss-of-Resistance Syringe, 50/cs, [online], <http://careforde.com/b-braun-perifix-plastic-loss-of-resistance-syringes-332152-8cc-plasti . . . > (2014), 2 pages.
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).
Doncaster and Bassetlaw Hospitals, NHS Foundation Trust, "Intravitreal injection of triamcinolone," Jul. 2010, [Online], <URL: http://www.dbh.nhs.uk/Library/Patient_Information_Leaflets/WPR32110%20IIT%20No%20crops.pdf>, 2 pages.
Edwards, A. et al., "Fiber matrix model of sclera and corneal stroma for drug delivery to the eye," AlChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, <URL: http:/en.wikipedia.org/wiki/Epidural>, 21 pages.
Feldkamp, L. A. et al., "Practical cone-beam algorithm," J. Opt Soc. Am. A, 1(6):612-619 (1984).
Geroski, D. H. et al., "Drug delivery for posterior segment eye disease," Invest Ophthalmol. Vis. Sci., 41(5):961-964 (2000).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Heller, J., Ocular delivery using poly(ortho esters), Adv. Drug. Deliv. Rev., 57(14):2053-2062 (2005).
Hoagan et al., Chapter Eight, Choroid, In Histology of the Human Eye, 9 pages (1971).
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Measurement and Prediction of Lateral Diffusion within Human Sclera," Investigative Ophthalmology & Visual Science, 47(7):3011-3016 (2006).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Lee, S-B et al., "Drug delivery through the sclera: effects of thickness, hydration and sustained release systems," Experimental Eye Research, 78:599-607 (2004).
Lee et al., "Thixotropic property in pharmaceutical formulations," Journal of Controlled Release (2009) 136:88-98.
Lindfield, D. et al., "Suprachoroidal Devices in Glaucoma. The Past, Present, and Future of Surgery for Suprachoroidal Drainage," Cataract & Refractive Surgery Today [online], Oct. 2013, Retrieved from the Internet: <URL: http://bmctoday.net/crstodayeurope/2013/10/article.asp?f=suprachoroidal-devices-in-glau . . . >, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).
Norman, D., Epidural analgesia using loss of resistance with air versus saline: Does it make a difference? Should we reevaluate our practice?, AANA Journal, 71(6):449-453 (Dec. 2003).
Olsen, T. W. et al., "Cannulation of the Suprachoroidal Space: A Novel Drug Delivery Methodology to the Posterior Segment," American J. Opthamology, 142(5):777-787 (2006).
Olsen, T., "Drug Delivery to the Suprachoroidal Space Shows Promise," Retina Today, pp. 36-39 (Mar./Apr. 2007).
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Patel, S. et al., "Suprachoroidal Drug Delivery Using Microneedles," Invest. Ophthalmol. Vis. Sci., 49:E-Abstract 5006 (2008), 2 pages.
Patel, S. et al., "Drug Binding to Sclera," Invest Ophthalmol Vis Sci., 50:E-Abstract 5968 (2009), 2 pages.

(56) References Cited

OTHER PUBLICATIONS

Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Penkov, M. A. et al., "A ten-year experience with usage of the method of supra-choroidal administration of medicinal substances," Oftalmol. Zh., 35(5):281-285 (1980).
Prausnitz, M. R. et al., "Permeability of cornea, sclera and conjunctiva: A literature analysis for drug delivery to the eye," Journal of Pharmaceutical Sciences, 87(12):1479-1488 (1998).
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
Shuler, R. K. et al., "Scleral Permeability of a Small, Single-Stranded Oligonucleotide," Journal of Ocular Pharmacology and Therapeutics, 20(2):159-168 (2004) (Abstract).
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
Office Action for Canadian Application No. 2797258, dated Nov. 21, 2016, 3 pages.
Examination Report No. 1 for Australian Application No. 2015230874, dated Jul. 28, 2017, 11 pages.
Office Action for Japanese Application No. 2016-068174, dated Mar. 1, 2017, 8 pages.
Office Action for U.S. Appl. No. 14/136,657, dated Dec. 16, 2016, 7 pages.
Office Action for U.S. Appl. No. 14/424,685, dated Dec. 12, 2016, 15 pages.
Examination Report No. 1 for Australian Application No. 2013342275, dated Sep. 5, 2017, 4 pages.
Second Office Action for Chinese Application No. 201380069089.0, dated Aug. 22, 2017, 10 pages.
Notice of Reasons for Rejection for Japanese Application No. 2015-540925, dated Oct. 24, 2017, 9 pages.
Second Written Opinion for Singapore Application No. 11201503637S, dated Dec. 30, 2016, 6 pages.
Third Written Opinion for Singapore Application No. 11201503637S, dated Oct. 23, 2017, 4 pages.
Supplementary European Search Report for European Application No. 14808034.4, dated Jan. 23, 2017, 7 pages.
Office Action for European Application No. 14808034.4, dated Nov. 8, 2017, 4 pages.
Office Action for U.S. Appl. No. 14/894,161, dated Dec. 27, 2016, 17 pages.
Office Action for U.S. Appl. No. 14/894,161, dated Sep. 20, 2017, 21 pages.
Extended Search Report for European Application No. 14791646.4, dated Nov. 21, 2016.
Office Action for European Application No. 14791646.4, dated Dec. 4, 2017, 5 pages.
Search Report and Written Opinion for Singapore Application No. 11201509051V, dated Nov. 2, 2016, 6 pages.
Examination Report for Singapore Application No. 11201509051V, dated Feb. 1, 2017, 4 pages.
Office Action for U.S. Appl. No. 15/383,582, dated May 5, 2017, 10 pages.
Summons to Attend Oral Proceedings Pursuant to Rule 115(1) EPC for European Application No. 07751620.1, mailed Jun. 13, 2017, 8 pages.
Office Action for U.S. Appl. No. 11/709,941, dated Dec. 27, 2016.
Examination Report for European Application No. 11776049.6, dated Oct. 25, 2016.
Second Office Action for Chinese Application No. 201510144330.2, dated Dec. 20, 2016, 13 pages.
Third Office Action for Chinese Application No. 201510144330.2, dated Jun. 28, 2017, 3 pages.
Office Action for U.S. Appl. No. 14/821,310, dated Jul. 14, 2017.
First Office Action for Chinese Application No. 201610805842.3, dated Jul. 21, 2017, 4 pages.
Office Action for U.S. Appl. No. 15/427,823, dated Apr. 20, 2017, 8 pages.
Office Action for U.S. Appl. No. 15/427,823, dated Sep. 27, 2017, 7 pages.
International Search Report and Written Opinion for International Application No. PCT/US2017/017014, dated Apr. 27, 2017, 13 pages.
International Search Report and Written Opinion for International Application No. PCT/US2017/012755, dated Apr. 12, 2017, 8 pages.
International Search Report and Written Opinion for International Application No. PCT/US2017/012757, dated Apr. 12, 2017, 11 pages.
International Search Report and Written Opinion for International Application No. PCT/US2017/030609, dated Oct. 6, 2017, 12 pages.
International Search Report and Written Opinion for International Application No. PCT/US2017/030439, dated Aug. 1, 2017, 12 pages.
Dinning, W.J., "Steroids and the eye-indications and complications," Postgraduate Medical Journal, vol. 52, 1976, pp. 634-638.
Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.
Patel, S. R. et al., "Targeted administration into the suprachoroidal spcae using a microneedle for drug delivery to the posterior segment of the eye," Investigative Ophthalmology & Visual Science, 53(8):4433-4441 (Jul. 2012).
Extended European Search Report for European Application No. 15808944.1, dated Jan. 19, 2018, 14 pages.
Cho, S. W. et al., "Drug delivery to the suprachoroidal space," Chap. 12 in: Ocular Drug Delivery Systems: Barriers and Application of Nanoparticulate Systems, Thassu, D. et al. (eds.), CRC Press, pp. 235-258 (2012).
Patel, S. R. et al., "Suprachoroidal drug delivery to the back of the eye using hollow microneedles," Pharmaceutical Research, 28(1):166-176 (2011), Published online: Sep. 21, 2010.

\* cited by examiner

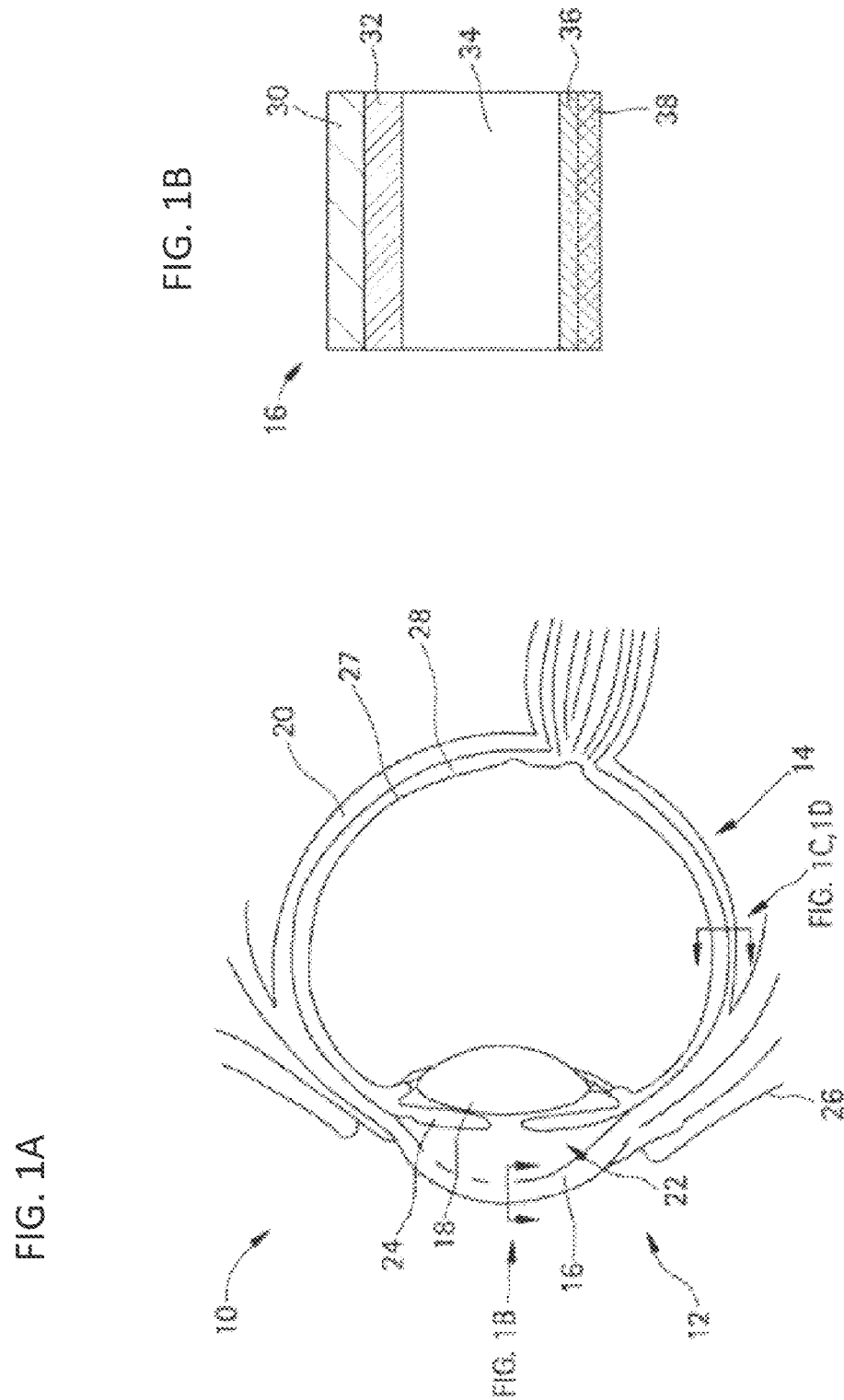

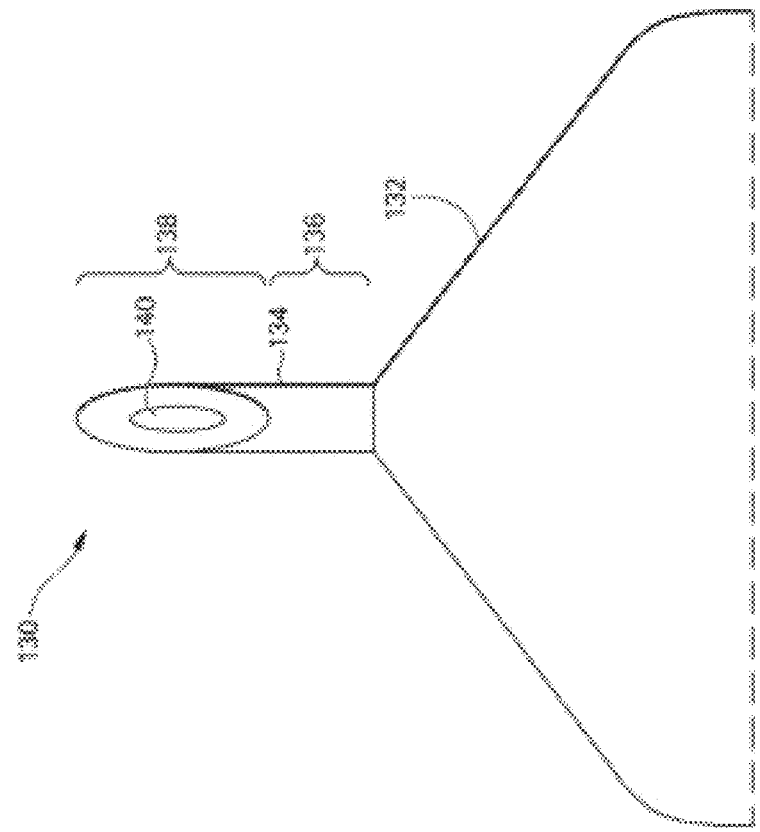
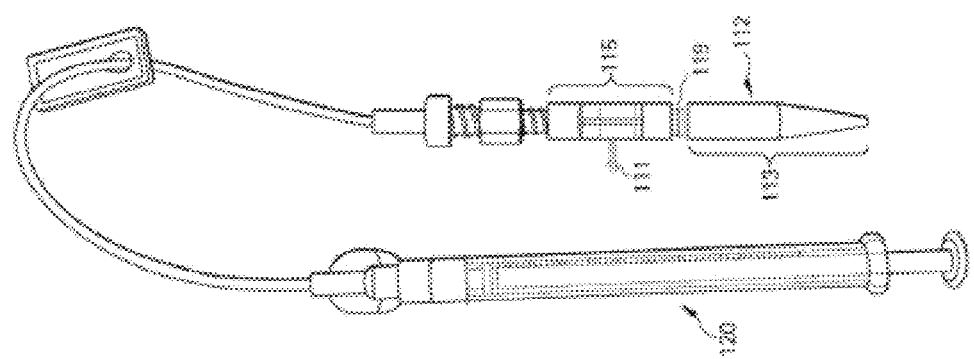

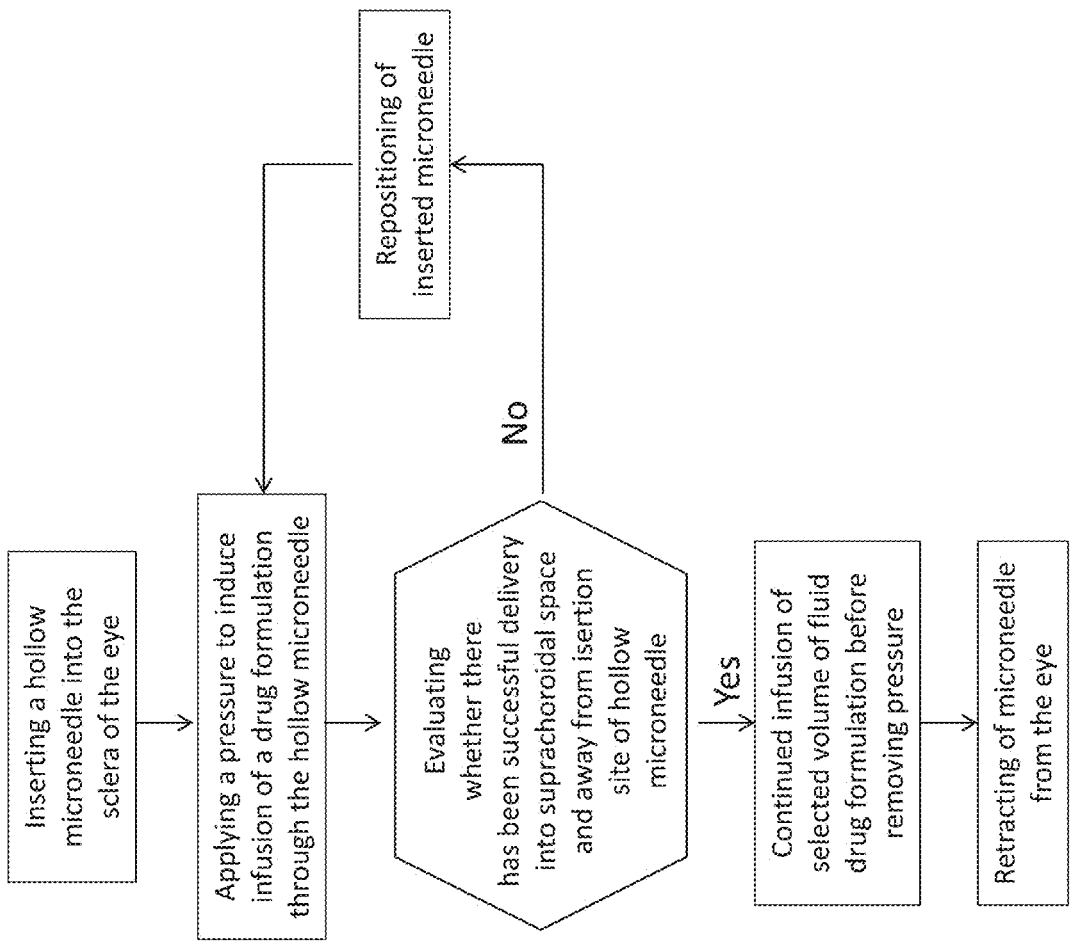

FIG. 20B
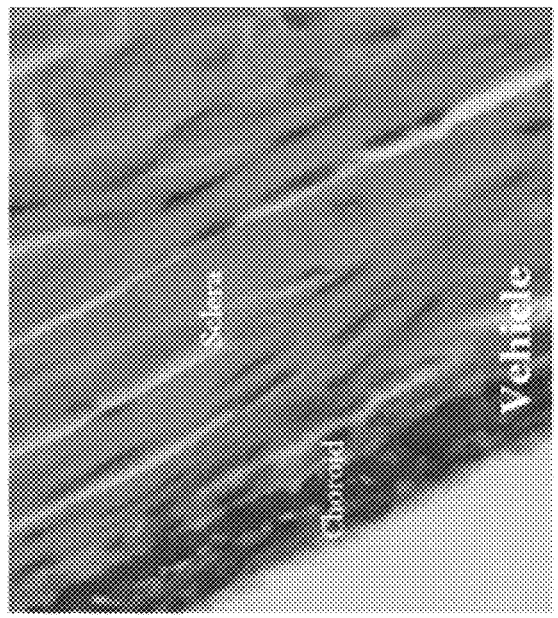
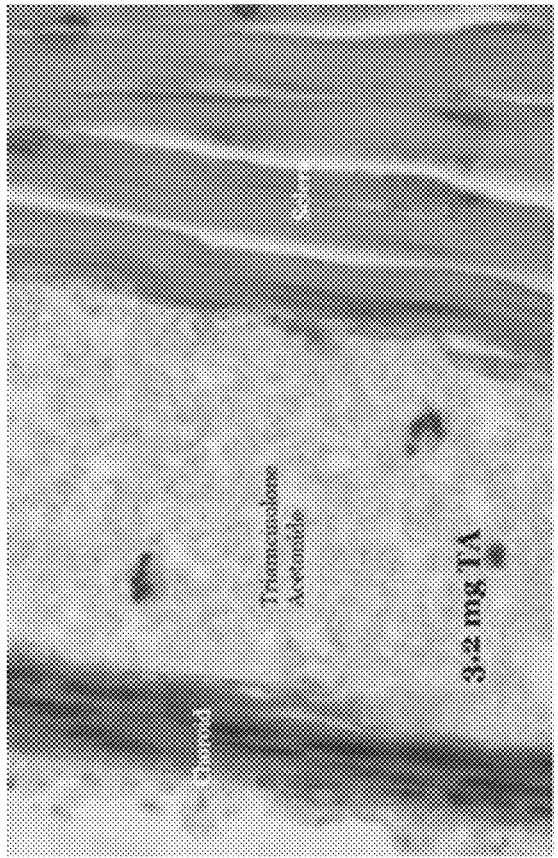

FIG. 20C
Single Dose GLP Toxicology in Rabbits
Systemic Exposure, n=10 rabbits
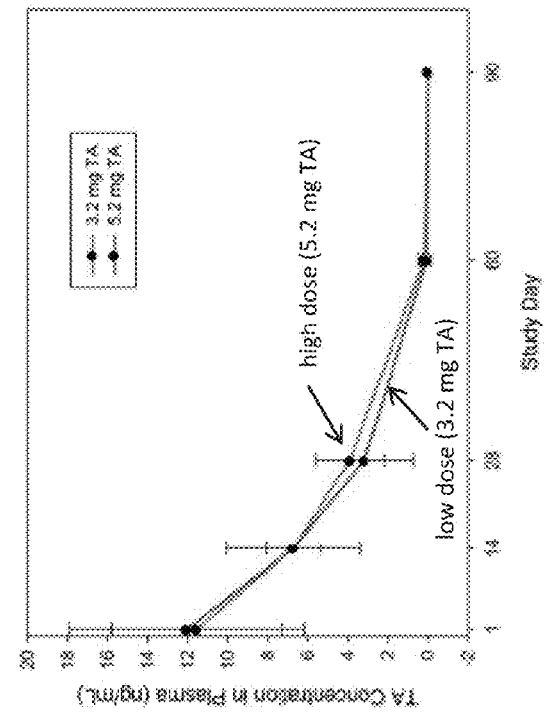
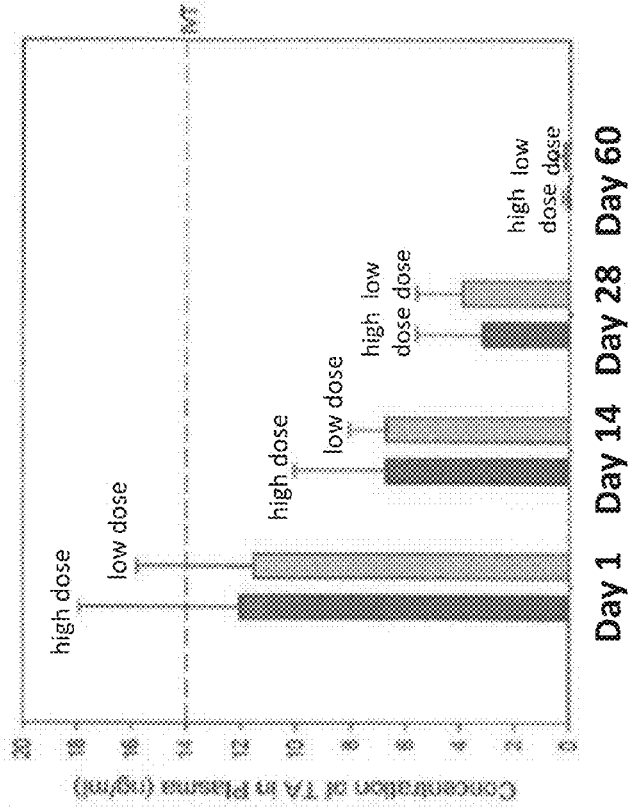

Rabbit Uveitis Model: Detailed Scores

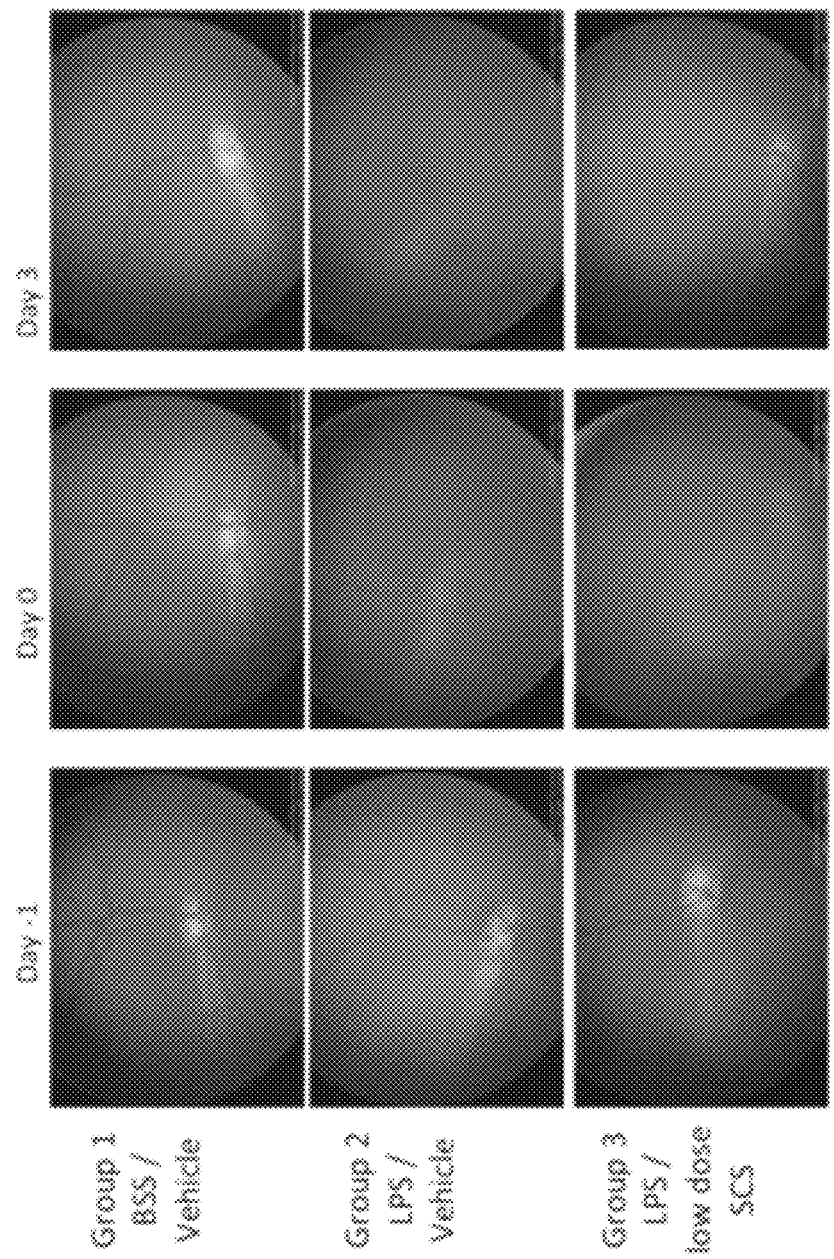

FIG. 30

METHODS AND DEVICES FOR THE TREATMENT OF OCULAR DISEASES IN HUMAN SUBJECTS

CROSS REFERENCE TO RELATED APPLICATIONS

This application is a continuation of U.S. patent application Ser. No. 15/454,636, filed on Mar. 9, 2017, which is a continuation of U.S. patent application Ser. No. 14/441,151, filed May 6, 2015, which is a 371 National Stage application based on PCT Application PCT/US2013/069156, which claims priority from U.S. Provisional Application Ser. No. 61/724,144, filed Nov. 8, 2012; 61/734,872, filed Dec. 7, 2012; 61/745,237, filed Dec. 21, 2012; 61/773,124, filed Mar. 5, 2013; 61/785,229, filed Mar. 14, 2013; 61/819,388, filed May 3, 2013; 61/873,660, filed Sep. 4, 2013, and 61/898,926, filed Nov. 1, 2013, all of which are incorporated herein by reference in their entireties for all purposes.

BACKGROUND OF THE INVENTION

This invention is generally in the field of ophthalmic therapies, and more particularly to the use of a microneedle for infusion of a fluid drug formulation into ocular tissues for targeted, local drug delivery.

The delivery of drug to the eye is extremely difficult, particularly delivery of macromolecules and delivery to the posterior segment. Many inflammatory and proliferative diseases in the posterior region of the eye require long term pharmacological treatment. Examples of such diseases include macular degeneration, diabetic retinopathy, and uveitis. In addition, many choroidal maladies that are associated with inflammatory responses, proliferation, and neovascularization require long term pharmacological treatment. It is difficult to deliver effective doses of drug to the posterior segment using conventional delivery methods such as topical application, which has poor efficacy, and systemic administration, which often causes significant side effects, and often does not reach the site of infection. (Geroski & Edelhauser, *Invest. Ophthalmol. Vis. Sci.* 41:961-64 (2000)). For example, while eye drops are useful in treating conditions affecting the exterior surface of the eye or tissue(s) at the front of the eye, the eye drops cannot significantly penetrate the eye, as may be required for the treatment of various retinal diseases and choroidal maladies.

Direct injection into the eye, using conventional needles and syringes has been reported to be effective, but requires professional training and raises concerns about safety (Maurice, *J. Ocul. Pharmacol. Ther.* 17:393-401 (2001)). It also would be desirable to be able to minimize the number and/or frequency of eye injection treatments needed to deliver therapeutically effective amounts of drug to the ocular tissue sites that need it.

The suprachoroidal space (SCS) of the eye has been studied, and its cannulation described as a possible route for drug delivery. See, e.g., Olsen, et al., *American J. Ophthalmology* 142(5): 777-87 (November 2006); PCT Patent Application Publication No. WO 2007/100745.

It therefore would be desirable to provide better, safer, more effective techniques for the direct delivery of therapeutic agents to posterior segment eye tissues, for example, to treat a posterior ocular disorder. It further would be desirable to provide better, safer, more effective techniques for the direct delivery of therapeutic agents to the SCS for the treatment of choroidal maladies, for example, choroidal maladies associated with vascular abnormalities. The present invention addresses these and other needs.

SUMMARY OF THE INVENTION

In one aspect, the present invention relates to non-surgical ophthalmic therapies in human patients in need of such treatment, and more particularly to the infusion of a drug formulation into the suprachoroidal space of the eye for targeted, local drug delivery, for the treatment of posterior ocular disorders, choroidal maladies and other diseases associated with vascular abnormalities.

In one aspect of the invention, a method is provided for treating a posterior ocular disorder in a human subject in need of treatment. In one embodiment, the method comprises non-surgically administering an effective amount of a drug formulation to the suprachoroidal space (SCS) of the eye of the subject in need of treatment of the posterior ocular disorder or choroidal malady. In a further embodiment, upon administration, the drug formulation flows away from the insertion site and is substantially localized to the posterior segment of the eye. In one embodiment, the posterior ocular disorder is an ocular inflammatory condition such as uveitis, scleritis, glaucoma, ocular sarcoidosis, optic neuritis, macular edema, diabetic retinopathy, macular degeneration, a corneal ulcer, an autoimmune disorder, ophthalmic manifestations of AIDS, optic nerve degeneration, geographic atrophy, choroidal disease or retinitis. The condition in one embodiment is acute. In another embodiment, the condition is chronic.

In another embodiment, the a method is provided for the treatment of a choroidal malady, e.g., ocular neovascularization, polypoidal choroidal vasculopathy, choroidal sclerosis, central sirrus choroidopathy, a multi-focal choroidopathy or a choroidal dystrophy (e.g., central gyrate choroidal dystrophy, serpiginous choroidal dystrophy, total central choroidal atrophy). In one embodiment, the method comprises non-surgically administering a drug formulation comprising an effective amount of an anti-inflammatory drug, a vascular endothelial growth factor (VEGF) modulator, a platelet derived growth factor (PDGF) modulator, an angiogenesis inhibitor, an immunosuppressive agent, a vascular permeability inhibitor, or a combination thereof, to the SCS of the patient in need of treatment. In a further embodiment, the effective amount of the drug administered to the SCS provides higher efficacy or a greater therapeutic effect of the drug, compared to the identical drug dose administered intravitreally, intracamerally, topically, parenterally or orally. In even a further embodiment, the patient undergoing treatment via SCS drug therapy was not previously responsive to a different type of therapy for the same condition.

In yet another embodiment, a method for decreasing subretinal exudation and bleeding in a subject is provided. In a further embodiment, the method comprises non-surgically administering a drug formulation comprising an effective amount of an effective amount of an anti-inflammatory drug, a vascular endothelial growth factor (VEGF) modulator, a platelet derived growth factor (PDGF) modulator, an angiogenesis inhibitor, an immunosuppressive agent, a vascular permeability inhibitor, or a combination thereof, to the SCS of the patient in need of treatment, wherein administration of the drug formulation reduces subretinal exudation and bleeding experienced by the patient, as compared to the identical dosage of the drug administered intravitreally to the patient.

In one embodiment, a method for treating a posterior ocular disorder or a choroidal malady in a human patient is provided. In a further embodiment, the method comprises non-surgically administering an effective amount of a drug formulation to the suprachoroidal space (SCS) of the eye of the subject in need of treatment of the posterior ocular disorder or choroidal malady. In a further embodiment, the intraocular elimination half life ($t_{1/2}$) of the drug administered to the SCS is greater than the intraocular $t_{1/2}$ of the drug, when administered intravitreally, intracamerally, topically, parenterally or orally. In another embodiment, the mean intraocular maximum concentration ($C_{max}$) of the drug, when administered to the SCS via the methods described herein, is greater than the intraocular $C_{max}$ of the drug, when administered intravitreally, intracamerally, topically, parenterally or orally. In another embodiment, the mean intraocular area under the curve ($AUC_{0-t}$) of the drug, when administered to the SCS via the methods described herein, is greater than the intraocular $AUC_{0-t}$ of the drug, when administered intravitreally, intracamerally, topically, parenterally or orally. In yet another embodiment, the intraocular time to peak concentration ($t_{max}$) of the drug, when administered to the SCS via the methods described herein, is greater than the intraocular $t_{max}$ of the drug, when the same drug dose is administered intravitreally, intracamerally, topically, parenterally or orally. In a further embodiment, the drug formulation comprises an effective amount of an anti-inflammatory drug (e.g., a steroid or NSAID), a VEGF modulator (e.g., VEGF antagonist), a platelet derived growth factor (PDGF) modulator, an angiogenesis inhibitor, an immunosuppressive agent, a vascular permeability inhibitor, or a combination thereof.

In one embodiment, the method for treating a posterior ocular disorder or choroidal malady in a human subject comprises delivering a drug formulation via a hollow microneedle to the SCS of the eye of the human subject in need of treatment. In a further embodiment, delivering the drug formulation comprises inserting a hollow microneedle into the eye of the human subject at an insertion site, the microneedle having a tip end with an opening; and infusing over a period of time a drug formulation through the inserted microneedle and into the SCS space away from the insertion site. The drug formulation administered to the SCS, in one embodiment, flows away from the insertion site and is substantially localized to the posterior segment of the eye, thereby increasing the therapeutic efficacy of the dose of the drug compared to the therapeutic efficacy of the same drug dose administered by another means (e.g. intravitreally, intracamerally, topically, parenterally, and/or orally). In another embodiment, the dose of the drug sufficient to elicit a therapeutic response when administered to the SCS is less than the dosage of the drug sufficient to elicit a therapeutic response when administered intravitreally, topically, parenterally or orally. In another embodiment, the drug formulation is delivered to the SCS by a hollow microneedle inserted into the sclera at the equator of the eye or between the equator and the limbus of the eye. In a further embodiment, the hollow microneedle is inserted in the insertion site at a 90 degree angle (perpendicular).

The drug formulation delivered by the methods described herein, in one embodiment, comprises an effective amount of an anti-inflammatory drug, for example a steroid or a non-steroidal anti-inflammatory drug (NSAID). In another embodiment, the drug delivered to the SCS via the methods described herein is a steroid, immunosuppressive, antimetabolite, T-cell inhibitor, alkylating agent, biologic, TNFα antagonist, interleukin antagonist, neuroprotectant, vascular endothelial growth factor (VEGF) antagonist, platelet derived growth factor (PDGF) antagonist, or a combination thereof. In another embodiment, the drug affects inflammation, neuroprotection, complement inhibition, drusen formation, scar formation, reduction in choriocapillaris or choroidal neocasvularization. In another embodiment, the drug formulation comprises microparticles and/or nanoparticles of the drug. In one embodiment, the drug formulation comprises microparticles having a $D_{50}$ of 1 µm or less and/or a $D_{99}$ of 10 µm or less.

As provided above, one aspect of the invention includes a method for treating a posterior ocular disorder in a human subject in need thereof comprising non-surgically administering a drug formulation to the SCS of the eye of the human subject, wherein upon administration, the drug formulation flows away from the insertion site and is substantially localized to the posterior segment. In one embodiment of the method, the intraocular pressure of the eye remains substantially constant during administration of the drug formulation to the SCS. In another embodiment, administration of the drug formulation to the SCS of the eye results in a decreased number of side effects, or a reduced severity of one or more side effects, compared to administration of the same drug dose intravitreally, intracamerally, topically, orally or parenterally.

In one aspect of the invention, the present invention relates to a method for treating a choroidal malady in a human patient in need of treatment. In one embodiment, the method comprises non-surgically administering a drug formulation comprising an effective amount of an anti-inflammatory drug, a vascular endothelial growth factor (VEGF) modulator, a platelet derived growth factor (PDGF) modulator, an angiogenesis inhibitor, an immunosuppressive agent or a vascular permeability inhibitor, to the suprachoroidal space (SCS) of the eye of the patient. In a further embodiment, the human patient, prior to administration of the drug formulation, was previously treated for the choroidal malady and was not properly responsive to the treatment.

In another aspect of the invention, the present invention relates to a method for treating ocular neovascularization in a human patient in need of treatment. In one embodiment, the method comprises non-surgically administering a drug formulation comprising an effective amount of an anti-inflammatory drug, a vascular endothelial growth factor (VEGF) modulator (e.g., a VEGF antagonist), a platelet derived growth factor (PDGF) modulator (e.g., a PDGF antagonist), an angiogenesis inhibitor, an immunosuppressive agent or a vascular permeability inhibitor, to the suprachoroidal space (SCS) of the eye of the patient. In a further embodiment, the ocular neovascularization is a choroidal neovascularization. In one embodiment, the human patient being treated for the ocular neovascularization, prior to administration of the drug formulation, was previously treated for the ocular neovascularization and was not properly responsive to the treatment.

The drug formulation delivered by the methods described herein, in one embodiment, comprises an effective amount of an anti-inflammatory drug, for example a steroidal compound or a non-steroidal anti-inflammatory drug (NSAID). In another embodiment, the drug delivered to the SCS via the methods described herein is a vascular permeability inhibitor, an angiogenesis inhibitor or a VEGF modulator, e.g., a VEGF antagonist. In one embodiment, the VEGF antagonist is a VEGF receptor antagonist or a soluble VEGF receptor. In one embodiment, the drug formulation comprises drug microparticles having a $D_{50}$ of 1 µm or less and/or a $D_{99}$ of 10 µm or less. In a further embodiment, the drug formulation comprises triamcinolone.

In one embodiment of the invention, a method for treating a choroidal malady or a posterior ocular disorder in a human subject in need thereof is provided comprising non-surgically administering a drug formulation to the SCS of the eye of the human subject, wherein, the intraocular pressure of the eye remains substantially constant during administration of the drug formulation to the SCS. In another embodiment, administration of the drug formulation to the SCS of the eye of the patient in need of treatment of the posterior ocular disorder or choroidal malady results in a decreased number of side effects, or a reduced severity of one or more side effects, compared to administration of the same drug dose intravitreally, intracamerally, topically, orally or parenterally. In one embodiment, the side effect reduced by the methods described herein is subretinal exudation and/or bleeding.

BRIEF DESCRIPTION OF THE DRAWINGS

FIGS. 1A, 1B, 1C, and 1D are cross-sectional illustrations of the tissue structures of a human eye. The eye as a whole (A), a close-up of the cornea (1B), and a close-up of the sclera and associated tissue in an eye without fluid in the suprachoroidal space (1C) or with fluid in the suprachoroidal space (1D).

FIG. 4 is an illustration of a microneedle device according to one embodiment.

FIG. 5 is an illustration of a microneedle device according to one embodiment.

FIG. 18 is a block diagram of a method for administering a drug to the eye according to one embodiment.

FIG. 19C, bottom, is a graph showing the ratio of the amount of TA in the lens of the eye to the amount of TA in the back of the eye (retina) as a function of time after administration (days).

FIG. 20B is a cross sectional image of a rabbit eye following suprachoroidal injection of 3.2 mg triamcinolone (left) or vehicle (right).

FIG. 20C are graphs showing the TA plasma concentration (ng/mL) after administration of TA to the SCS of rabbit eye, as a function of time after TA administration.

Figure 21A:
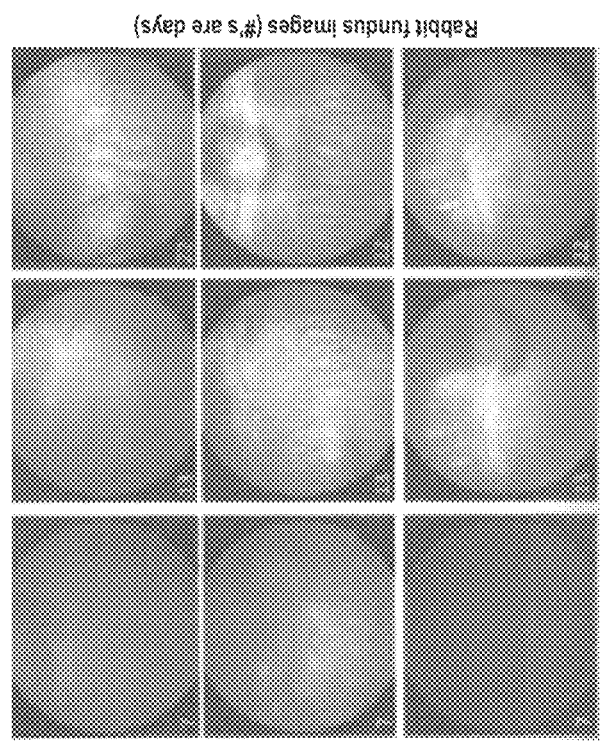
FIG. 21A is a graph showing the cumulative McDonald-Shadduck scores of eyes treated with vehicle (left), 4 mg triamcinolone (TA) administered to the SCS (middle) or 4 mg triamcinolone administered intravitreally (right), as a function of time after treatment, and time after LPS toxin administration. The McDonald-Shadduck scores provide a model of posterior uveitis.
Figure 21B:
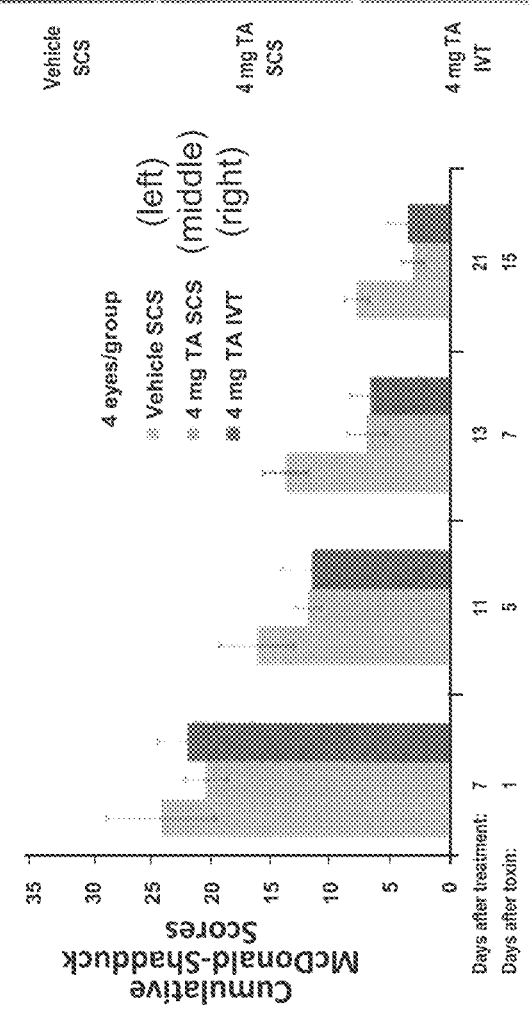

FIG. 21B are representative fundus photographs showing the effect of triamcinolone (TA) administered to the SCS or intravitreally in a model of posterior uveitis in NZW rabbits.

Figure 21D:
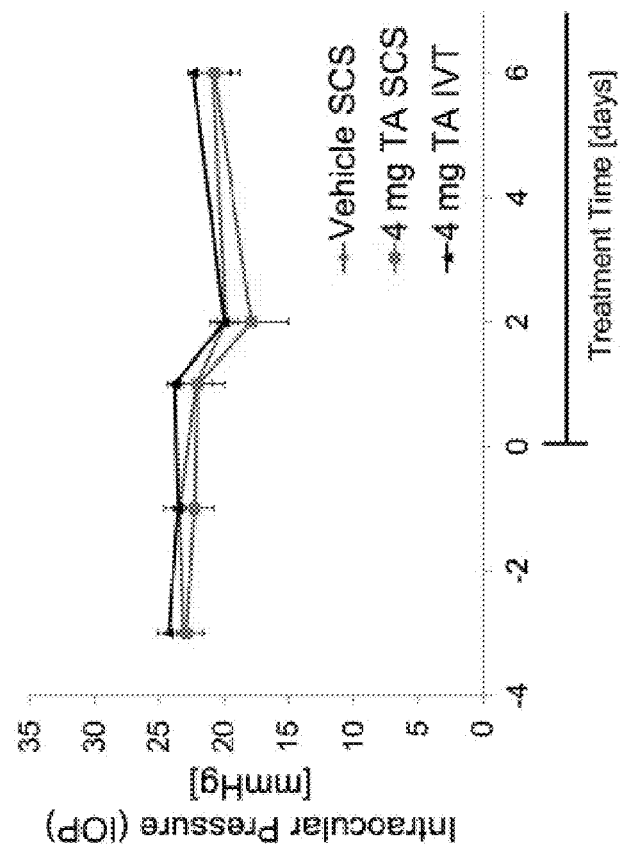
Figure 21C:
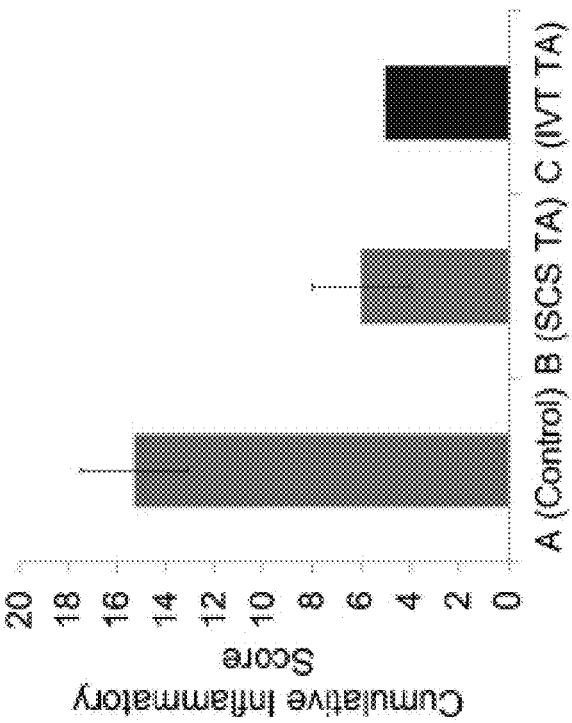

FIG. 21C is a graph showing the overall severity of inflammation in NZW rabbits as measured from histology at the final time point. The following tissues were analyzed: ciliary processes, sclera-choroid, vitreous, retina and optic nerve (0-4 scale, max score=20).

FIG. 21D is a graph showing the intraocular pressure (mmGh) in NZW rabbits in response to IVT or SCS TA administration.

Figure 22A:
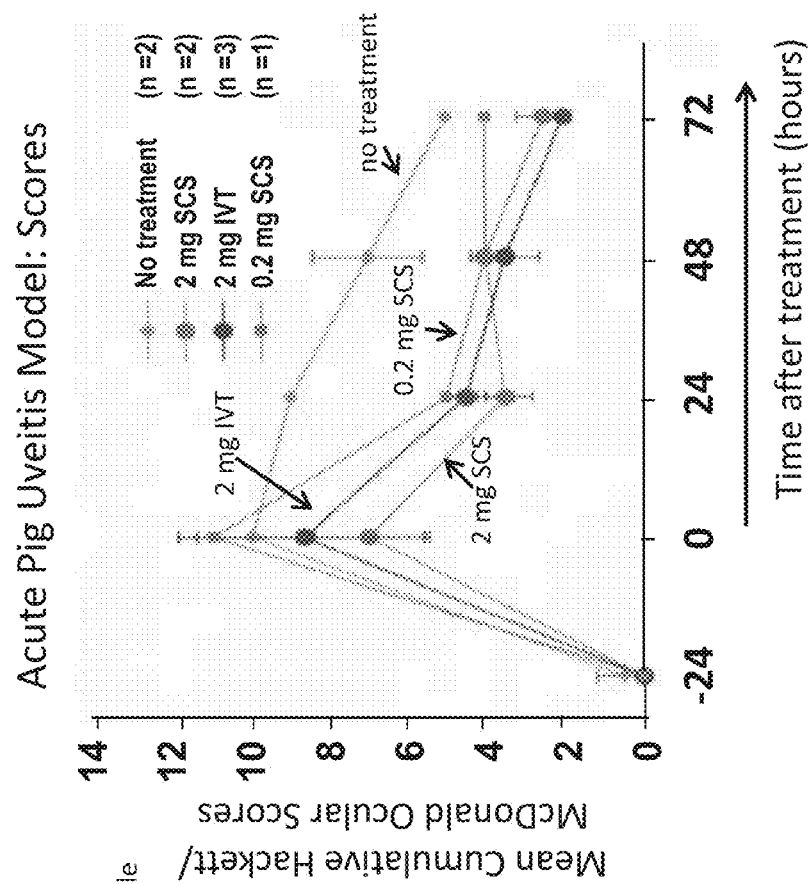

FIG. 22A is a graph showing the mean Hackett/McDonald ocular scores of porcine eyes challenged with (i) lipopolysaccharide (LPS) toxin followed by vehicle (left), (ii) LPS toxin followed by 2 mg triamcinolone to the SCS (middle), or (iii) balanced salt solution followed by vehicle. Treatment with SCS TA at a dose of 2 mg significantly reduces the ocular inflammatory response in this porcine uveitis model.

Figure 22B:
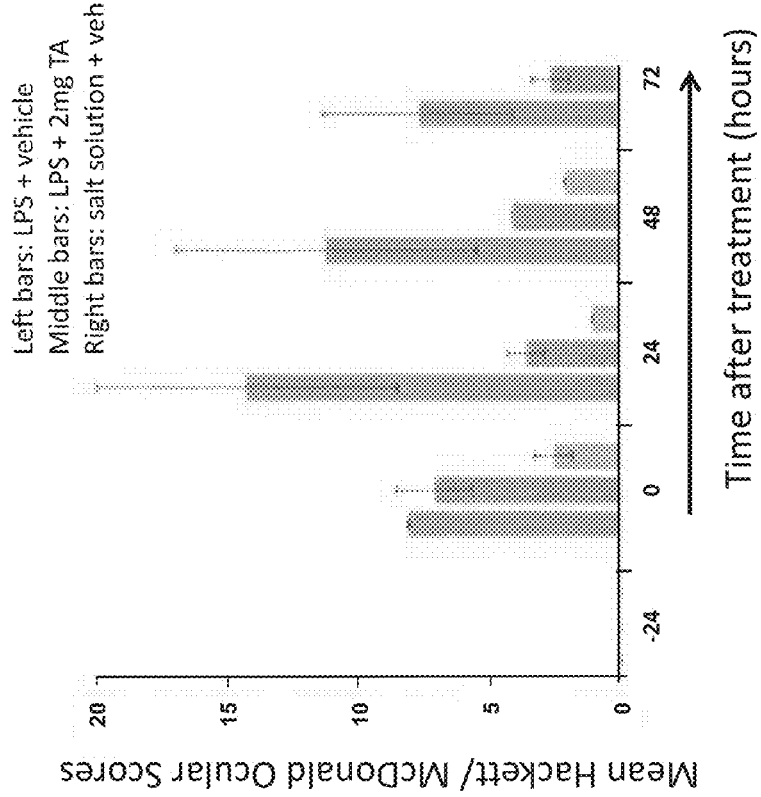

FIG. 22B is a graph showing the mean cumulative Hackett/McDonald ocular scores of porcine eyes challenged with (i) lipopolysaccharide (LPS) toxin followed by vehicle, (ii) LPS toxin followed by 2 mg triamcinolone (TA) to the SCS, (iii) LPS toxin followed by 2 mg triamcinolone intravitreally, or (iv) LPS toxin followed by 0.2 mg triamcinolone to the SCS. A reduction in inflammation was observed within 3 days with a dose of TA administered to the SCS that was 10% of the dose of TA required when administered intravitreally.

Figure 23:
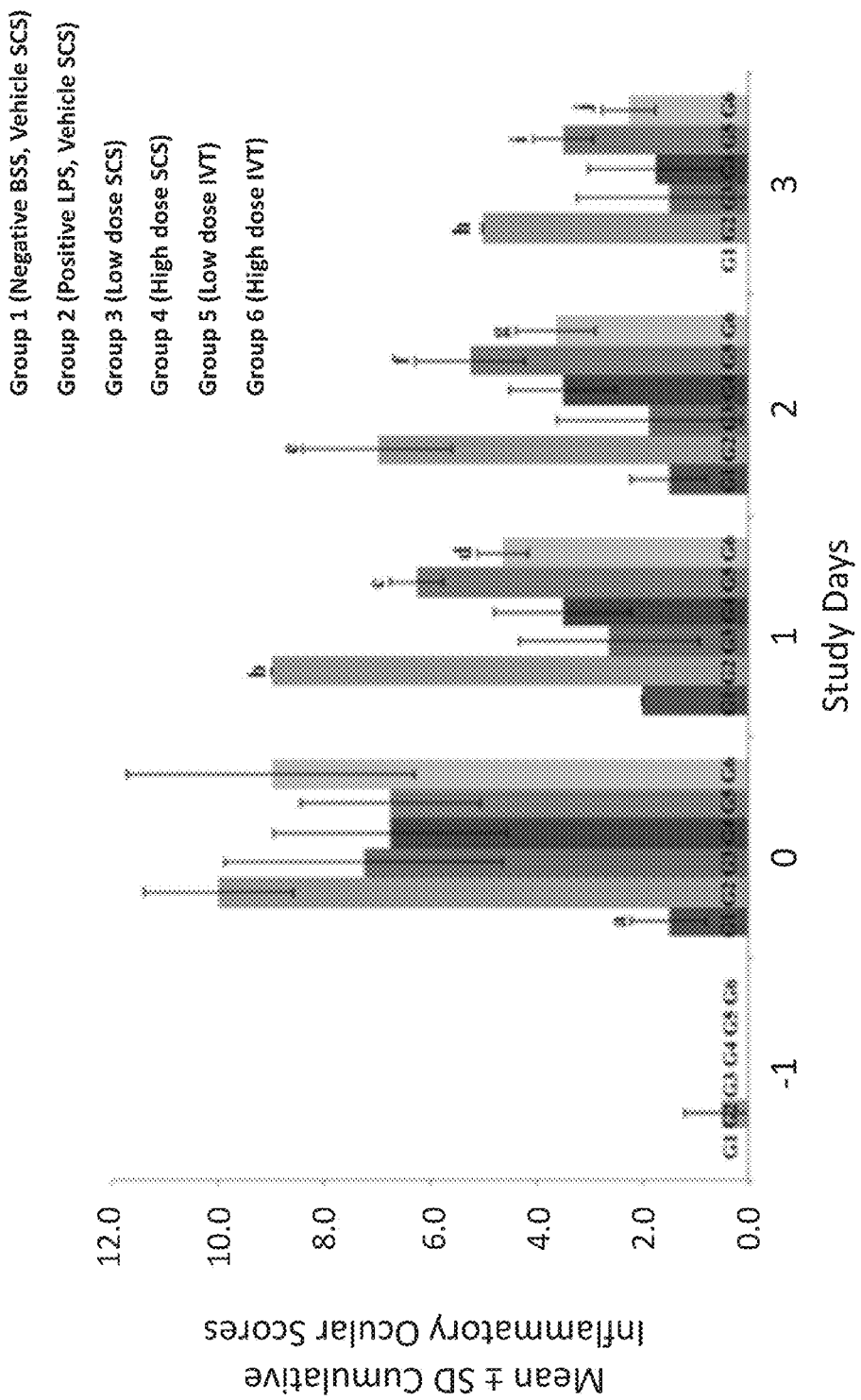

FIG. 23 is a graph showing the mean (±standard deviation) cumulative inflammatory ocular score of animals dosed with or without toxin, and then treated with low or high doses of TA administered either to the SCS or intravitreally. The mean inflammatory scores of eyes treated with SCS TA were lower than the scores of eyes treated with IVT TA one, two and three days after treatment.

Mean (+/−SD) cumulative inflammatory ocular scores at uveitis induction (i.e., toxin administration) (Day −1), at time of drug administration (Day 0). Eyes were administered suprachoroidal space (SCS) or intravitreal (IVT) injections of 0.2 mg (low dose) or 2.0 mg (high dose) of triamcinolone acetonide (TA), and ocular scores were calculated 1, 2, and 3 days after treatment. Group 1 mean cumulative inflammatory scores were significantly lower than Groups 2 through 6 at Day 0 (Wilcoxon; P<0.028); b. Group 2 mean cumulative inflammatory scores were significantly higher than Groups 1 and 3, 4, 5, and 6 at Day 1 (Wilcoxon; P<0.028); c. Group 5 mean cumulative inflammatory scores were significantly higher than Groups 1, 3, 4, and 6 at Day 1 (Wilcoxon; P<0.029); d. Group 6 mean cumulative inflammatory scores were significantly higher than Group 1 at Day 1 (Wilcoxon; P=0.02); e. Group 2 mean cumulative inflammatory scores were significantly higher than Groups 1, 3, 4, and 6 at Day 2 (Wilcoxon; P<0.028); f. Group 5 mean cumulative inflammatory scores were significantly higher than Groups 1 and 3 at Day 2 (Wilcoxon; P<0.042); g. Group 6 mean cumulative inflammatory scores were significantly higher than Group 1 at Day 2 (Wilcoxon; P=0.028); h. Group 2 mean cumulative inflammatory scores were significantly higher than Groups 1, 3, 4, 5, and 6 at Day 3 (Wilcoxon; P<0.02); i. Group 5 mean cumulative inflammatory scores were significantly higher than Groups 1 and 6 at Day 3 (Wilcoxon; P<0.047); j. Group 6 mean cumulative inflammatory scores were significantly higher than Group 1 at Day 3 (Wilcoxon; P=0.018). G1=Group 1; G2=Group 2; G3=Group 3; G4=Group 4; G5=Group 5; G6=Group 6.

Figure 24:
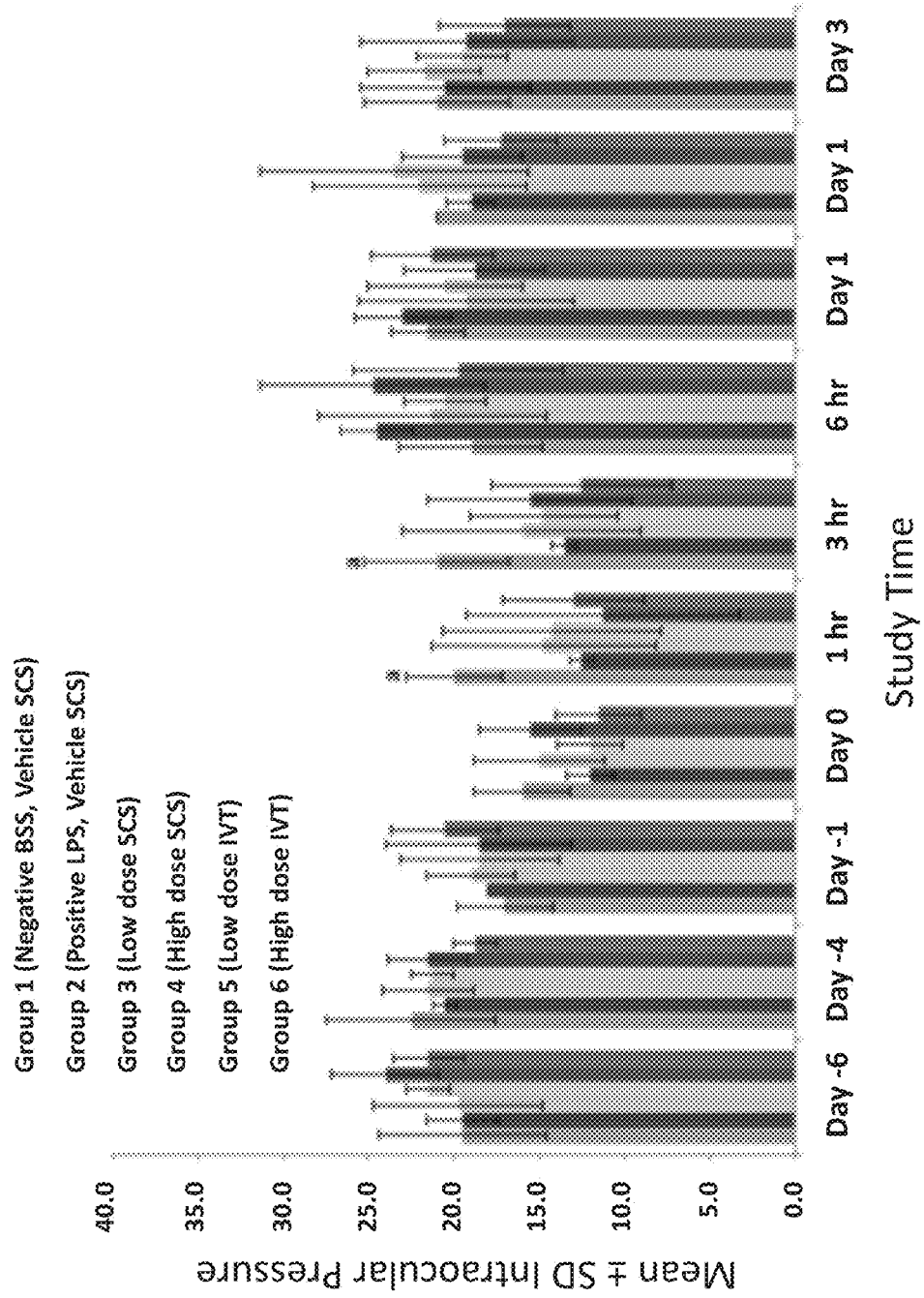

FIG. 24 is a graph showing the mean intraocular pressure in the eye of animals dosed with or without a toxin on Day −1 and then treated with low or high doses of TA administered either to the SCS or intravitreally on Day 0. Mean (+/−SD) intraocular pressure (TOP) in porcine eyes prior to uveitis induction (Day −1), at the time of drug administration (Day 0) with suprachoroidal space (SCS) or intravitreal (IVT) injections of 0.2 mg (low dose) or 2.0 mg (high dose) triamcinolone acetonide (TA). IOP was measured 1 hr., 3 hr., 6 hr. 1 day, 2 days and 3 days after treatment. a. IOP in Group 1 eyes was significantly higher than Group 2 eyes at 1 and 3 hours after treatment injections (P=0.01; 0.04).

Figure 25B:
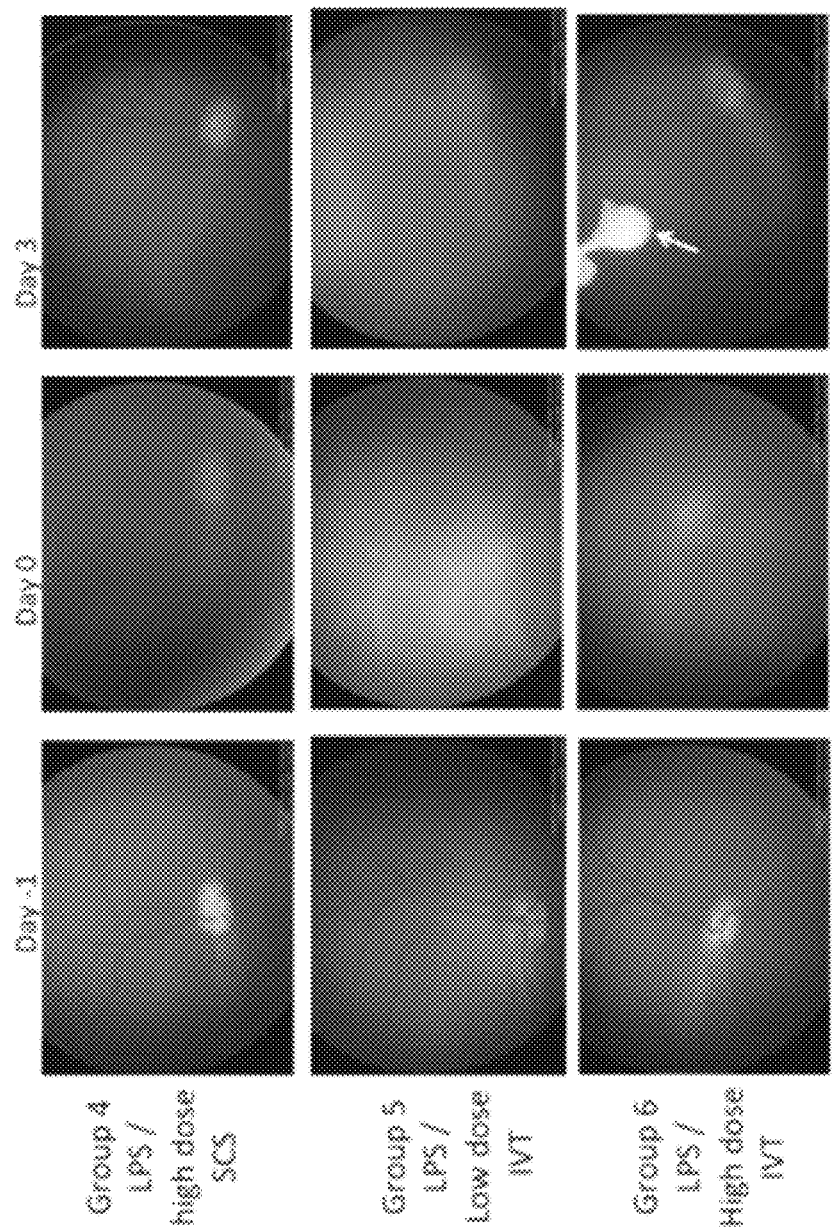

FIGS. 25A-B are wide-field ocular fundus images of eyes from animals dosed with or without a toxin and then treated with low or high doses of TA administered either to the SCS or intravitreally. Wide-field ocular fundus images were imaged at immediately prior to injection with liopolysaccharide (LPS) on Day −1, immediately prior to injection with vehicle, 0.2 mg (low dose) or 2.0 mg (high dose) of trimacinolone acetonide on Day 0, and at 3 days after treatment. Group 1 eyes, which were injected with balanced salt solution and vehicle, remained normal in appearance. Substantial cloudiness of the ocular posterior segment developed 24 hours after LPS injection in all eyes except in Group 1 eyes. Treatment with low and high dose mg TA into the SCS and high dose TA IVT resulted in fundus images near pre-treatment appearance, while treatment with low dose TA IVT resulted in images only slightly improved over vehicle treated eyes. Eyes with 2.0 mg TA IVT injections had a solid large depot of TA (Arrow) visible in the central vitreous.

Figure 26:
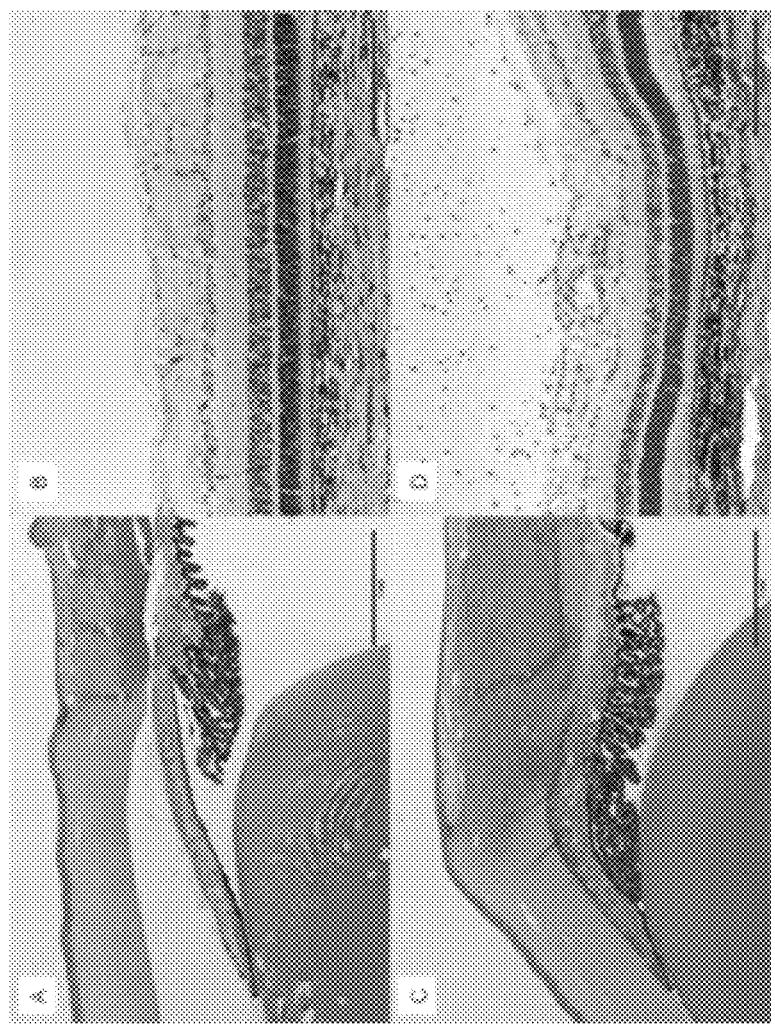
Figure 26:
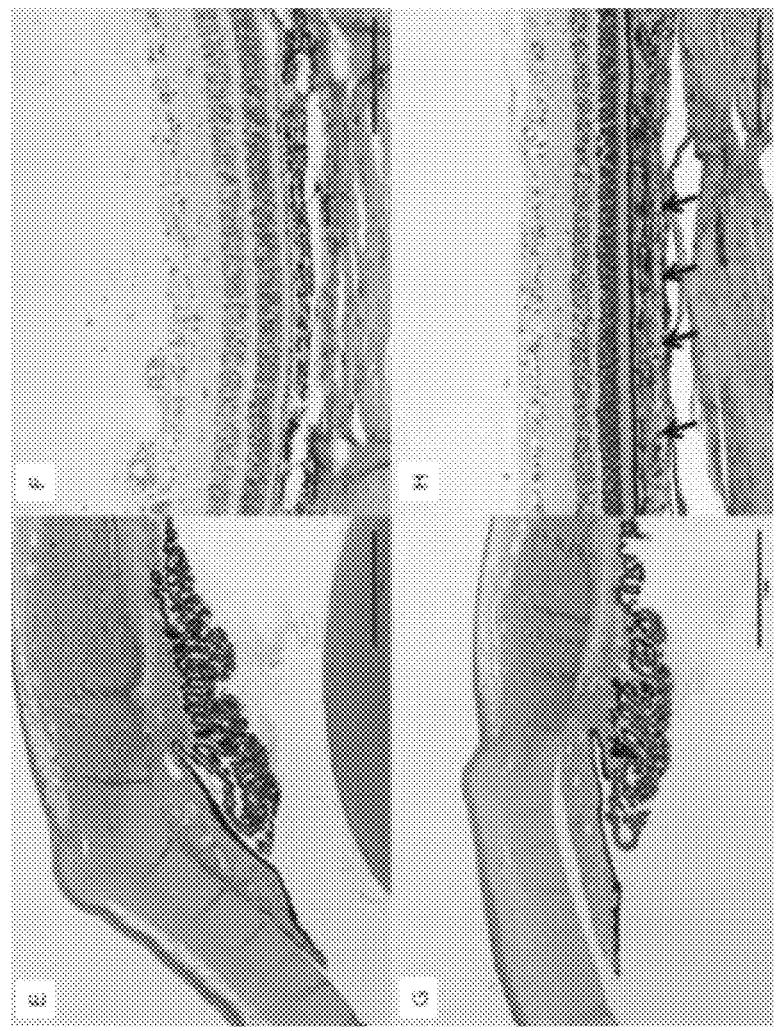
Figure 26:
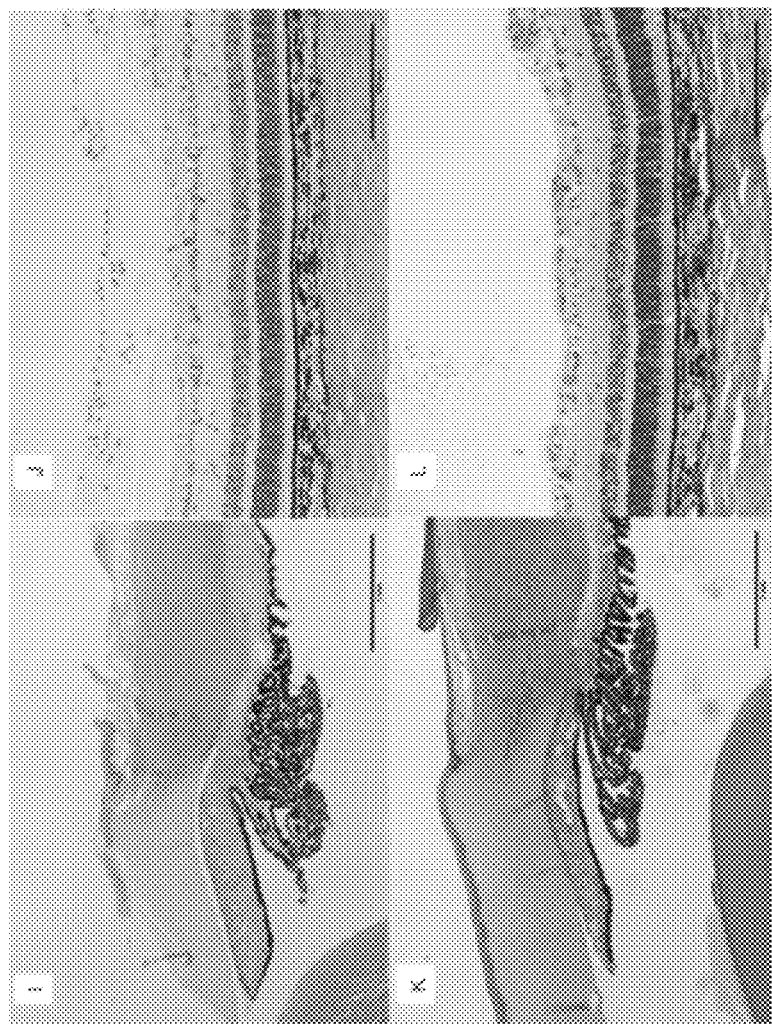

FIG. 26 show the ocular histopathology of eyes three days after intravitreal injection of balances salt solution (BSS) or 100 ng of lipopolysaccharide (LPS) and 72 hours after SCS or IVT administration of vehicle, 0.2 mg TA, or 2.0 mg TA. None of the eyes examined had evidence of substantial tissue, structural, or toxicologic changes on histopathology. Ocular histopathology of eyes 3 days after intravitreal (IVT) injection of balanced salt solution (BSS) or 100 ng of lipopolysaccharide (LPS) and 72 hours after suprachoroidal (SCS) or IVT injection of vehicle, 0.2 mg triamcinolone acetonide (low dose TA), or 2.0 mg of triamcinolone acetonide (high dose TA). Hematoxylin and eosin stain.
A. Anterior segment of eyes injected with BSS IVT and vehicle in SCS (Group 1). Scale bar: 1 mm.
B. Posterior segment of eyes injected with BSS IVT and vehicle in SCS (Group 1). Scale bar: 200 μm.
C. Anterior segment of eyes injected with LPS IVT and vehicle in SCS (Group 2). Scale bar: 1 mm.
D. Posterior segment of eyes injected with LPS IVT and vehicle in SCS (Group 2). Scale bar: 200 μm.
E. Anterior segment of eyes injected with LPS IVT and low dose TA in SCS (Group 3). Scale bar: 1 mm.
F. Posterior segment of eyes injected with LPS IVT and low dose TA in SCS (Group 3). Scale bar: 200 μm.
G. Anterior segment of eyes injected with LPS IVT and high dose TA in SCS (Group 4). Scale bar: 1 mm.
H. Posterior segment of eyes injected with LPS IVT and high dose TA in SCS (Group 4). Arrows indicate presence of TA in SCS. Scale bar: 200 μm.
I. Anterior segment of eyes injected with LPS IVT and low dose TA IVT (Group 5). Scale bar: 1 mm.
J. Posterior segment of eyes injected with LPS IVT and low dose TA IVT (Group 5). Scale bar: 200 μm.

K. Anterior segment of eyes injected with LPS IVT and high dose TA IVT (Group 6). Scale bar: 1 mm.

L. Posterior segment of eyes injected with LPS IVT and high dose TA IVT (Group 6). Scale bar: 200 μm.

Figure 27:
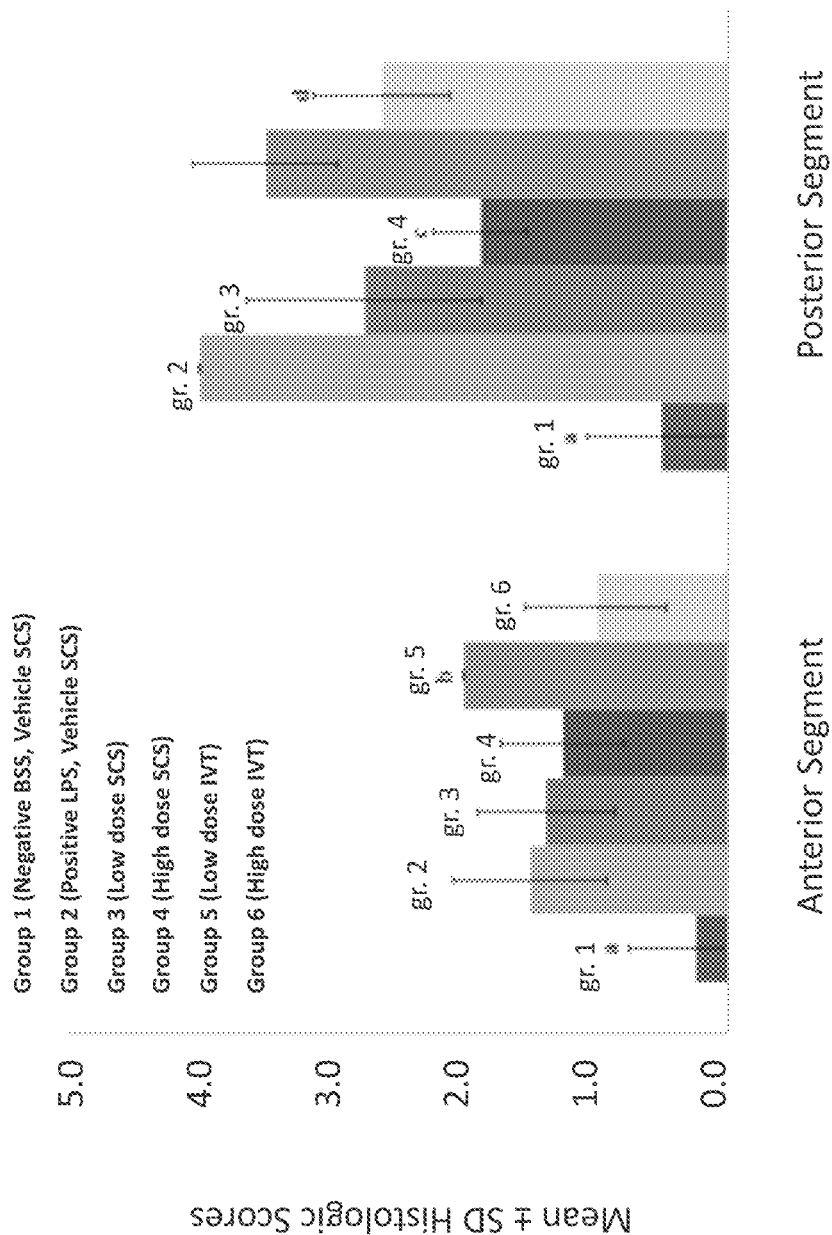

FIG. 27 shows the mean ocular histopathologic inflammatory scores of the anterior and posterior segments 4 days after intravitreal (IVT) injection of balanced salt solution (BSS) or 100 ng of lipopolysaccharide (LPS) and 3 days after suprachoroidal (SCS) or IVT injection of vehicle, 0.2 mg triamcinolone acetonide (low dose TA), or 2.0 mg of triamcinolone acetonide (high dose TA). a. Group 1 mean histologic inflammatory scores were significantly lower than Groups 2 through 6 ($P<0.04$). b. Group 5 mean histologic inflammatory scores were significantly higher than Groups 4 and 6 ($P<0.04$). c. Group 4 mean histologic inflammatory scores were significantly lower than Groups 2, 5, and 6 ($P<0.04$). d. Group 6 mean histologic inflammatory score are significantly lower than Group 2 ($P=0.018$).

Figure 28:
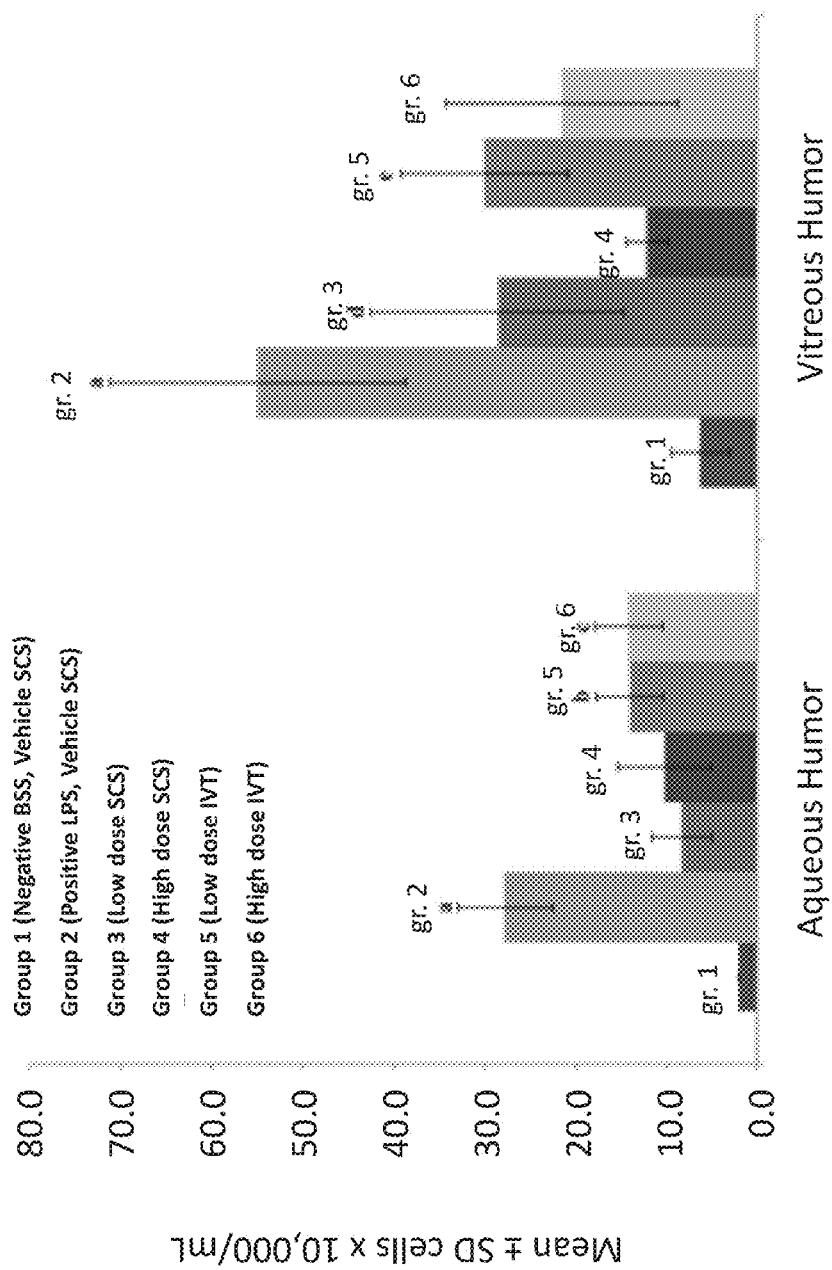

FIG. 28 shows the mean aqueous humor (AH) and vitreous humor (VH) cell counts 3 days after intravitreal (IVT) injection of balanced salt solution (BSS) or 100 ng of lipopolysaccharide (LPS) and 72 hours after suprachoroidal (SCS) or IVT injection of vehicle, 0.2 mg triamcinolone acetonide (low dose TA), or 2.0 mg of triamcinolone acetonide (high dose TA). a. Group 2 mean cell counts were significantly higher than Groups 1, 3, 4, 5, and 6 ($P<0.002$). b. Group 5 mean cell counts were significantly higher than Group 1 ($P<0.002$). c. Group 6 mean cell counts were significantly higher than Group 1 ($P<0.002$). d. Group 3 mean cell counts were significantly higher than Groups 1 and 4 ($P<0.048$). e. Group 5 mean cell counts were significantly higher than Groups 1 and 4 ($P<0.034$).

Figure 29:
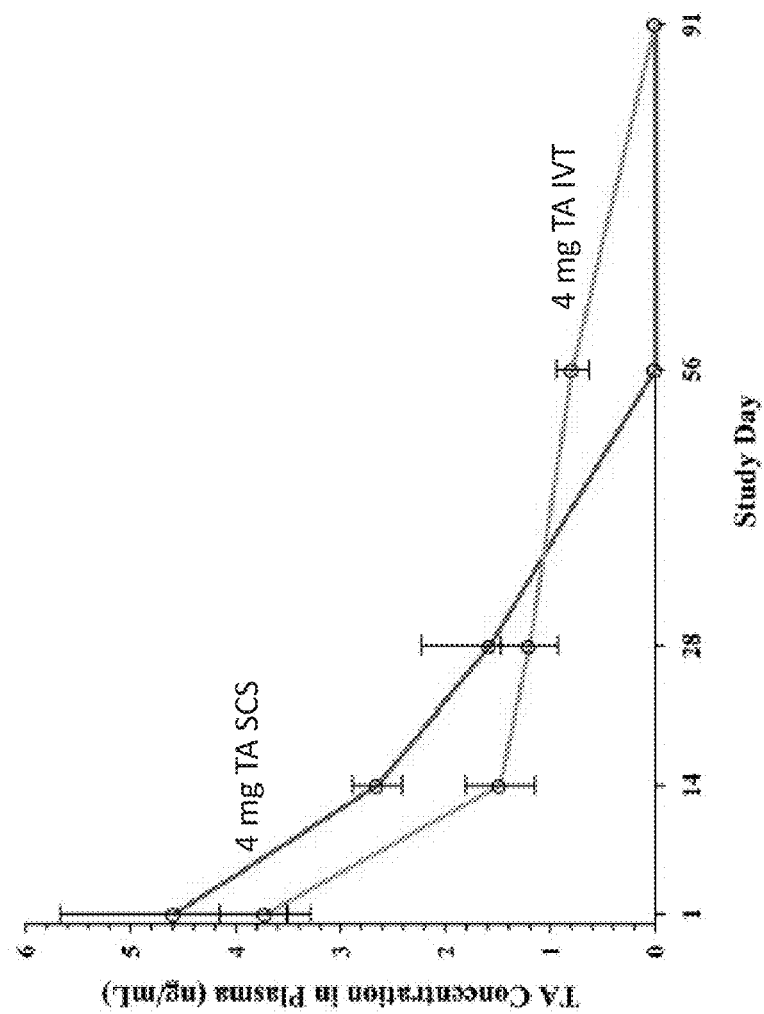

FIG. 29 is a graph showing triamcinolone (TA) concentration in plasma after either SCS or IVT administration.

FIG. 30 are optical Coherence tomography (OCT) images of patient number 3 before injection (left image) and 56 days after injection (right image) of bevacizumab into the suprachoroidal space. Decrease in the intraretinal fluid can be observed.

Figure 31:
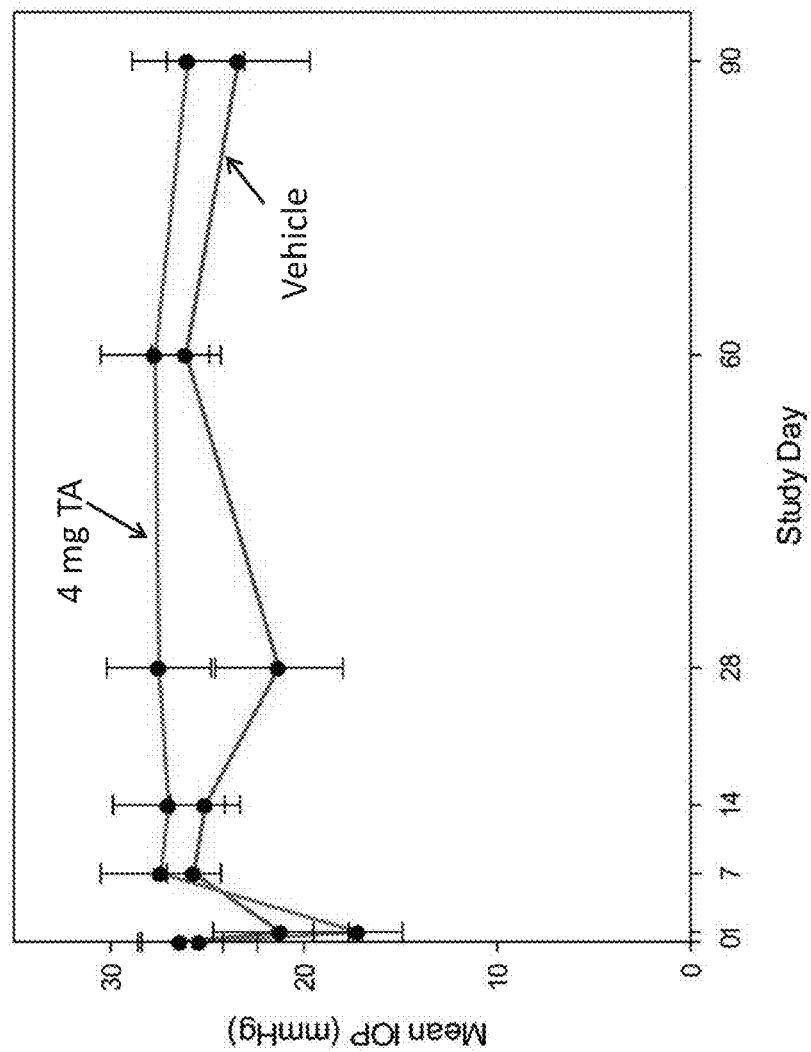

FIG. 31 is a graph showing intraocular pressure (IOP) following SCS administration of 4 mg (40 mg/mL) TA or vehicle.

Figure 32:
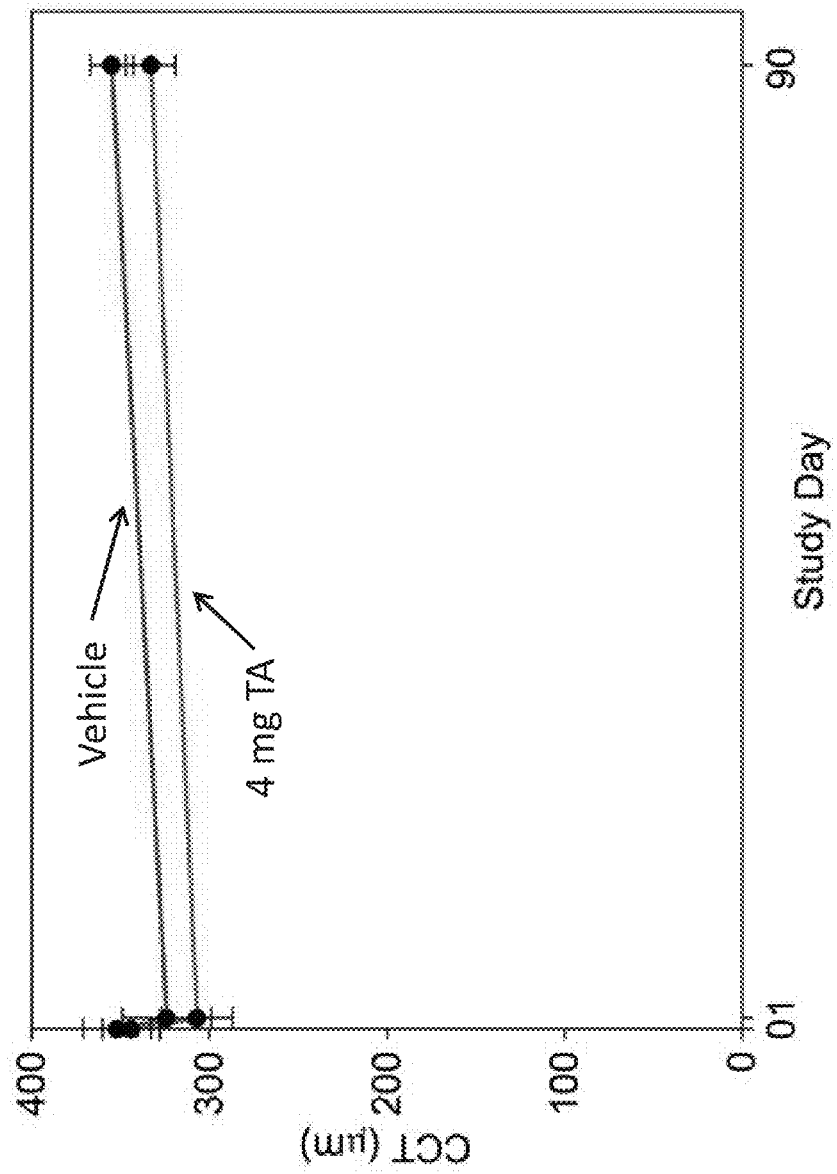

FIG. 32 is a graph showing central corneal thickness on Day 1 and Day 90 following SCS administration of 4 mg (40 mg/mL) TA or vehicle.

Figure 33:
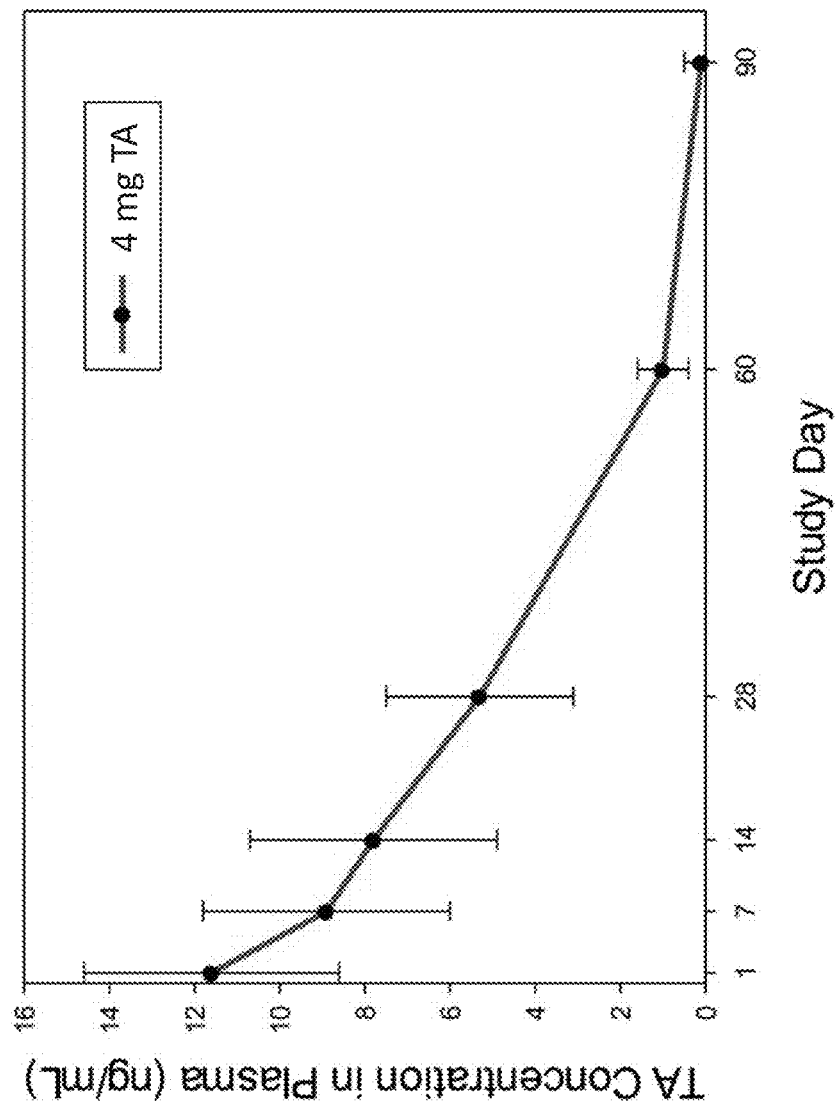

FIG. 33 is a graph showing TA concentration in plasma over time following SCS administration of 4 mg (40 mg/mL) TA.

DETAILED DESCRIPTION OF THE INVENTION

Methods, devices and drug formulations are provided herein for treating posterior ocular disorders and choroidal maladies in human subjects in need thereof. The methods, devices and formulations provided herein allow for effective posterior segment drug delivery to treat posterior ocular disorders and choroidal maladies, and generally embody the following characteristics: (1) the methods are non-surgical and thus minimally invasive and safe; (2) the drug formulations are administered in such a way that they are well targeted to the posterior segment of the eye and/or the suprachoroidal space (SCS) of the eye while simultaneously limiting drug exposure to the anterior segment or other regions of the eye; (3) the methods and formulations are capable of delivering drug in a sustained and/or controlled manner; (4) the methods and devices are user-friendly. The non-surgical SCS delivery methods, devices for implementing the methods, and drug formulations for SCS delivery set forth herein achieve these desired characteristics.

As used herein, "non-surgical" ocular drug delivery methods refer to methods of drug delivery that do not require general anesthesia and/or retrobulbar anesthesia (also referred to as a retrobulbar block). Alternatively or additionally, a "non-surgical" ocular drug delivery method is performed with an instrument having a diameter of 28 gauge or smaller. Alternatively or additionally, "non-surgical" ocular drug delivery methods do not require a guidance mechanism that is typically required for ocular drug delivery via a shunt or cannula.

The non-surgical posterior ocular disorder and choroidal malady treatment methods described herein are particularly useful for the local delivery of drugs to the posterior region of the eye, for example the retinochoroidal tissue, macula, retinal pigment epithelium (RPE) and optic nerve in the posterior segment of the eye. In another embodiment, the non-surgical methods and microneedles provided herein can be used to target drug delivery to specific posterior ocular tissues or regions within the eye or in neighboring tissue. In one embodiment, the methods described herein deliver drug specifically to the sclera, the choroid, the Brach's membrane, the retinal pigment epithelium, the subretinal space, the retina, the macula, the optic disk, the optic nerve, the ciliary body, the trabecular meshwork, the aqueous humor, the vitreous humor, and/or other ocular tissue or neighboring tissue in the eye of a human subject in need of treatment. The methods and microneedles provided herein, in one embodiment, can be used to target drug delivery to specific posterior ocular tissues or regions within the eye or in neighboring tissue.

In one embodiment of the methods described herein, non-surgical delivery of a drug, e.g., an anti-inflammatory drug (e.g., triamcinolone), a vascular endothelial growth factor (VEGF) modulator (e.g., VEGF antagonist), a platelet derived growth factor (PDGF) antagonist to the suprachoroidal space for treatment of a posterior ocular disorder or choroidal malady, is achieved by inserting a microneedle into the eye of a patient, for example the sclera, and injecting or infusing a drug formulation through the inserted microneedle and into the suprachoroidal space of the eye. In one embodiment, the effective amount of the drug administered to the SCS provides higher therapeutic efficacy of the drug, compared to the therapeutic efficacy of the drug when the identical dosage is administered intravitreally, topically, intracamerally, parenterally or orally. In one embodiment, the microneedle drug delivery methods described herein precisely deliver the drug into the SCS for subsequent local delivery to nearby posterior ocular tissues in need of treatment. The drug may be released into the ocular tissues from the infused volume (or, e.g., from microparticles or nanoparticles in the drug formulation) for an extended period, e.g., several hours or days or weeks or months, after the non-surgical drug administration has been completed. This beneficially can provide increased bioavailability of the drug relative, for example, to delivery by topical application of the drug formulation to ocular tissue surfaces, or increased bioavailability compared to oral, parenteral on intravitreal administration of the same drug dosage.

With the methods and microneedle devices described herein, the SCS drug delivery methods advantageously include precise control of the depth of insertion into the ocular tissue, so that the microneedle tip can be placed into the eye so that the drug formulation flows into the suprachoroidal space and in some embodiments to the posterior ocular tissues surrounding the SCS. In one embodiment, insertion of the microneedle is in the sclera of the eye. In one embodiment, drug flow into the SCS is accomplished without contacting underlying tissues with the microneedle, such as choroid and retina tissues.

The methods provided herein, in one embodiment, achieve delivery of drug to the suprachoroidal space, thereby allowing drug access to posterior ocular tissues not obtainable via topical, parenteral, intracameral or intravitreal drug delivery. Because the methods provided herein deliver drug to the posterior ocular tissue for the treatment of a posterior ocular disorder or choroidal malady, the suprachoroidal drug dose sufficient to achieve a therapeutic response in a human subject treated with the methods provided herein is less than the intravitreal, topical, parenteral or oral drug dose sufficient to elicit the same or substantially the same therapeutic response. In one embodiment, the SCS delivery methods described herein allow for decreased drug dose of the posterior ocular disorder treating drug, or the choroidal malady treating drug, compared to the intravitreal, topical, intracameral parenteral or oral drug dose sufficient to elicit the same or substantially the same therapeutic response. In a further embodiment, the suprachoroidal drug dose sufficient to elicit a therapeutic response is 75% or less, or 50% or less, or 25% or less than the intravitreal, topical parenteral or oral drug dose sufficient to elicit a therapeutic response. The therapeutic response, in one embodiment, is a reduction in severity of a symptom/clinical manifestation of the posterior ocular disorder or the choroidal malady for which the patient is undergoing treatment, or a reduction in number of symptom(s)/clinical manifestation(s) of the posterior ocular disorder choroidal malady for which the patient is undergoing treatment.

The term "suprachoroidal space," is used interchangeably with suprachoroidal, SCS, suprachoroid and suprachoroidia, and describes the potential space in the region of the eye disposed between the sclera and choroid. This region primarily is composed of closely packed layers of long pigmented processes derived from each of the two adjacent tissues; however, a space can develop in this region as a result of fluid or other material buildup in the suprachoroidal space and the adjacent tissues. Those skilled in the art will appreciate that the suprachoroidal space frequently is expanded by fluid buildup because of some disease state in the eye or as a result of some trauma or surgical intervention. In the present description, however, the fluid buildup is intentionally created by infusion of a drug formulation into the suprachoroid to create the suprachoroidal space (which is filled with drug formulation). Not wishing to be bound by theory, it is believed that the SCS region serves as a pathway for uveoscleral outflow (i.e., a natural process of the eye moving fluid from one region of the eye to the other through) and becomes a real space in instances of choroidal detachment from the sclera.

Figure 1C:
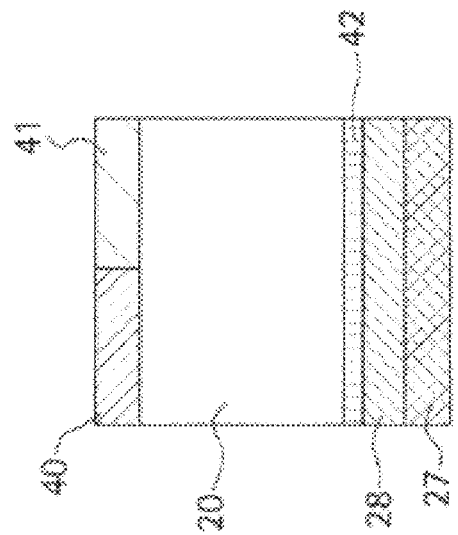
Figure 1D:
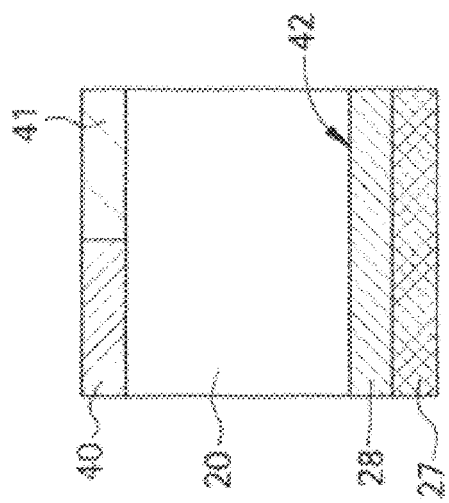

As used herein, "ocular tissue" and "eye" 10 include both the anterior segment 12 of the eye (i.e., the portion of the eye in front of the lens) and the posterior segment 14 of the eye (i.e., the portion of the eye behind the lens), as illustrated in FIG. 1A. The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The exposed portion of the sclera 20 on the anterior segment 12 of the eye is protected by a clear membrane referred to as the conjunctiva (not shown). Underlying the sclera 20 is the choroid 28 and the retina 27, collectively referred to as retinachoroidal tissue. The loose connective tissue, or potential space, between the choroid 28 and the sclera 20 is referred to as the suprachoroidal space (SCS) (not shown). FIG. 1B illustrates the cornea 16, which is composed of the epithelium 30, the Bowman's layer 32, the stroma 34, the Descemet's membrane 36, and the endothelium 38. FIG. 1C and FIG. 1D illustrate the sclera 20 with surrounding Tenon's Capsule 40 or conjunctiva 41, suprachoroidal space 42, choroid 28, and retina 27, both without and with a fluid in the suprachoroidal space, respectively.

As provided throughout, in one embodiment, the methods described herein are carried out with a hollow or solid microneedle, for example, a rigid microneedle. As used herein, the term "microneedle" refers to a conduit body having a base, a shaft, and a tip end suitable for insertion into the sclera and other ocular tissue and has dimensions suitable for minimally invasive insertion and drug formulation infusion as described herein. That is, the microneedle has a length or effective length that does not exceed about 2000 microns and a diameter that does not exceed about 600 microns. Both the "length" and "effective length" of the microneedle encompass the length of the shaft of the microneedle and the bevel height of the microneedle.

As used herein, the term "hollow" includes a single, straight bore through the center of the microneedle, as well as multiple bores, bores that follow complex paths through the microneedles, multiple entry and exit points from the bore(s), and intersecting or networks of bores. That is, a hollow microneedle has a structure that includes one or more continuous pathways from the base of the microneedle to an exit point (opening) in the shaft and/or tip portion of the microneedle distal to the base.

Figure 3:
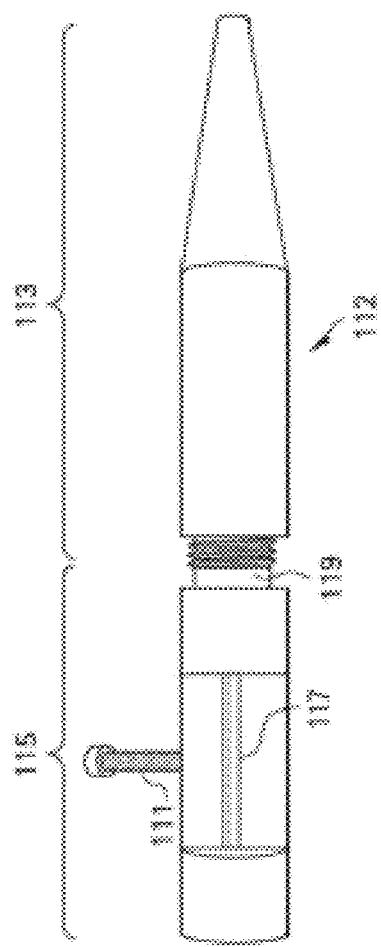
FIG. 3 is a cross-sectional view of the elongated body of the microneedle devices shown in FIG. 2.
Figure 2:
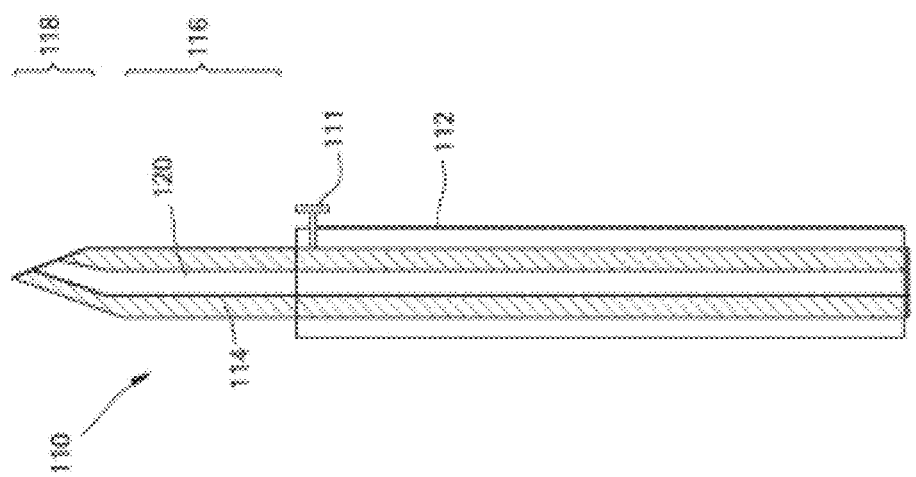
FIG. 2 is a cross-sectional view of a microneedle device comprising a hollow microneedle disposed in an elongated body according to one embodiment.

FIGS. 2-5 illustrate exemplary embodiments of microneedle devices. In one embodiment, illustrated in FIG. 2-3, the microneedle device 110 includes a hollow microneedle 114 having a hollow bore 140 through which a fluid drug formulation (not shown) can be delivered to the eye or through which a biological fluid can be withdrawn from the eye. The microneedle includes a proximal portion 116 and a tip portion 118. The microneedle 114 may extend from a base comprising, for example, an elongated body 112 having a distal end from which the proximal portion 116 and tip portion 118 of the microneedle extends. The elongated body may further comprise a means for securing 111 a base portion of the microneedle extending beyond the distal end of the base 112, such as a screw or pin. An exemplary embodiment of the elongated body 112 for securing the microneedle is illustrated in FIG. 3, and comprises a cap portion 113 and a base portion 115 having a hollow bore 117 therein. The cap portion 113 and base portion 115 of the elongated body 112 desirably comprise a means for manually adjusting the length of needle (i.e., the proximal portion and tip portion of the microneedle extending from the base 112) protruding out of the cap portion of the elongated body. Such means may include, for example, threads 119 allowing the cap portion 113 to be screwed in and out of the base portion 115 of the elongated body. In an exemplary embodiment illustrated in FIG. 4, the base portion 115 of the elongated body may be operably connected to an actuator 120 for controlled infusion of the fluid drug formulation through the microneedle into the suprachoroidal space.

The microneedle device may further comprise a fluid reservoir for containing the drug formulation, e.g., as a solution or suspension, and the drug reservoir being in operable communication with the bore of the microneedle at a location distal to the tip end of the microneedle. The fluid reservoir may be integral with the microneedle, integral with the elongated body, or separate from both the microneedle and elongated body.

The microneedle can be formed/constructed of different biocompatible materials, including metals, glasses, semiconductor materials, ceramics, or polymers. Examples of suitable metals include pharmaceutical grade stainless steel, gold, titanium, nickel, iron, gold, tin, chromium, copper, and alloys thereof. The polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Representative non-biodegradable polymers include various thermoplastics or other polymeric structural materials known in the fabrication of medical devices. Examples include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Biodegradable microneedles can provide an increased level of safety compared to non-biodegradable ones, such that they are essentially harmless even if inadvertently broken off into the ocular tissue.

The microneedle can be fabricated by a variety of methods known in the art or as described in the Examples below. In one embodiment, the hollow microneedle is fabricated using a laser or similar optical energy source. In one example, a microcannula may be cut using a laser to represent the desired microneedle length. The laser may also be use to shape single or multiple tip openings. Single or multiple cuts may be performed on a single microcannula to shape the desired microneedle structure. In one example, the microcannula may be made of metal such as stainless steel and cut using a laser with a wavelength in the infrared region of the light spectrum (e.g., from about 0.7 to about 300 µm). Further refinement may be performed using metal electropolishing techniques familiar to those in the field. In another embodiment, the microneedle length and optional bevel is formed by a physical grinding process, which for example may include grinding a metal cannula against a moving abrasive surface. The fabrication process may further include precision grinding, micro-bead jet blasting and ultrasonic cleaning to form the shape of the desired precise tip of the microneedle.

Further details of possible manufacturing techniques are described, for example, in U.S. Patent Application Publication No. 2006/0086689, U.S. Patent Application Publication No. 2006/0084942, U.S. Patent Application Publication No. 2005/0209565, U.S. Patent Application Publication No. 2002/0082543, U.S. Pat. No. 6,334,856, U.S. Pat. No. 6,611,707, U.S. Pat. No. 6,743,211, all of which are incorporated herein by reference in their entireties for all purposes.

The methods and devices provided herein allow for suprachoroidal drug delivery to be accomplished in a minimally invasive, non-surgical manner, superior to other non-surgical (e.g., conventional needle) and surgical approaches. For instance, in one embodiment, the methods provided herein are carried out via the use of one or more microneedles. In one embodiment, the microneedles are be inserted perpendicular, or at an angle from about 80° to about 100°, into the eye, e.g., into the sclera, reaching the suprachoroidal space in a short penetration distance. This is in contrast to long conventional needles or cannula which must approach the suprachoroidal space at a steep angle, taking a longer penetration path through the sclera and other ocular tissues, increasing the invasiveness of the method, the size of the needle track and consequently increasing the risk of infection and/or vascular rupture. With such long needles, the ability to precisely control insertion depth is diminished relative to the microneedle approach described herein.

The microneedle, in one embodiment, is part of an array of two or more microneedles such that the method further includes inserting at least a second microneedle into the sclera without penetrating across the sclera. In one embodiment, where an array of two or more microneedles are inserted into the ocular tissue, the drug formulation of each of the two or more microneedles may be identical to or different from one another, in drug, formulation, volume/quantity of drug formulation, or a combination of these parameters. In one case, different types of drug formulations may be injected via the one or more microneedles. For example, inserting a second hollow microneedle comprising a second drug formulation into the ocular tissue will result in delivery of the second drug formulation into the ocular tissue.

In another embodiment, the microneedle devices described herein are adapted to remove substances, such as a fluid, tissue, or molecule sample, from the eye.

Those skilled in the art will appreciate, however, that other types of microneedles (e.g., solid microneedles) and other methods of delivering the drug formulation into the suprachoroidal space and posterior ocular tissues may be used instead of or in conjunction with the delivery methods described herein. Non-limiting examples include dissolving, at least in part, a coating of a drug formulation off of a microneedle; detaching, at least in part, a coating of a drug formulation (e.g., as a substantially intact sleeve or in fragments) off of a microneedle; breaking or dissolving a microneedle off of a base to which the microneedle is integrally formed or is connected; or any combination thereof.

The microneedle devices described herein also may be adapted to use the one or more microneedles as a sensor to detect analytes, electrical activity, and optical or other signals. The sensor may include sensors of pressure, temperature, chemicals, and/or electromagnetic fields (e.g., light). Biosensors can be located on or within the microneedle, or inside a device in communication with the body tissue via the microneedle. The microneedle biosensor can be any of the four classes of principal transducers: potentiometric, amperometric, optical, and physiochemical. In one embodiment, a hollow microneedle is filled with a substance, such as a gel, that has a sensing functionality associated with it. In an application for sensing based on binding to a substrate or reaction mediated by an enzyme, the substrate or enzyme can be immobilized in the needle interior. In another embodiment, a wave guide can be incorporated into the microneedle device to direct light to a specific location, or for detection, for example, using means such as a pH dye for color evaluation. Similarly, heat, electricity, light, ultrasound or other energy forms may be precisely transmitted to directly stimulate, damage, or heal a specific tissue or for diagnostic purposes.

The microneedle device for non-surgically delivering drug to the suprachoroidal space of the eye of a human subject, in one embodiment, comprises a hollow microneedle. The device may include an elongated housing for holding the proximal end of the microneedle. The device may further include a means for conducting a drug formulation through the microneedle. For example, the means may be a flexible or rigid conduit in fluid connection with the base or proximal end of the microneedle. The means may also include a pump or other devices for creating a pressure gradient for inducing fluid flow through the device. The conduit may in operable connection with a source of the drug formulation. The source may be any suitable container. In one embodiment, the source may be in the form of a conventional syringe. The source may be a disposable unit dose container.

In one embodiment, the microneedle has an effective length of about 50 µm to about 2000 µm. In another particular embodiment, the microneedle has an effective length of from about 150 µm to about 1500 µm, or from about 300 µm to about 1250 µm, or from about 500 µm to about 1250 µm, or from about 500 µm to about 1500 µm, or from about 600 µm to about 1000 µm, or from about 700 µm to about 1000 µm. In one embodiment, the effective length of the microneedle is about 600 µm, or about 700 µm, or about 800 µm or about 1000 µm. In various embodiments, the proximal portion of the microneedle has a maximum width or cross-sectional dimension of from about 50 µm to 600 µm, or from about 50 µm to about 400 µm, or from about 50 µm to about 500 µm, or from about 100 µm to about 400 µm, or from about 200 µm to about 600 µm, or from about 100 µm to about 250 µm, with an aperture diameter of about 5 µm to about 400 µm. In a particular embodiment, the proximal portion of the microneedle has a maximum width or cross-sectional dimension of about 600 µm. Those skilled in the art will appreciate, however, that in embodiments in which the tip of the microneedle is beveled that the aperture diameter may be greater than the outer diameter of the proximal portion of the microneedle. The microneedle may be fabricated to have an aspect ratio (width:length) of about 1:1.5 to about 1:10. In one embodiment, the aspect ratio of the microneedle is about 1:3 to about 1:5. In another embodiment, the aspect ratio of the microneedle is about 1:4 to about 1:10.

The microneedle can have a straight or tapered shaft. In one embodiment, the diameter of the microneedle is greatest at the base end of the microneedle and tapers to a point at the end distal the base. The microneedle can also be fabricated to have a shaft that includes both a straight (i.e., untapered) portion and a tapered (e.g., beveled) portion. In various embodiments the microneedle has a bevel angle of about 5 degrees to about 30 degrees, of about 5 degrees to about 25 degrees, about 5 degrees to about 20 degrees, about 10 degrees to about 20 degrees, and about 10 degrees to about 30 degrees. The microneedles can be formed with shafts that have a circular cross-section in the perpendicular, or the cross-section can be non-circular. The tip portion of the microneedles can have a variety of configurations. The tip of the microneedle can be symmetrical or asymmetrical about the longitudinal axis of the shaft. The tips may be beveled, tapered, squared-off, or rounded. In various embodiments, the microneedle has a bevel height from about 50 µm to 500 µm, about 100 µm to about 500 µm, about 100 µm to about 400 µm, about 200 µm to about 400 µm, and about 300 µm to about 500 µm. In particular embodiments, the microneedle may be designed such that the tip portion of the microneedle is substantially the only portion of the microneedle inserted into the ocular tissue (i.e., the tip portion is greater than 75% of the total length of the microneedle, greater than 85% of the total length of the microneedle, or greater than about 95% of the total length of the microneedle). In other particular embodiments, the microneedle may be designed such that the tip portion is only a portion of the microneedle that is inserted into the ocular tissue and generally has a length that is less than about 75% of the total length of the microneedle, less than about 50% of the total length of the microneedle, or less than about 25% of the total length of the microneedle. For example, in one embodiment the microneedle has a total effective length between 500 µm and 1500 µm, wherein the tip portion has a length that is less than about 400 µm, less than about 300 µm, or less than about 200 µm.

In one embodiment, the height of the bevel is about 100 µm to about 500 µm. In another embodiment, the height of the bevel is about 500 µm or less, about 450 µm or less, about 400 µm or less or about 350 µm or less. In another embodiment, the height of the bevel is from about 200 µm to about 500 µm, or from about 100 µm to about 700 µm, or from about 200 µm to about 700 µm. In still other embodiments, the height of the bevel is from about 500 µm to about 900 µm, or from about 500 µm to about 800 µm, or from about 500 µm to about 700 µm. In this manner, the arrangement of the bevel can be such that the distal edge is sufficiently sharp such as to pierce a target tissue and penetrate into the vitreous without (i) substantially causing the target tissue to elastically deform or (ii) damaging internal structures of the eye, e.g., the lens or retina.

In one embodiment, the microneedle extends from a base. The base may be integral with or separate from the microneedle. The base may be rigid or flexible. The base may be substantially planar or it may be curved, for example, in the shape of the ocular tissue surface at the site of injection or, for example, curved away from the ocular surface (e.g., convex) so as to minimize contact between the base and the ocular tissue. Desirably, the base is shaped to provide minimal contact with the surface of the eye at the point of insertion. For example, in one embodiment, the base may extend only a minimal distance from the microneedle shaft substantially perpendicular. In another embodiment, the base may be shaped so as to elevate the ocular tissue towards the microneedle so as to counteract the deflection of the ocular tissue and facilitate insertion of the microneedle into the ocular tissue (e.g., the base may extend from the microneedle toward the tip portion of the microneedle so as to "pinch" the ocular tissue). Some such embodiments may be based, at least in part, on the devices described in U.S. Pat. No. 6,743,211, incorporated herein by reference.

In a particular embodiment, the microneedle device has a single microneedle. In one embodiment, illustrated in FIG. 5, the microneedle device 130 includes a convex base 132 and a hollow microneedle 134 which has a bore 140 through which a fluid drug formulation (not shown) can be delivered to the eye or through which a biological fluid can be withdrawn from the eye. The hollow microneedle 134 includes a proximal portion 136 and a tip portion 138.

The microneedle may extend from the base of the microneedle device at any angle suitable for insertion into the eye. In a particular embodiment, the microneedle extends from the base at an angle of about 90 degrees to provide approximately perpendicular insertion of the microneedles into the surface of the eye. In another particular embodiment, the microneedle extends from the base at an angle from about 60 to about 110 degrees, or from about 70 degrees to about 100 degrees, or from about 80 degrees to about 90 degrees, or from about 85 degrees to about 95 degrees.

The microneedle device may comprise a means for controllably inserting, and optionally retracting, the microneedle into the ocular tissue. In addition, the microneedle device may include means of controlling the angle at which the at least one microneedle is inserted into the ocular tissue (e.g., by inserting the at least one microneedle into the surface of the ocular tissue at an angle of about 90 degrees).

The depth of microneedle insertion into the ocular tissue can be controlled by the length of the microneedle, as well as other geometric features of the microneedle. For example, a flange or other a sudden change in microneedle width can be used to limit the depth of microneedle insertion. The microneedle insertion can also be controlled using a mechanical micropositioning system involving gears or other mechanical components that move the microneedle into the ocular tissue a controlled distance and, likewise, can be operated, for example, in reverse, to retract the microneedle a controlled distance. The depth of insertion can also be controlled by the velocity at which the microneedle is inserted into the ocular tissue. The retraction distance can be controlled by elastic recoil of the ocular tissue into which the microneedle is inserted or by including an elastic element within the microneedle device that pulls the microneedle back a specified distance after the force of insertion is released.

The angle of insertion can be directed by positioning the microneedle at a first angle relative to the microneedle base and positioning the base at a second angle relative to the ocular surface. In one embodiment, the first angle can be about 90° and the second angle can be about 0°. The angle of insertion can also be directed by having the microneedle protrude from a device housing through a channel in that housing that is oriented at a specified angle.

One skilled in the art may adapt mechanical systems known in the art in combination with the disclosure set forth herein and in the Examples below to devise suitable structures to controllably drive the microneedle insertion, which structures may be manually operable, electromechanically operable, or a combination thereof.

The transport of drug formulation or biological fluid through a hollow microneedle can be controlled or monitored using, for example, one or more valves, pumps, sensors, actuators, and microprocessors. For instance, in one embodiment the microneedle device may include a micropump, microvalve, and positioner, with a microprocessor programmed to control a pump or valve to control the rate of delivery of a drug formulation through the microneedle and into the ocular tissue. The flow through a microneedle may be driven by diffusion, capillary action, a mechanical pump, electroosmosis, electrophoresis, convection or other driving forces. Devices and microneedle designs can be tailored using known pumps and other devices to utilize these drivers. In one embodiment, the microneedle device may further include an iontophoretic apparatus, similar to that described in U.S. Pat. No. 6,319,240 to Beck, for enhancing the delivery of the drug formulation to the ocular tissue. In another embodiment the microneedle devices can further include a flowmeter or other means to monitor flow through the microneedles and to coordinate use of the pumps and valves.

The flow of drug formulation or biological fluid can be regulated using various valves or gates known in the art. The valve may be one which can be selectively and repeatedly opened and closed, or it may be a single-use type, such as a fracturable barrier. Other valves or gates used in the microneedle devices can be activated thermally, electrochemically, mechanically, or magnetically to selectively initiate, modulate, or stop the flow of material through the microneedles. In one embodiment, the flow is controlled with a rate-limiting membrane acting as the valve.

In another embodiment, the device includes an array of two or more microneedles. For example, the device may include an array of from 2 to 1000 (e.g., from 2 to 100) microneedles. In one embodiment, a device includes between 1 and 10 microneedles. An array of microneedles may include a mixture of different microneedles. For instance, an array may include microneedles having various lengths, base portion diameters, tip portion shapes, spacings between microneedles, drug coatings, etc. In embodiments wherein the microneedle device comprises an array of two or more microneedles, the angle at which a single microneedle extends from the base may be independent from the angle at which another microneedle in the array extends from the base.

The SCS drug delivery methods provided herein allow for the delivery of drug formulation over a larger tissue area and to more difficult to target tissue in a single administration as compared to previously known needle devices. Not wishing to be bound by theory, it is believed that upon entering the SCS the drug formulation flows circumferentially from the insertion site toward the retinochoroidal tissue, macula, and optic nerve in the posterior segment of the eye as well as anteriorly toward the uvea and ciliary body. In addition, a portion of the infused drug formulation may remain in the SCS as a depot, or remain in tissue overlying the SCS, for example the sclera, near the microneedle insertion site, serving as additional depot of the drug formulation that subsequently can diffuse into the SCS and into other adjacent posterior tissues.

The microneedle devices and non-surgical methods described herein may be used to deliver drug formulations to the eye of a human subject, particularly for the treatment, diagnosis, or prevention of a posterior ocular disorder or a choroidal malady. In one embodiment, the drug formulation comprises an effective amount of an anti-inflammatory drug, an immunosuppressive agent, a VEGF modulator (e.g., a VEGF antagonist), an angiogenesis inhibitor (e.g., a PDGF antagonist) or a vascular permeability inhibitor. In a further embodiment, the formulation comprises an anti-inflammatory drug selected from a steroid compound and a non-steroidal anti-inflammatory drug (NSAID). In even a further embodiment, the drug formulation is a triamcinolone formulation, e.g., a triamcinolone acetonide formulation.

The present invention, in one aspect, relates in to the treatment of a choroidal malady in a human patient in need thereof. The method, in one embodiment, comprises non-surgically delivering a drug formulation comprising an effective amount of a choroidal malady treating drug to the suprachoroidal space of one or both eyes of the patient in need of treatment. It should be understood that a patient having one eye will undergo treatment in only one eye.

In one aspect, the methods and microneedles described herein relate to the non-surgical administration of a drug formulation for the treatment of a choroidal malady or posterior ocular disorder, wherein the majority of the drug formulation is retained in the SCS in one or both eyes of a patient in need of treatment of either the choroidal malady or posterior ocular disorder, for a period of time after the non-surgical treatment method is completed. Without wishing to be bound by theory, drug formulation retention in the SCS contributes to the sustained release profile of the drug formulations described herein.

The human subject treated with the methods provided herein may be an adult or a child. A wide range of posterior ocular disorders and disorders and choroidal maladies are treatable with the methods, devices and drug formulations described herein.

Examples of posterior ocular disorders amenable for treatment by the methods, devices and drug formulations described herein include, but are not limited to, uveitis, glaucoma, macular edema, diabetic macular edema, retinopathy, age-related macular degeneration (for example, wet AMD or dry AMD), scleritis, optic nerve degeneration, geographic atrophy, choroidal disease, ocular sarcoidosis, optic neuritis, choroidal neovascularization, ocular cancer, genetic disease(s), autoimmune diseases affecting the posterior segment of the eye, retinitis (e.g., cytomegalovirus retinitis) and corneal ulcers. The posterior ocular disorders amenable for treatment by the methods, devices, and drug formulations described herein may be acute or chronic. For example, the ocular disease may be acute or chronic uveitis. Uveitis can be caused by infection with viruses, fungi, or parasites; the presence of noninfectious foreign substances in the eye; autoimmune diseases; or surgical or traumatic injury. Disorders caused by pathogenic organisms that can lead to uveitis or other types of ocular inflammation include, but are not limited to, toxoplasmosis, toxocariasis, histoplasmosis, herpes simplex or herpes zoster infection, tuberculosis, syphilis, sarcoidosis, Vogt-Koyanagi-Harada syndrome, Behcet's disease, idiopathic retinal vasculitis, Vogt-Koyanagi-Harada Syndrome, acute posterior multifocal placoid pigment epitheliopathy (APMPPE), presumed ocular histoplasmosis syndrome (POHS), birdshot chroidopathy, Multiple Sclerosis, sympathetic opthalmia, punctate inner choroidopathy, pars planitis, or iridocyclitis. Acute uveitis occurs suddenly and may last for up to about six weeks. Chronic uveitis is a form of uveitis in which the onset of signs and/or symptoms is gradual, and symptoms last longer than about six weeks.

Signs of uveitis include ciliary injection, aqueous flare, the accumulation of cells visible on ophthalmic examination, such as aqueous cells, retrolental cells, and vitreous cells, keratic precipitates, and hypema. Symptoms of uveitis include pain (such as ciliary spasm), redness, photophobia, increased lacrimation, and decreased vision. Posterior uveitis affects the posterior or choroid part of the eye. Inflammation of the choroid part of the eye is also often referred to as choroiditis. Posterior uveitis is may also be associated with inflammation that occurs in the retina (retinitis) or in the blood vessels in the posterior segment of the eye (vasculitis). In one embodiment, the methods provided herein comprise non-surgically administering to a uveitis patient in need thereof, an effective amount of a uveitis treating drug to the SCS of the eye of the patient. In a further embodiment, the patient experiences a reduction in the severity of the symptoms, after administration of a uveitis treating drug to the SCS.

In one embodiment, the drug formulation delivered to the SCS results in the patient experiencing a reduction in inflammation, neuroprotection, complement inhibition, drusen formation, scar formation, and/or a reduction in choriocapillaris or choroidal neocasvularization.

The non-surgical methods described herein are particularly useful for the local delivery of drugs to the posterior region of the eye, for example the retinochoroidal tissue, macula, and optic nerve in the posterior segment of the eye. In one embodiment, the non-surgical treatment methods and devices described herein may be used in gene-based therapy applications. For example, the method, in one embodiment, comprises administering a drug formulation into the suprachoroidal space to deliver select DNA, RNA, or oligonucleotides to targeted ocular tissues.

As provided throughout, the methods described herein are also amenable for the treatment of a choroidal malady in a patient in need of such treatment. In one embodiment, the patient in need of choroidal malady treatment has been unresponsive to a previous non-SCS method for treating the choroidal malady. Examples of choroidal maladies amenable for treatment by the methods, devices and drug formulations described herein include, but are not limited to, choroidal neovascularization, polypoidal choroidal vasculopathy, central sirrus choroidopathy, a multi-focal choroidopathy or a choroidal dystrophy (e.g., central gyrate choroidal dystrophy, serpiginous choroidal dystrophy or total central choroidal atrophy). Choroidal maladies are described in further detail below.

In one embodiment, the choroidal malady treating drug is an angiogenesis inhibitor, a vascular permeability inhibitor or an anti-inflammatory drug. The angiogenesis inhibitor, in one embodiment, is a vascular endothelial growth factor (VEGF) modulator or a platelet derived growth factor (PDGF) modulator. The choroidal malady treatment method, in one embodiment, comprises administering the drug formulation to the SCS of one or both eyes of the patient in need of treatment via a microneedle. In a further embodiment, the microneedle is a hollow microneedle having a tip and an opening, and the drug formulation is infused into the SCS of one or both eyes through the tip of the hollow microneedle.

The method of treating a posterior ocular disorder or choroidal malady in a human subject in need thereof comprises, in one embodiment, non-surgically administering a drug formulation to the suprachoroidal space of the eye of the human subject, wherein upon administration, the drug formulation flows away from the insertion site and is substantially localized to the posterior segment of the eye. In one embodiment, the non-surgical methods provided herein allow for longer retention of the drug in the eye, as compared to intravitreal, topical, parenteral, intracameral or oral administration of the same drug dose.

In one embodiment, the suprachoroidal drug dose sufficient to achieve a therapeutic response in a human subject treated with the non-surgical SCS drug delivery method is less than the intravitreal, parenteral, intracameral, topical, or oral drug dose sufficient to elicit the identical or substantially identical therapeutic response. In a further embodiment, the suprachoroidal drug dose is at least 10 percent less than the oral, parenteral or intravitreal dose sufficient to achieve the identical or substantially identical therapeutic response. In a further embodiment, the suprachoroidal dose is about 10 percent to about 25 percent less, or about 10 percent to about 50 percent less than the oral, parenteral, intracameral, topical, or intravitreal dose sufficient to achieve the identical or substantially identical therapeutic response. Accordingly, in one embodiment, the method of treating a posterior ocular disorder or choroidal malady described herein achieves a greater therapeutic efficacy than other routes of administration. In one embodiment, the non-surgical method provided herein comprises inserting a hollow microneedle into the sclera of the eye of the human subject and infusing a drug formulation through the hollow microneedle and into the suprachoroidal space of the eye. As described in more detail below, the drug formulation, in one embodiment, is a solution or suspension of the drug.

In one embodiment, where the non-surgical method for treating a posterior ocular disorder or choroidal malady in a human subject comprises drug delivery to the SCS of one or both eyes of the patient via a microneedle (hollow or solid), the microneedle insertion site is between the equator and the limbus of the respective eye.

In another embodiment, the insertion site is between about 2 mm and about 10 mm posterior to the limbus of the eye. In one embodiment, the microneedle insertion site is at the pars plana. However, in other embodiments the insertion site is outside the pars plana. In one embodiment, the insertion site of the microneedle is at about the equator of the eye.

In another embodiment, the insertion site is from 2 to 10 mm anterior to the limbus of the eye, for example, about 5 mm anterior to the limbus.

In another embodiment, the drug formulation is introduced into the SCS at the site of injection (i.e., at the tip of the microneedle) and then flows through the SCS away from the site of injection while the injection occurs. In another embodiment, the site of injection (i.e., at the tip of the microneedle) is anterior to the equator of the eye and at least a portion of the drug formulation flows posterior to the equator of the eye during the injection (i.e., while drug formulation continues to flow out of the microneedle). In another embodiment, the site of injection (i.e., at the tip of the microneedle) is anterior to the equator of the eye and at least a portion of the drug formulation flows near the macular during the injection (i.e., while drug formulation continues to flow out of the microneedle).

In one embodiment, the depth of insertion of the microneedle into the ocular tissue is precisely controlled. Various methods can be used to control the insertion depth of the microneedles described herein. In a particular embodiment, the insertion depth is limited by the selected length or effective length of the microneedle. The "effective length" is that portion available for tissue insertion, i.e., the length that extends from the base and would be inserted if there were zero tissue deformation. The "effective length" neglects any proximal portion of the microneedle that extends into or through the base and thus cannot be inserted in the tissue, and includes both the microneedle shaft length and bevel length. That is, the microneedle may have an effective length approximately equal to the desired penetration depth. In one embodiment, the microneedle is short enough that the tip of the microneedle may be inserted substantially to the base of the sclera (i.e., near the interface of the sclera and choroid) without completely penetrating across the sclera. In another embodiment, the tip of the microneedle is inserted through the sclera into the suprachoroidal space without penetrating through the choroid.

In another embodiment, the microneedle is designed to have a length longer than the desired penetration depth, but the microneedle is controllably inserted only part way into the tissue. Partial insertion may be controlled by the mechanical properties of the tissue, which bends and dimples during the microneedle insertion process. In this way, as a microneedle is inserted into the tissue, its movement partially elastically deforms the tissue and partially penetrates into the tissue. By controlling the degree to which the tissue deforms, the depth of microneedle insertion into the tissue can be controlled.

In one embodiment, the microneedle is inserted into the eye of the human patient using a rotational/drilling technique and/or a vibrating action. In this way, the microneedle can be inserted to a desired depth by, for example, drilling the microneedles a desired number of rotations, which corresponds to a desired depth into the tissue. See, e.g., U.S. Patent Application Publication No. 2005/0137525, which is incorporated herein by reference, for a description of drilling microneedles. The rotational/drilling technique and/or a vibrating action may be applied during the insertion step, retraction step, or both.

In one embodiment, the drug formulation is infused into the suprachoroidal space through a hollow microneedle by driving the drug formulation from a source reservoir into the ocular tissue using a pressure gradient (e.g., pumping, syringe). In other embodiments, the drug formulation is driven from a source reservoir into the ocular tissue using an electric field (e.g., iontophoresis) or another externally applied energy (e.g., ultrasound/acoustic energy).

In one embodiment, the amount of drug formulation infused into the suprachoroidal space from the non-surgical drug delivery methods described herein is from about 10 µL to about 200 µL, e.g., from about 50 µL to about 150 µL. In another embodiment, from about 10 µL to about 500 µL, e.g., from about 50 µL to about 250 µL, is non-surgically administered to the suprachoroidal space. For example, in one embodiment, the non-surgical method comprises inserting a hollow microneedle into the sclera at an insertion site, the microneedle having a tip end with an opening, and infusing the drug formulation through a hollow microneedle and into the suprachoroidal space. As provided above, from about 10 µL to about 200 µL, or from about 50 µL to about 150 µL or from about 10 µL to about 500 µL or from about 50 µL to about 250 µL can be delivered via one or more hollow microneedles described herein.

In one embodiment, the driving force or pressure infusing the drug formulation through the hollow microneedle causes the infused drug formulation to flow within the suprachoroidal space and reach the back of the eye during the administration (i.e., during the infusion) process. This may occur in less than one or two minutes, such as from about 1 second to about 100 seconds, e.g., from about 10 seconds to about 30 seconds. In one aspect, the drug formulation flows away from the insertion site during and after infusing the drug into the SCS. In a further embodiment, the drug flows circumferentially within the suprachoroidal space during the infusion process to a site that is at least 2.5 mm away from the insertion site, or to a site that is at least 5 mm away from the insertion site, or to a site that is at least 7.5 mm away from the insertion site, or to a site that is at least 10 mm away from the insertion site. In one embodiment, the drug formulation flows circumferentially within the suprachoroidal space from the insertion site toward the back (posterior segment) of the eye (i.e., the retinochoroidal tissue, macula, and optic nerve in the posterior segment of the eye).

The amount of drug delivered within the SCS also may be controlled, in part, by the type of microneedle used and how it is used. In one embodiment, a hollow microneedle is inserted into the ocular tissue and progressively retracted from the ocular tissue after insertion to deliver a fluid drug, where after achieving a certain dosage, the delivery could be stopped by deactivating the fluid driving force, such as pressure (e.g., from a mechanical device such as a syringe) or an electric field, to avoid leakage/uncontrolled deliver of drug. Desirably, the amount of drug being delivered is controlled by driving the fluid drug formulation at a suitable infusion pressure. In one embodiment, the infusion pressure may be at least 150 kPa, at least 250 kPa, or at least 300 kPa. In another embodiment, the infusion pressure is about 150 kPa to about 300 kPa. Suitable infusion pressures may vary with the particular patient or species.

It should be noted that the desired infusion pressure to deliver a suitable amount of drug formulation might be influenced by the depth of insertion of the microneedle and the composition of the drug formulation. For example, a greater infusion pressure may be required in embodiments wherein the drug formulation for delivery into the eye is in the form of or includes nanoparticles or microparticles encapsulating the active agent or microbubbles. Nanoparticle or microparticle encapsulation techniques are well known in the art. In one embodiment, the drug formulation is comprised of drug particles in suspension with a $D_{99}$ of 10 µm or less. In one embodiment, the drug formulation is comprised of drug particles in suspension with a $D_{99}$ of 7 µm or less. In another embodiment, the drug formulation is comprised of drug particles in suspension with a $D_{99}$ of 3 µm or less. In another embodiment, the drug formulation is comprised of drug particles in suspension with a $D_{50}$ of 5 µm or less. In one embodiment, the drug formulation is comprised of drug particles in suspension with a $D_{50}$ 1 µm or less.

Figure 6B:
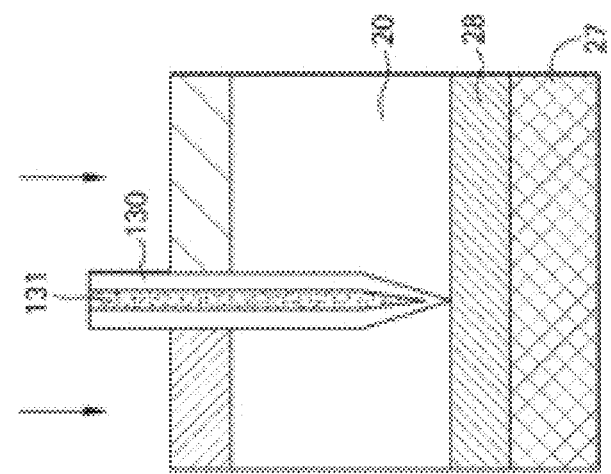
FIGS. 6A and 6B illustrate an embodiment of a process for using a hollow microneedle to deliver drug into the suprachoroidal space of an eye, where the process includes inserting the hollow microneedle into the sclera and infusion of a fluid drug formulation into the suprachoroidal space.
Figure 6A:
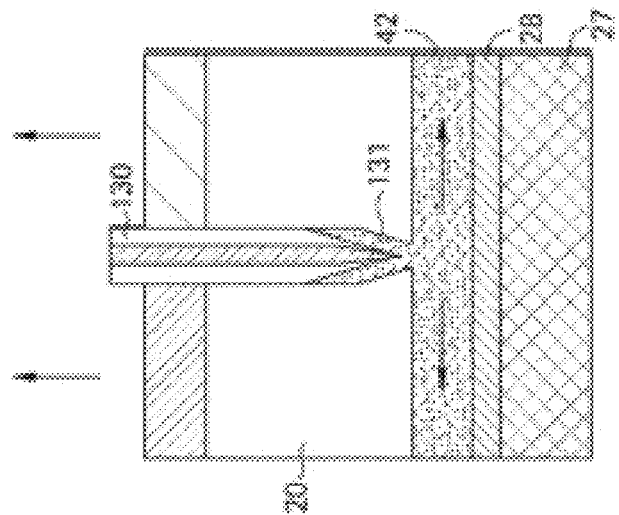

In one embodiment, the non-surgical method of administering a drug to the SCS further includes partially retracting the hollow microneedle after insertion of the microneedle into the eye, and before and/or during the infusion of the drug formulation into the suprachoroidal space. In a particular embodiment, the partial retraction of the microneedle occurs prior to the step of infusing the drug formulation into the ocular tissue. This insertion/retraction step may form a pocket and beneficially permits the drug formulation to flow out of the microneedle unimpeded or less impeded by ocular tissue at the opening at the tip portion of the microneedle. This pocket may be filled with drug formulation, but also serves as a conduit through with drug formulation can flow from the microneedle, through the pocket and into the suprachoroidal space. FIG. 6A shows a hollow microneedle 130 inserted into the sclera 20, with drug formulation 131 temporarily positioned in the hollow bore of the microneedle. (The fluid communication to a reservoir of the drug formulation is not shown.) FIG. 6B shows the microneedle 130 following partial retraction and infusion of the drug formulation 131 into the suprachoroidal space. Arrows show the circumferential flow of the drug formulation through the suprachoroidal space.

In one embodiment, the microneedle infuses a drug formulation through the sclera into the suprachoroidal space for controlled (i.e., sustained, extended, or modulated over time) release of a drug to one or more ocular or neighboring tissues. This "controlled release" or "sustained release" or "extended release" or "modulated release" is generally more prolonged than that obtainable by topical application or intravitreal injection of the drug formulation to the ocular tissue. In one embodiment, there is a controlled, extended, sustained or modulated release of the drug formulation after at least one microneedle is withdrawn from the ocular tissue. This delivery method can be particularly advantageous with ocular tissues, where it is desirable for the insertion and withdrawal process to occur over as short a period as possible to minimize patient discomfort—in contrast to transdermal microneedle patch applications, where patches may more likely be worn (with microneedles inserted) over an extended period without patient discomfort.

In another aspect, the method of treating a posterior ocular disorder or choroidal malady by non-surgically administering a drug to the suprachoroidal space of the eye of a human subject includes monitoring the insertion of the microneedle and/or infusion of the fluid drug formulation to ensure precise delivery of the fluid drug formulation to the SCS (see, e.g., FIG. 18). Such monitoring may be achieved using imaged-guided feedback methods during one or more of these steps, non-limiting examples of which include conventional microscopy, MRI, x-ray, confocal microscopy, ocular coherence tomography (e.g., anterior segment optical coherence tomography, Heidelberg retina tomography, spectral domain optical coherence tomography), fluorescein angiography, indocyanine green angiography, high resolution stereoscopic fundus photography, autofluorescence imaging, ultra-wide field imaging, and various ultrasound techniques. Thus, the method may further comprise determining whether an initial infusion of the fluid drug formulation has flowed into the suprachoroidal space of the eye and away from the insertion site. If it is determined that an initial infusion has been successful, a desired volume of the fluid drug formulation can be infused and the infusion discontinued by removing the fluid driving force, such as pressure, and retracting the microneedle from the eye. If, however, it is determined that the initial infusion of the fluid drug formulation has been unsuccessful (i.e., substantially none of the drug formulation has flowed into the suprachoroidal space of the eye and away from the insertion site), then the microneedle may be repositioned and the process repeated until a successful delivery is achieved.

Targeting a drug formulation to the SCS and the posterior ocular tissues allows for high concentrations of the drug to be delivered to the choroid/sclera and the retina, with little to no drug being delivered to the aqueous humor of the anterior chamber. Additionally, the methods provided herein allow for greater drug retention in the eye compared to other drug delivery methods, for example, a greater amount of drug is retained in the eye when delivered via the methods provided herein as compared to the same dose delivered via intracameral, intravitreal, topical, parenteral or oral drug delivery methods. Accordingly, in one embodiment, the intraocular elimination half life ($t_{1/2}$) of the drug when delivered via the methods described herein is greater than the intraocular $t_{1/2}$ of the drug when the same drug dose is administered intravitreally, intracamerally, topically, parenterally or orally. In another embodiment, the intraocular $C_{max}$ of the drug, when delivered via the methods described herein, is greater than the intraocular $C_{max}$ of the drug when the same drug dose is administered intravitreally, intracamerally, topically, parenterally or orally. In another embodiment, the mean intraocular area under the curve ($AUC_{0-t}$) of the drug, when administered to the SCS via the methods described herein, is greater than the intraocular $AUC_{0-t}$ of the drug, when administered intravitreally, intracamerally, topically, parenterally or orally. In yet another embodiment, the intraocular time to peak concentration ($t_{max}$) of the drug, when administered to the SCS via the methods described herein, is greater than the intraocular $t_{max}$ of the drug, when the same drug dose is administered intravitreally, intracamerally, topically, parenterally or orally. In a further embodiment, the drug is an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent, or a vascular permeability inhibitor. In even a further embodiment, the drug is triamcinolone, infliximab, mycophenolate, sorafenib, axitinib or nepafenac.

In one embodiment, the intraocular $t_{1/2}$ of the drug when administered via the non-surgical SCS drug delivery methods provided herein, is longer than the intraocular $t_{1/2}$ of the drug when the identical dose is administered topically, intracamerally, intravitreally, orally or parenterally. In a further embodiment, the intraocular $t_{1/2}$ of the drug when administered via the non-surgical SCS drug delivery methods provided herein, is from about 1.1 times to about 10 times longer, or from about 1.25 times to about 10 times longer, or from about 1.5 times to about 10 times longer, or about 2 times to about 5 times longer, than the intraocular $t_{1/2}$ of the drug when the identical dosage is administered topically, intracamerally, intravitreally, orally or parenterally. In a further embodiment, the drug is an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent, or a vascular permeability inhibitor.

In another embodiment, the intraocular $C_{max}$ of the drug, when delivered via the methods described herein, is greater than the intraocular $C_{max}$ of the drug when the same drug dose is administered intravitreally, intracamerally, topically, parenterally or orally. In a further embodiment, the intraocular $C_{max}$ of the drug when administered via the non-surgical SCS drug delivery methods provided herein, is at least 1.1 times greater, or at least 1.25 times greater, or at least 1.5 times greater, or at least 2 times greater, or at least 5 times greater, than the intraocular $C_{max}$ of the drug when the identical dose is administered topically, intracamerally, intravitreally, orally or parenterally. In one embodiment, the intraocular $C_{max}$ of the drug when administered via the non-surgical SCS drug delivery methods provided herein, is about 1 to about 2 times greater, or about 1.25 to about 2 times greater, or about 1 to about 5 times greater, or about 1 to about 10 times greater, or about 2 to about 5 times greater, or about 2 to about 10 times greater, than the intraocular $C_{max}$ of the drug when the identical dose is administered topically, intracamerally, intravitreally, orally or parenterally. In a further embodiment, the drug is an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent or a vascular permeability inhibitor. In one embodiment, the drug is triamcinolone, infliximab, mycophenolate, methotrexate, sorafenib, axitinib or nepafenac.

In another embodiment, the mean intraocular area under the curve ($AUC_{0-t}$) of the drug, when administered to the SCS via the methods described herein, is greater than the intraocular $AUC_{0-t}$ of the drug, when administered intravitreally, intracamerally, topically, parenterally or orally. In a further embodiment, the intraocular $AUC_{0-t}$ of the drug when administered via the non-surgical SCS drug delivery methods provided herein, is at least 1.1 times greater, or at least 1.25 times greater, or at least 1.5 times greater, or at least 2 times greater, or at least 5 times greater, than the intraocular $AUC_{0-t}$ of the drug when the identical dose is administered topically, intracamerally, intravitreally, orally or parenterally. In one embodiment, the intraocular $AUC_{0-t}$ of the drug when administered via the non-surgical SCS drug delivery methods provided herein, is about 1 to about 2 times greater, or about 1.25 to about 2 times greater, or about 1 to about 5 times greater, or about 1 to about 10 times greater, or about 2 to about 5 times greater, or about 2 to about 10 times greater, than the intraocular $AUC_{0-t}$ of the drug when the identical dose is administered topically, intracamerally, intravitreally, orally or parenterally. In a further embodiment, the drug is an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent or a vascular permeability inhibitor. In even a further embodiment, the drug is triamcinolone, infliximab, mycophenolate, methotrexate, sorafenib, axitinib or nepafenac.

In one embodiment, the drug formulation comprising the effective amount of the drug (e.g., an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent or a vascular permeability inhibitor), once delivered to the SCS, is substantially retained in the SCS over a period of time. For example, in one embodiment, about 80% of the drug formulation is retained in the SCS for about 30 minutes, or about 1 hour, or about 4 hours or about 24 hours or about 48 hours or about 72 hours. In this regard, a depot of drug is formed in the SCS and/or surrounding tissue, to allow for sustained release of the drug over a period of time.

In one embodiment, the suprachoroidal space, once loaded with drug (e.g., drug microparticles or nanoparticles), provides a sustained release of drug to the retina or other posterior ocular tissues over a period of time. The targeting of the drug to the posterior ocular tissues via the methods described herein allows for a greater therapeutic efficacy in the treatment of one or more posterior ocular disorders or choroidal maladies (e.g., PCV), as compared to other administration methods of the same drug dose, such as intravitreal, intracameral, oral, parenteral and topical delivery of the same drug dose. In a further embodiment, the therapeutic effect of the drug delivered to the SCS is achieved with a lower dose than the intravitreal, intracameral, topical, parenteral or oral dose sufficient to achieve the same therapeutic effect in the human subject. Additionally, without wishing to be bound by theory, the lower doses achievable with the methods provided herein result in reduced number of side effects of the drug, and/or reduced severity of one or more side effect(s), compared to higher doses of the drug, or the same drug dose delivered to the human patient via non-suprachoroidal routes of administration (e.g., intravitreal, intracameral, topical, parenteral, oral). For example, the methods provided herein provide a reduced number of side effects, or reduced severity of one or more side effects, or clinical manifestations, as compared to oral, topical, intracameral, parenteral or intravitreal administration of the same drug at the same dose. In one embodiment, the side effect or clinical manifestation that is lessened in the treated patient is subretinal exudation and/or subretinal bleeding.

In one embodiment, the non-surgical suprachoroidal drug delivery methods provided herein result in an increased therapeutic efficacy and/or improved therapeutic response, as compared to oral, parenteral and/or intravitreal drug delivery methods of the identical or similar drug dose. In one embodiment, the SCS drug dose sufficient to provide a therapeutic response is about 90%, or about 75%, or about one-half (e.g., about one half or less) the intravitreal, intracameral, topical, oral or parenteral drug dose sufficient to provide the same or substantially the same therapeutic response. In another embodiment, the SCS dose sufficient to provide a therapeutic response is about one-fourth the intravitreal, intracameral, topical, oral or parenteral drug dose sufficient to provide the same or substantially the same therapeutic response. In yet another embodiment, the SCS dose sufficient to provide a therapeutic response is one-tenth the intravitreal, intracameral, topical, oral or parenteral drug dose sufficient to provide the same or substantially the same therapeutic response. In one embodiment, the therapeutic response is a decrease in inflammation, as measured by methods known to those of skill in the art. In another embodiment, the therapeutic response is a decrease in number of ocular lesions, or decrease in ocular lesion size.

In one embodiment, the total amount of the effective amount of the drug in the drug formulation is about 0.05 mg to about 5 mg. In one embodiment, the total amount of the drug in the drug formulation is about 0.2 mg to about 4 mg. In another embodiment, the total amount of the drug in the drug formulation is about 1 mg to about 4 mg. Drug doses can be varied according to methods known to those of skill in the art and will vary, for example, based on patient age and clinical manifestation of the posterior ocular disorder or choroidal malady.

The therapeutic efficacy of the drug formulations delivered by the methods described herein and therapeutic response of the human subject can be assayed by standard means in the art, as known to those of skill in the art. In general, the therapeutic efficacy of any particular drug can be assessed by measuring the response of the human subject after administration of the drug; a drug with a high therapeutic efficacy will show a greater amelioration and/or discontinuation of symptoms than a drug with a lower therapeutic efficacy. In non-limiting examples, the efficacy of the drug formulations (e.g., an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent or a vascular permeability inhibitor formulation) provided herein can be measured, for example, by observing changes in pain intensity, changes in ocular lesions (size or number), intraocular pressure, inflammation (e.g., by measuring changes in the Hackett/McDonald ocular score), ocular hypertension, and/or visual acuity.

In another embodiment, the efficacy of the drug, e.g., an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent or a vascular permeability inhibitor, can be measured, for example, by observing changes in the measurements according to the Hackett/McDonald ocular scores, inflammation, visual acuity, and/or edema. In another embodiment, the efficacy of the drug, for example triamcinolone or mycophenolate, can be measured, for example, by observing changes in the measurements according to the Hackett/McDonald ocular scores, inflammation, visual acuity, and/or edema. In another embodiment, the therapeutic efficacy of the drug, for example sorafenib and/or axitinib, can be measured, for example, by observing changes in lesion growth and/or number. In another embodiment, the efficacy of the drug, for example infliximab (Remicade®), can be measured, for example, by observing changes in retinal thickness, inflammation, visual acuity, photophobia, typical time between flares, corneal ulceration, and/or edema. In another embodiment, the efficacy of the drug, for example nepafenac, can be measured, for example, by observing changes in optical coherence tomography (OCT) measurements of retinal thickness and volume, inflammation, visual acuity, pain and/or intraocular pressure.

In another embodiment, the efficacy of the drug, for example azathiopine, can be measured, for example, by observing changes in visual acuity, macular edema, intraocular pressure, inflammation, and/or measurements on the SF-36 Physical Component Score. In another embodiment, the efficacy of the drug, for example an anti-inflammatory drug such as an TNF family antagonist, for example, TNF-α antagonist, lymphotoxin-α antagonist, lymphotoxin-β antagonist, CD27L antagonist, CD20L antagonist, FASL antagonist, 4-BBL antagonist, OX40L antagonist, TNF-related apoptosis inducing ligand (TRAIL) antagonist, a Janus kinase (JAK) antagonist, or interleukin antagonist, can be measured, for example, by observing changes in inflammation, lesions, cell death, and/or visual acuity. In another embodiment, the therapeutic efficacy of cyclophosphamide can be measured, for example, by observing changes in lesion size and/or number, lesion growth, visual acuity, macular edema, intraocular pressure and/or inflammation.

In one embodiment, the non-surgical administration of an effective amount of a drug formulation to the SCS results in a decreased number of deleterious side effects or clinical manifestations as compared to the number of side effects or clinical manifestations caused by the same drug dose administered intravitreally, intracamerally, orally or parenterally. In another embodiment, the non-surgical administration of an effective amount of a drug formulation to the SCS results in a decreased number of one or more deleterious side effects or clinical manifestations, as compared to the deleterious side effects or clinical manifestations caused by the same drug dose administered intravitreally, intracamerally, orally or parenterally. Examples of side effects and clinical manifestations that can be reduced or ameliorated include, but are not limited to, inflammation, gastrointestinal side effects (e.g., diarrhea, nausea, gastroenteritis, vomiting, gastrointestinal, rectal, and duodenal hemorrhage, hemorrhagic pancreatitis, large intestine perforation black or bloody stools, and/or coughing up blood); hematologic side effects (e.g., leucopenia, anemia, pancytopenia and agranulocytosis, thrombocytopenia, neutropenia, pure red cell aplasia (PRCA), deep venous thrombosis easy bruising; and/or unusual bleeding from the nose, mouth, vagina, or rectum); immunologic side effects/clinical manifestations immunosuppression, immunosuppression resulting in sepsis, opportunistic infections (herpes simplex virus, herpes zoster, and invasive candidal infections), and/or increased infection); oncologic side effects/clinical manifestations (e.g. lymphoma, lymphoproliferative disease and/or non-melanoma skin carcinoma); renal side effects/clinical manifestations (e.g. dysuria, urgency, urinary tract infections, hematuria, kidney tubular necrosis, and/or BK virus-associated nephropathy); metabolic side effects/clinical manifestations (e.g. edema, hyperphosphatemia, hypokalemia, hyperglycemia, hyperkalemia. swelling, rapid weight gain, and/or enlarged thyroid); respiratory side effects/clinical manifestations (e.g. respiratory infection, dyspnea, increased cough, primary tuberculosis dry cough, wheezing, and/or stuffy nose); dermatologic side effects/clinical manifestations (e.g. acne; rash, dyshidrotic eczema, papulosquamous psoriatic-like skin eruption rash, blisters, oozing, mouth sores, and/or hair loss); musculoskeletal side effects/clinical manifestations (e.g. myopathy and/or muscle pain), hepatic side effects/clinical manifestations (e.g. hepatoxicity and/or jaundice), abdominal pain, increased incidence of first trimester pregnancy loss, missed menstrual periods, severe headache, confusion, change in mental status, vision loss, seizure (convulsions), increased sensitivity to light, dry eye, red eye, itchy eye, and/or high blood pressure. As provided above, the reduction or amelioration of the side effect or clinical manifestation is a reduction or amelioration, as compared to the severity of the side effect or clinical manifestation prior to administration of the drug formulation to the SCS of the eye of the patient, or a reduction or amelioration of the side effect or clinical manifestation in the patient, as compared to the reduction or amelioration experienced upon intravitreal, intracameral, parenteral or oral administration of the same drug.

In one embodiment, the non-surgical administration of an effective amount of a drug formulation to the SCS results in a decreased number of choroidal malady symptoms, as compared to the number of symptoms experienced by the patient prior to administration of the drug to the SCS, or compared to the number of symptoms experienced by the patient after treatment with the same drug dose administered intravitreally, intracamerally, orally or parenterally.

In one embodiment, the non-surgical administration of the drug formulation comprising an effective amount of a choroidal malady treating drug to the SCS of one or both eyes of the patient results in a decreased number of deleterious side effects or deleterious clinical manifestations, as compared to the number of deleterious side effects or clinical manifestations caused by the same drug dose administered intravitreally, intracamerally, orally, topically or parenterally. In another embodiment, the non-surgical administration of an effective amount of a drug formulation to the SCS results in a decreased severity of a side effect or clinical manifestation in a patient suffering from a choroidal malady. In a further embodiment, the severity of the side effect or clinical manifestation is decreased, compared to the severity of the deleterious side effect or clinical manifestation caused by the same drug dose administered intravitreally, intracamerally, orally, topically or parenterally. For example, in one embodiment, subretinal exudation is reduced and/or subretinal bleeding is reduced in a patient suffering from a choroidal malady, upon administration of the drug formulation to the SCS of the patient's eye, as compared to the subretinal exudation and/or subretinal bleeding, prior to administration of the drug to the SCS. In a further embodiment, the subretinal exudation is reduced and/or subretinal bleeding is reduced in the patient, compared to the reduction in severity experienced when the same drug is administered intravitreally, intracamerally, orally, topically or parenterally.

The delivery of the drug formulation to the SCS allows a greater retention of the drug in the posterior ocular tissue, as compared to delivery of the same drug via a topical, intravitreal, intracameral, oral or parenteral route. In one embodiment, the concentration of the drug can be achieved at greater than 10 µg/g posterior ocular tissue for 28 days or longer after a single dose. In another embodiment, the concentration of the drug can be achieved at greater than 100 µg/g posterior ocular tissue for 28 days or longer after a single dose. In another embodiment, the concentration of the drug can be achieved at greater than 1000 µg/g tissue for longer than 28 days after a single dose. It has been found that more hydrophobic drugs clear slowly from the SCS compared to more water soluble drugs. In one embodiment, the drug formulation administered to the SCS comprises a more hydrophobic drug.

In one embodiment, a method for treating a patient for a choroidal malady is provided, wherein the method comprises non-surgically administering a drug formulation comprising an effective amount of a choroidal malady treating drug (e.g., an angiogenesis inhibitor such as a VEGF modulator) to the SCS of one or both eyes of the patient in need of treatment, wherein upon administration, the drug formulation is substantially localized to the posterior segment of the eye. In a further embodiment, the drug formulation is substantially localized to the RPE. In one embodiment, the drug is substantially localized to the macula or the subretinal space. One or more of the microneedles described herein, in one embodiment, are used to carry out the method.

The method of treating a choroidal malady in a human subject in need thereof comprises, in one embodiment, non-surgically administering a drug formulation comprising an effective amount of a choroidal malady treating drug to the suprachoroidal space of one or both eyes of the human subject. In a further embodiment, the effective amount of the choroidal malady treating drug comprises an effective amount of an anti-inflammatory drug, a vascular endothelial growth factor (VEGF) modulator, a platelet derived growth factor (PDGF) modulator, an angiogenesis inhibitor, an immunosuppressive agent or a vascular permeability inhibitor. In one embodiment, upon administration, the choroidal malady treating drug formulation flows away from the insertion site and is substantially localized to the posterior segment of the eye. In one embodiment, the non-surgical methods provided herein allow for longer retention of the drug in the eye, as compared to intravitreal, topical, parenteral or oral administration of the same drug dose.

In patients undergoing ocular treatment via shunts or cannulae, or other surgical methods, a marked increase or decrease in intraocular pressure has been reported after the treatment method commences. In one embodiment, the intraocular pressure (TOP) of the patient's eye undergoing treatment for the posterior ocular disorder or choroidal maladay, 2 minutes, 10 minutes, 15 minutes or 30 minutes after suprachoroidal drug administration, is substantially the same TOP, compared to the TOP of the patient's eye prior to administration of the posterior ocular disorder or choroidal malady treating drug. In one embodiment, the TOP of the patient's eye undergoing treatment for the posterior ocular disorder or choroidal maladay, 2 minutes, 10 minutes, 15 minutes or 30 minutes after suprachoroidal drug administration, varies by no more than 10%, compared to the TOP of the patient's eye prior to administration of the posterior ocular disorder or choroidal malady treating drug. In one embodiment, the TOP of the patient's eye undergoing treatment for the posterior ocular disorder or choroidal maladay, 2 minutes, 10 minutes, 15 minutes or 30 minutes after suprachoroidal drug administration, varies by no more than 20%, compared to the TOP of the patient's eye prior to administration of the posterior ocular disorder or choroidal malady treating drug. In one embodiment, the TOP of the patient's eye undergoing treatment for the posterior ocular disorder or choroidal maladay, 2 minutes, 10 minutes, 15 minutes or 30 minutes after suprachoroidal drug administration, varies by no more than 10%-30%, compared to the TOP of the patient's eye prior to administration of the posterior ocular disorder or choroidal malady treating drug. In a further embodiment, the effective amount of the posterior ocular disorder or choroidal malady treating drug comprises an effective amount of an anti-inflammatory drug, a vascular endothelial growth factor (VEGF) modulator, a platelet derived growth factor (PDGF) modulator, an angiogenesis inhibitor, an immunosuppressive agent or a vascular permeability inhibitor.

The choroidal malady amenable for treatment with the methods described herein, in one embodiment, is a choroidal neovascularization, choroidal sclerosis, polypoidal choroidal vasculopathy, central sirrus choroidopathy, a multi-focal choroidopathy or a choroidal dystrophy. The choroidal dystrophy, for example, is central gyrate choroidal dystrophy, serpiginous choroidal dystrophy or total central choroidal atrophy. In some embodiments, the patient in need of treatment of the choroidal malady experiences subretinal exudation and bleeding, and the methods provided herein lessen the subretinal exudation and/or bleeding, compared to the subretinal exudation and/or bleeding experienced by the patient prior to administration of the drug formulation to the SCS. In another embodiment, the patient in need of treatment experiences subretinal exudation and bleeding, and the subretinal exudation and bleeding experienced by the patient after undergoing one of the non-surgical treatment methods provided herein is less than the subretinal exudation and bleeding experienced by the patient after intravitreal therapy with the same drug at the same dose.

In one embodiment, the methods provided herein provide for effective treatment of a patient who had previously undergone choroidal malady or posterior ocular disorder treatment, but was unresponsive, or not properly responsive to the prior treatment. For example, in one embodiment, a patient undergoing a choroidal malady treatment method or posterior ocular disorder treatment method of the present invention was previously treated for the same choroidal malady or posterior ocular disorder, but was unresponsive or not properly responsive. As one of skill in the art will appreciate, a patient unresponsive or not properly responsive to treatment does not exhibit an improvement in a symptom or improvement in a clinical manifestation of the choroidal malady or posterior ocular disorder. In one embodiment, the symptom or clinical manifestation is lesion size, inflammation, edema, visual acuity or vitreous haze.

In one embodiment, a patient in need of treatment of polypoidal choroidal vasculopathy is treated with one of the non-surgical SCS drug delivery methods provided herein. For example, in one embodiment, a patient in need of treatment is administered a drug formulation comprising an effective amount of a PCV treating drug to the SCS of one or both eyes. In a further embodiment, drug formulation administration is carried out with a microneedle device described herein. In even a further embodiment, the effective amount of the PCV treating drug comprises an effective amount of an anti-inflammatory drug, a vascular endothelial growth factor (VEGF) modulator, a platelet derived growth factor (PDGF) modulator, an angiogenesis inhibitor, an immunosuppressive agent or a vascular permeability inhibitor.

PCV is an abnormal choroidal vasculopathy that is believed to be a variant of type 1 neovascularization, although it has been proposed that PCV is a distinct vascular abnormality of choroidal vessels (Imamura et al. (2010). Survey of Ophthalmology, volume 55, pp. 501-515, incorporated by reference herein). PCV has been reported to occur at a higher frequency in pigmented races, although it has also been reported to be present in Caucasian patients. (Imamura et al. (2010). Survey of Ophthalmology, volume 55, pp. 501-515, incorporated by reference herein). The methods described herein are employable in patients of both pigmented and non-pigmented patients. For example, the patient receiving treatment for PCV, in one embodiment, is of African, Hispanic, Middle Eastern or Asian descent. In another embodiment, the patient receiving treatment is Caucasian.

Clinical manifestations of patients with PCV include vascular abnormalities and variably sized serous, serosanguineous detachments of the neurosensory retina and pigment epithelium around the optic nerve or in the central macula. Subretinal exudation and/or bleeding can also be experienced by patients with PCV. In another embodiment, the PCV patient has lipid depositions in the eye. The present invention provides for a reduction in occurrence and/or severity of a PCV clinical manifestation experienced by the PCV patient treated with the methods described herein, compared to the occurrence and/or severity of the clinical manifestation prior to treatment. For example, a patient receiving treatment for PCV with one of the non-surgical treatment methods provided herein, experiences a reduction in the occurrence and/or severity of a vascular abnormality, as compared to the occurrence and/or severity of the vascular abnormality manifested prior to undergoing treatment with the non-surgical SCS drug delivery method. In another embodiment, the severity of subretinal exudation and/or bleeding is reduced in the PCV patient, compared to the severity of the subretinal exudation and/or bleeding prior to undergoing treatment with one of the non-surgical SCS drug delivery methods described herein. PCV treating drugs, e.g., angiogenesis inhibitors, VEGF modulators, PDGF modulators, anti-inflammatory drugs, vascular permeability inhibitors, are described in more detail below.

In one embodiment, the patient being treated for PCV with one of the non-surgical methods described herein, is also treated for a second ocular disease. In a further embodiment, the additional ocular disease is drusen, sickle cell retinopathy, central serous chorioretinopathy, typical neovascular (type 1 or 2) age related macular degeneration, melanocytoma of the optic nerve, circumscribed choroidal hemangioma, the tilted disk syndrome, pathological myopia, choroidal osteoma, retinal microangiopathy. The treatment of the second ocular disease can be performed with the non-surgical SCS drug delivery methods described herein, or other methods known in the art, for example, intravitreal or topical drug administration.

In another embodiment, the method for treating a choroidal malady described herein, i.e., non-surgical drug delivery to the SCS of one or both eyes of the patient, is a method for treating a patient for central serous chorioretinopathy (CSC) (also known as central serous retinopathy (CSR)). CSR is an exudative chorioreditopathy, and is characterized by an exudative neurosensory retinal detachment with or without an associated detachment of the retinal pigment epithelium (RPE). CSR, in some instances, results in metamorphopsia and micropsia. In some instances, CSR is characterized by leakage of fluid under the retina. Additionally, patients with CSR often experience reduced visual acuity. In one embodiment, a method for treating a patient for CSR is provided, comprising non-surgically administering a drug formulation comprising an effective amount of a CSR treating drug to the SCS of one or both eyes of the patient. The drug is administered, in one embodiment, with one of the microneedles described herein. In a further embodiment, the CSR treating drug is an anti-inflammatory drug, a vascular endothelial growth factor (VEGF) modulator (e.g., a VEGF antagonist), a platelet derived growth factor (PDGF) modulator (e.g., a PDGF antagonist), an angiogenesis inhibitor, an immunosuppressive agent or a vascular permeability inhibitor. In a further embodiment, the patient treated for CSR by one of the methods described herein experiences an increase in visual acuity, compared to the patient's visual acuity prior to undergoing the treatment. In another embodiment, the patient, after undergoing treatment for CSR, experiences a decrease in leakage of fluid under the retina, compared to the leakage of fluid under the retina experienced by the patient prior to undergoing treatment via non-surgical SCS drug delivery.

In yet another embodiment, a method for treating a patient for multi-focal choroiditis (MFC) is provided. In one embodiment, the MFC treatment method comprises non-surgically administering a drug formulation comprising an effective amount of a MFC treating drug to the SCS of one or both eyes of the patient in need of MFC treatment. The drug formulation is administered, in one embodiment, with one of the microneedles described herein. In a further embodiment, the effective amount of the MFC treating drug comprises an effective amount of an anti-inflammatory drug, a vascular endothelial growth factor (VEGF) modulator (e.g., a VEGF antagonist), a platelet derived growth factor (PDGF) modulator (e.g., a PDGF antagonist), an angiogenesis inhibitor, an immunosuppressive agent or a vascular permeability inhibitor. The MFC patient, in one embodiment, is moderately myopic, and in one embodiment, is affected bilaterally. The MFC patient, in some embodiments, presents with symptoms of posterior uveitis including decreased visual acuity, floaters, photopsias, as well as with anterior segment symptoms such as photophobia. In one embodiment, the MFC patient presents with vitreous cell and/or anterior chamber cell. Funduscopic findings in MFC patients consist of yellow to gray lesions at the level of the retinal pigment epithelium (RPE) and choriocapillaris. The lesions range in size from about 50 µm to about 1,000 µm and have a distribution in the peripapillary region. The methods provided herein, in one embodiment, reduce the lesion size and/or number in the patient receiving treatment. Active lesions in some instances are associated with subretinal fluid and fluffy borders. Active disease may be also associated with optic nerve head hyperemia and edema, cystoid macular edema and macular and peripapillary choroidal neovascularization.

In one embodiment, the method for treating a patient for MFC comprises non-surgically administering a drug formulation comprising an effective amount of a MFC treating drug to the SCS of one or both eyes of the patient in need of treatment. In a further embodiment, the method comprises administration of the drug formulation to the SCS of one or both eyes of the patient with one of the microneedles described herein. For example, a drug formulation is delivered in one embodiment to the SCS of an eye of the patient via a hollow microneedle with a tip and an opening, through the opening and into the SCS. In a further embodiment, the effective amount of the MFC treating drug is an effective amount of an anti-inflammatory drug, angiogenesis inhibitor, VEGF modulator or vascular permeability inhibitor. In a further embodiment, the patient treated for MFC experiences a decreased number of lesion(s) (e.g., decreased number of lesion(s) in the RPE), decreased size of lesion(s) (e.g., decreased size of lesion(s) present in the RPE), decreased amount of subretinal fluid, an increase in visual acuity, or an attenuation in choroidal neovascularization, compared to the number of lesion(s), the size of lesion(s), amount of subretinal fluid, visual acuity and choroidal neovascularization in the eye of the patient, prior to undergoing the MFC treatment method of the invention. In another embodiment, the patient treated for MFC experiences an attenuation of optic nerve head hyperemia and edema, compared to the optic nerve head hyperemia and edema experienced by the patient prior to undergoing treatment via the non-surgical SCS drug delivery method of the invention.

In one embodiment, a patient in need of treatment of choroidal neovascularization is treated with one of the non-surgical SCS drug delivery methods provided herein. For example, in one embodiment, a patient in need of treatment is administered a drug formulation comprising an effective amount of a choroidal neovascularization treating drug to the SCS of one or both eyes. In a further embodiment, drug formulation administration is carried out with a microneedle device described herein. In one embodiment, the effective amount of the choroidal neovascularization treating drug is an anti-inflammatory drug, angiogenesis inhibitor, VEGF modulator, (e.g., a VEGF antagonist), a platelet derived growth factor (PDGF) modulator (e.g., a PDGF antagonist), an angiogenesis inhibitor, an immunosuppressive agent or a vascular permeability inhibitor.

In one embodiment, a patient in need of treatment of choroidal dystrophy is treated with one of the non-surgical SCS drug delivery methods provided herein. For example, in one embodiment, a patient in need of treatment is administered a drug formulation comprising an effective amount of a choroidal dystrophy treating drug to the SCS of one or both eyes. In a further embodiment, the effective amount of the choroidal dystrophy treating drug comprises an effective amount of an anti-inflammatory drug, a vascular endothelial growth factor (VEGF) modulator, a platelet derived growth factor (PDGF) modulator, an angiogenesis inhibitor, an immunosuppressive agent or a vascular permeability inhibitor. In a further embodiment, drug formulation administration is carried out with a microneedle device described herein. The choroidal dystrophy methods provided herein, in one embodiment, improve a symptom or clinical manifestation of the choroidal dystrophy to a greater extent, compared to the identical drug administered to the patient via a topical, oral, parenteral, intravitreal or intracameral route.

In yet another embodiment, the method for treating a choroidal malady described herein, i.e., a non-surgical SCS drug delivery method described herein, is a method for treating a patient for punctuate inner choroidopathy (PIC). In one embodiment, the method for treating a patient for PIC comprises non-surgically administering a drug formulation comprising an effective amount of a PIC treating drug to the SCS of one or two eyes of the patient. In a further embodiment, the method comprises drug delivery with one of the microneedles described herein. In one embodiment, the effective amount of the PIC treating drug is an anti-inflammatory drug, angiogenesis inhibitor, immunosuppressive agent, VEGF modulator (e.g., a VEGF antagonist), a PDGF modulator (e.g., a PDGF antagonist) or vascular permeability inhibitor.

In one embodiment, a PIC patient undergoing one of the SCS treatment methods provided herein experiences an improved PIC symptom/clinical manifestation, or a decreased number of PIC symptoms/clinical manifestations, compared to the symptoms/clinical manifestations experienced prior to SCS drug administration. In a further embodiment, the symptom/clinical manifestation is inflammation, blurred vision, photopsia, central and/or peripheral scotomatas or metamorphopsias. In another embodiment, the symptom/clinical manifestation is decreased visual acuity, bilateral white-yellow chorioretinal lesion(s) (e.g., from about 100 µm to about 200 µm in diameter) at the level of the inner choroid and retinal pigment epithelium. The lesion(s) typically is not associated with vitritis and typically does not extend to the midperiphery. PIC lesions progress to atrophic scars and leave a halo of depigmentation. In one embodiment, the PIC patient treated with one of the non-surgical SCS drug delivery methods described herein experiences decreased inflammation, a decreased number of lesion(s), or decreased size of lesion(s), as compared to the inflammation, number of lesion(s), or size of lesion(s) manifested by the patient prior to therapy. In another embodiment, PIC patient treated with one of the non-surgical SCS drug delivery methods described herein experiences decreased inflammation, a decreased number of lesion(s), or decreased size of lesion(s), as compared to the inflammation, number of lesion(s), or size of lesion(s) after intravitreal, oral, topical, parenteral or intracameral drug therapy with the same drug dose as administered to the SCS.

In one embodiment, the method for treating a choroidal malady described herein is a method for treating a patient for choroidal dystrophy. In one embodiment, the method for treating a patient for a choroidal dystrophy comprises non-surgically administering a drug formulation comprising an effective amount of a choroidal dystrophy treating drug to the SCS of one or both eyes of the patient in need of treatment. In a further embodiment, the method comprises delivering the drug formulation to the SCS of one or both eyes of the patient via a hollow microneedle having a tip and an opening. In a further embodiment, the effective amount of the choroidal dystrophy treating drug comprises an effective amount of an anti-inflammatory drug, a vascular endothelial growth factor (VEGF) modulator (e.g., a VEGF antagonist), a platelet derived growth factor (PDGF) modulator (e.g., a PDGF antagonist), an angiogenesis inhibitor, an immunosuppressive agent or a vascular permeability inhibitor. In one embodiment, the microneedle is inserted into the sclera and the drug formulation is infused into the SCS through the opening of the inserted microneedle. The choroidal dystrophy, in one embodiment, is central areolar choroidal dystrophy (CACD), central gyrate choroidal dystrophy, serpiginous choroidal dystrophy, or total central choroidal atrophy. In a further embodiment, the patient is treated for CACD, and the CACD is CACD1, CACD2 or CACD3. The CACD, in one embodiment, is with drusen. In another embodiment, the CACD is without drusen.

The choroidal dystrophy treatment methods provided herein, in one embodiment, decrease the number of choroidal dystrophy symptom(s) experienced by the patient prior to therapy. In another embodiment, the choroidal dystrophy treatment methods provided herein decrease the severity of choroidal dystrophy symptom(s) experienced by the patient prior to therapy.

In one embodiment of the choroidal malady treatment methods described herein—non-surgical delivery of a drug formulation comprising an effective amount of a choroidal malady treating drug, for example an effective amount of an anti-inflammatory drug (e.g., a steroidal compound or an NSAID), a vascular endothelial growth factor (VEGF) modulator (e.g., a VEGF antagonist), an immunosuppressive agent, an angiogenesis inhibitor (e.g., a platelet derived growth factor (PDGF) antagonist), or a vascular permeability inhibitor, to the SCS of one or both eyes of the patient in need of treatment, is achieved by inserting a microneedle into the eye of a patient, and infusing the drug into the SCS through the microneedle, or infused into the SCS via a coating on a solid or hollow microneedle. The solid or hollow microneedle, in one embodiment, is inserted into the sclera. In one embodiment, a hollow microneedle with a tip and an opening is inserted into the sclera, and the drug formulation is injected or infused through the inserted microneedle and into the suprachoroidal space of the eye. In another embodiment, a solid microneedle with an effective amount of a choroidal malady treating drug coated on the microneedle is inserted into the sclera, and the drug diffuses into the SCS of the eye of the patient.

The drug formulation delivered to the suprachoroidal space of the eye of a human subject for the treatment of a posterior ocular disorder or a choroidal malady, may be in the form of a liquid drug, a liquid solution that includes a drug in a suitable solvent, or liquid suspension. The liquid suspension may include microparticles or nanoparticles dispersed in a suitable liquid vehicle for infusion. In various embodiments, the drug is included in a liquid vehicle, in microparticles or nanoparticles, or in both the vehicle and particles. The drug formulation is sufficiently fluid to flow into and within the suprachoroidal space, as well as into the surrounding posterior ocular tissues. In one embodiment, the viscosity of the fluid drug formulation is about 1 cP at 37° C.

A wide range of drugs may be formulated for delivery to the suprachoroidal space and posterior ocular tissues with the present microneedle devices and methods. As used herein, the term "drug" refers to any prophylactic, therapeutic, or diagnostic agent, i.e., an ingredient useful for medical applications. The drug may be selected from small molecules, proteins, peptides and fragments thereof, which can be naturally occurring, synthesized or recombinantly produced. For example, in one embodiment, the drug delivered to the suprachoroidal space with the non-surgical methods described herein is an antibody or a fragment thereof (e.g., a Fab, Fv or Fc fragment). In certain embodiments, the drug is a sub-immunoglobulin antigen-binding molecule, such as Fv immunoglobulin fragment, minibody, diabody, and the like, as described in U.S. Pat. No. 6,773,916, incorporated herein by reference in its entirety for all purposes. In one embodiment, the drug is a humanized antibody or a fragment thereof.

In one embodiment, the drug is selected from a suitable oligonucleotide (e.g., antisense oligonucleotide agents), polynucleotide (e.g., therapeutic DNA), ribozyme, dsRNA, siRNA, RNAi, gene therapy vectors, and/or vaccine. In a further embodiment, the drug is an aptamer (e.g., an oligonucleotide or peptide molecule that binds to a specific target molecule). In another embodiment, the drug formulation delivered via the methods provided herein comprises a small molecule drug, an endogenous protein or fragment thereof, or an endogenous peptide or fragment thereof.

Representative examples of types of drugs for delivery to ocular tissues include anti-inflammatory drugs, including, but not limited to steroids, immunosuppressives, antimetabolites, T-cell inhibitors, alkylating agents, biologics, TNF antagonists (e.g., TNF-α antagonists), VEGF antagonists, and/or non-steroidal anti-inflammatory drugs (NSAIDs). Non-limiting examples of specific drugs and classes of drugs that can be delivered to the suprachoroidal space to treat posterior ocular disorders include miotics (e.g., pilocarpine, carbachol, physostigmine), sympathomimetics (e.g., adrenaline, dipivefrine), carbonic anhydrase inhibitors (e.g., acetazolamide, dorzolamide), VEGF antagonists, PDGF antagonists, NSAIDs, steroids, prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), aldose reductase inhibitors, anti-inflammatory and/or anti-allergy compounds (e.g., steroidal compounds such as triamcinolone, betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegaptanib sodium, ranibizumab, and bevacizumab.

As provided throughout, in some embodiments, methods of delivering a drug formulation comprising an effective amount of an angiogenesis inhibitor, an anti-inflammatory drug (e.g., a steroid or NSAID), a VEGF modulator (e.g., a VEGF antagonist), a PDGF modulator (e.g., a PDGF antagonist), an immunosuppressive agent or a vascular permeability inhibitor, to the SCS of an eye of a patient in need thereof are provided.

In one embodiment, the angiogenesis inhibitor is an integrin antagonist, a selectin antagonist, an adhesion molecule antagonist (e.g., antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1)), a basic fibroblast growth factor antagonist, a vascular endothelial growth factor (VEGF) modulator, or a platelet derived growth factor (PDGF) modulator (e.g., a PDGF antagonist). The integrin antagonist delivered via the methods described herein, in one embodiment, is a small molecule integrin antagonist, for example, an antagonist described by Paolillo et al. (Mini Rev Med Chem, 2009, volume 12, pp. 1439-1446, incorporated by reference in its entirety), or a leukocyte adhesion-inducing cytokine or growth factor antagonist (e.g., tumor necrosis factor-α (TNF-α), interleukin-1β (IL-1β), monocyte chemotactic protein-1 (MCP-1) and a vascular endothelial growth factor (VEGF)), as described in U.S. Pat. No. 6,524,581, incorporated by reference in its entirety herein. In another embodiment, the drug may be a diagnostic agent, such as a contrast agent, known in the art.

In one embodiment, the intraocular elimination half life ($t_{1/2}$) of the angiogenesis inhibitor administered to the SCS is greater than the intraocular $t_{1/2}$ of the angiogenesis inhibitor, when the identical dosage of the angiogenesis inhibitor is administered intravitreally, intracamerally, topically, parenterally or orally. In another embodiment, the mean intraocular maximum concentration ($C_{max}$) of the angiogenesis inhibitor, when the identical dosage of the angiogenesis inhibitor is administered to the SCS via the methods described herein, is greater than the intraocular $C_{max}$ of the angiogenesis inhibitor, when the identical dosage is administered intravitreally, intracamerally, topically, parenterally or orally. In another embodiment, the mean intraocular area under the curve ($AUC_{0-t}$) of the angiogenesis inhibitor when administered to the SCS via the methods described herein, is greater than the intraocular $AUC_{0-t}$ of the angiogenesis inhibitor, when the identical dosage of the angiogenesis inhibitor is administered intravitreally, intracamerally, topically, parenterally or orally.

The angiogenesis inhibitor delivered via the methods and devices described herein, in one embodiment, is interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *astragalus membranaceus* extract with *salvia* and schisandra *chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260 or XV615.

Specific endogenous angiogenesis inhibitors for delivery via the methods described herein include endostatin, a 20 kDa C-terminal fragment derived from type XVIII collagen, angiostatin (a 38 kDa fragment of plasmin), or a member of the thrombospondin (TSP) family of proteins. In a further embodiment, the angiogenesis inhibitor is a TSP-1, TSP-2, TSP-3, TSP-4 and TSP-5. Other endogenous angiogenesis inhibitors that are amenable for delivery via the choroidal malady treatment methods described herein include a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN) (e.g., IFN-α, IFN-β, IFN-γ), a chemokine, e.g., a chemokine having the C—X—C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin and proliferin-related protein.

In one embodiment, the angiogenesis inhibitor delivered via the methods described herein to treat a choroidal malady, is an antibody. In a further embodiment, the antibody is a humanized monoclonal antibody. In even a further embodiment, the humanized monoclonal antibody is bevacizumab.

In one embodiment, the non-surgical treatment methods and devices described herein may be used in gene-based therapy applications. For example, the method, in one embodiment, comprises administering a fluid drug formulation into the suprachoroidal space to deliver select DNA, RNA, or oligonucleotides to targeted ocular tissues.

In one embodiment, the drug is useful in treating a choroidal malady. In a further embodiment, the choroidal malady treating drug is a nucleic acid administered to inhibit gene expression. For example, the nucleic acid, in one embodiment, is a micro-ribonucleic acid (microRNA), a small interfering RNA (siRNA), a small hairpin RNA (shRNA) or a double stranded RNA (dsRNA), that targets a gene involved in angiogenesis. In one embodiment, the methods provided herein to treat a choroidal malady comprise administering an RNA molecule to the SCS of a patient in need thereof. In a further embodiment, the RNA molecule is delivered to the SCS via one of the microneedles described herein. In one embodiment, the patient is being treated for PCV, and the RNA molecule targets HTRA1, CFH, elastin or ARMS2, such that the expression of the targeted gene is downregulated in the patient, upon administration of the RNA. In a further embodiment, the targeted gene is CFH, and the RNA molecule targets a polymorphism selected from rs3753394, rs800292, rs3753394, rs6680396, rs1410996, rs2284664, rs1329428, and rs1065489. In another embodiment, the patient is being treated for a choroidal dystrophy, and the RNA molecule targets the PRPH2 gene. In a further embodiment, the RNA molecule targets a mutation in the PRPH2 gene.

In one embodiment, the drug delivered to the suprachoroidal space using the non-surgical methods (e.g., microneedle devices and methods) herein is sirolimus (Rapamycin®, Rapamune®). In one embodiment, the non-surgical drug delivery methods disclosed herein are used in conjunction with rapamycin to treat, prevent and/or ameliorate a wide range of diseases or disorders including, but not limited to: abdominal neoplasms, acquired immunodeficiency syndrome, acute coronary syndrome, acute lymphoblastic leukemia, acute myelocytic leukemia, acute non-lymphoblastic leukemia, adenocarcinoma, adenoma, adenomyoepithelioma, adnexal diseases, anaplastic astrocytoma, anaplastic large cell lymphoma, anaplastic plasmacytoma, anemia, angina pectoris, angioimmunoblastic lymphadenopathy with dysproteinemia, angiomyolipoma, arterial occlusive diseases, arteriosclerosis, astrocytoma, atherosclerosis, autoimmune diseases, B-cell lymphomas, blood coagulation disorders, blood protein disorders, bone cancer, bone marrow diseases, brain diseases, brain neoplasms, breast beoplasms, bronchial neoplasms, carcinoid syndrome, carcinoid Tumor, carcinoma, squamous cell carcinoma, central nervous system diseases, central nervous system neoplasms, choroid diseases, choroid plexus neoplasms, choroidal neovascularization, choroiditis, chronic lymphocytic leukemia, chronic myeloid leukemia, chronic myelomonocytic leukemia, chronic myeloproliferative disorders, chronic neutrophilic leukemia, clear cell renal cell carcinoma, colonic diseases, colonic neoplasms, colorectal neoplasms, coronary artery disease, coronary disease, coronary Occlusion, coronary restenosis, coronary stenosis, coronary thrombosis, cutaneous T-cell lymphoma, diabetes mellitus, digestive system neoplasms, dry eye syndromes, ear diseases, edema, endocrine gland neoplasms, endocrine system diseases, endometrial neoplasms, Endometrial stromal tumors, Ewing's sarcoma, exanthema, eye neoplasms, fibrosis, follicular lymphoma, gastrointestinal diseases, gastrointestinal neoplasms, genital neoplasms, glioblastoma, glioma, gliosarcoma, graft vs host disease, hematologic diseases, hematologic neoplasms, hemorrhagic disorders, hemostatic disorders, Hodgkin disease, Hodgkin lymphoma, homologous wasting disease, immunoblastic lymphadenopathy, immunologic deficiency syndromes, immunoproliferative disorders, infarction, inflammation, intestinal diseases, intestinal neoplasms, ischemia, kidney cancer, kidney diseases, kidney neoplasms, leukemia, B-Cell, leukemia, lymphoid, liver cancer, liver diseases, lung diseases, lymphatic diseases, lymphoblastic lymphoma, lymphoma, macular degeneration, macular edema, melanoma, mouth neoplasms, multiple myeloma, myelodysplastic syndromes, myelofibrosis, myeloproliferative disorders, neuroectodermal tumors, neuroendocrine tumors, neuroepithelioma, neurofibroma, renal cancer, respiratory tract diseases, retinal degeneration, retinal diseases, retinal neoplasms, retinoblastoma, rhabdomyosarcoma, thoracic neoplasms, uveitis, vascular diseases, Waldenstrom Macroglobulinemia, and wet macular degeneration. In addition, delivery of rapamycin using the microneedle devices and methods disclosed herein may be combined with one or more agents listed herein or with other agents known in the art.

In one embodiment, the angiogenesis inhibitor delivered to the suprachoroidal space using the non-surgical methods described herein is an antagonist of a member of the platelet derived growth factor (PDGF) family, for example, a drug that inhibits, reduces or modulates the signaling and/or activity of PDGF-receptors (PDGFR). For example, the PDGF antagonist delivered to the suprachoroidal space for the treatment of a choroidal malady, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

In one embodiment, the intraocular elimination half life ($t_{1/2}$) of the PDGF antagonist administered to the SCS is greater than the intraocular $t_{1/2}$ of the PDGF antagonist, when the identical dosage of the PDGF antagonist is administered intravitreally, intracamerally, topically, parenterally or orally. In another embodiment, the mean intraocular maximum concentration ($C_{max}$) of the PDGF antagonist, when administered to the SCS via the methods described herein, is greater than the intraocular $C_{max}$ of the PDGF antagonist, when the identical dosage of the PDGF antagonist is administered intravitreally, intracamerally, topically, parenterally or orally. In another embodiment, the mean intraocular area under the curve ($AUC_{0-t}$) of the PDGF antagonist, when administered to the SCS via the methods described herein, is greater than the intraocular $AUC_{0-t}$ of the PDGF antagonist, when the identical dosage of the PDGF antagonist is administered intravitreally, intracamerally, topically, parenterally or orally.

In certain embodiments, the drug delivered to the suprachoroidal space using the microneedle devices and methods disclosed herein is vascular endothelial growth factor (VEGF) modulator. For example, in one embodiment, the VEGF modulator is a VEGF antagonist. In one embodiment, the VEGF modulator is a VEGF-receptor kinase antagonist, an anti-VEGF antibody or fragment thereof, an anti-VEGF receptor antibody, an anti-VEGF aptamer, a small molecule VEGF antagonist, a thiazolidinedione, a quinoline or a designed ankyrin repeat protein (DARPin).

In one embodiment, the VEGF antagonist delivered via the non-surgical methods described herein is an antagonist of a VEGF receptor (VEGFR), i.e., a drug that inhibits, reduces, or modulates the signaling and/or activity of a VEGFR. The VEGFR may be a membrane-bound or soluble VEGFR. In a further embodiment, the VEGFR is VEGFR-1, VEGFR-2 or VEGFR-3. In one embodiment, the VEGF antagonist targets the VEGF-C protein. In another embodiment, the VEGF modulator is an antagonist of a tyrosine kinase or a tyrosine kinase receptor. In another embodiment, the VEGF modulator is a modulator of the VEGF-A protein. In yet another embodiment, the VEGF antagonist is a monoclonal antibody. In a further embodiment, the monoclonal antibody is a humanized monoclonal antibody.

In one embodiment, the intraocular elimination half life ($t_{1/2}$) of the VEGF antagonist administered to the SCS is greater than the intraocular $t_{1/2}$ of the VEGF antagonist, when the identical dosage of the VEGF antagonist is administered intravitreally, intracamerally, topically, parenterally or orally. In another embodiment, the mean intraocular maximum concentration ($C_{max}$) of the VEGF antagonist, when administered to the SCS via the methods described herein, is greater than the intraocular $C_{max}$ of the VEGF antagonist, when the identical dosage of the VEGF antagonist is administered intravitreally, intracamerally, topically, parenterally or orally. In another embodiment, the mean intraocular area under the curve ($AUC_{0-t}$) of the VEGF antagonist, when administered to the SCS via the methods described herein, is greater than the intraocular $AUC_{0-t}$ of the VEGF antagonist, when the identical dosage of the VEGF antagonist is administered intravitreally, intracamerally, topically, parenterally or orally.

In one embodiment, the non-surgical methods, needles and/or devices described herein are used to deliver one of the following VEGF modulators to the suprachoroidal space of the eye to treat one or more posterior ocular disorders or choroidal maladies described herein: AL8326, 2C3 antibody, AT001 antibody, HyBEV, bevacizumab (Avastin®), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, sunitinib malate (Sutent®), INDUS815C, R84 antibody, KDO19, NM3, allogenic mesenchymal precursor cells combined with an anti-VEGF antagonist (e.g., anti-VEGF antibody), MGCD265, MG516, VEGF-Receptor kinase inhibitor, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble Flt1 receptor, cediranib (Recentin™), AV-951, tivozanib (KRN-951), regorafenib (Stivarga®), volasertib (BI6727), CEP11981, KH903, lenvatinib (E7080), lenvatinib mesylate, teramemprocol (EM1421), ranibizumab (Lucentis®), pazopanib hydrochloride (Votrient™), PF00337210, PRS050, SP01 (curcumin), carboxyamidotriazole orotate, hydroxychloroquine, linifanib (ABT869, RG3635), fluocinolone acetonide (Iluvien®), ALG1001, AGN150998, DARPin MP0112, AMG386, ponatinib (AP24534), AVA101, nintedanib (Vargatefr™), BMS690514, KH902, golvatinib (E7050), everolimus (Afinitor®), dovitinib lactate (TKI258, CHIR258), ORA101, ORA102, axitinib (Inlyta®, AG013736), plitidepsin (Aplidin®), PTC299, aflibercept (Zaltrap®, Eylea®), pegaptanib sodium (Macugen™, LI900015), verteporfin (Visudyne®), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF antagonist using the microneedle devices and non-surgical methods disclosed herein may be combined with one or more agents listed herein or with other agents known in the art, either in a single or multiple formulations.

In one embodiment, delivery of a VEGF antagonist to the suprachoroidal space of the eye of a human subject using the microneedle devices and methods disclosed herein is used to treat, prevent and/or ameliorate one or more posterior ocular disorder or choroidal malady. For example, the posterior ocular disorder, in one embodiment, is a disease of the retina. In another embodiment, the posterior ocular disorder is a disease of the choroid. In yet another embodiment, the posterior ocular disorder is an optic nerve disease. In one embodiment, the posterior ocular disorder or disorder is selected from macular degeneration, age related macular degeneration, neovascular age-related macular degeneration, subfoveal neovascular age related macular degeneration, macular edema, macular edema following retinal vein occlusion, macular edema with retinal vein occlusion (RVO), diabetic macular edema, macular edema secondary to branch retinal vein occlusion, macular edema secondary to central retinal vein occlusion, branch retinal vein occlusion, central retinal vein occlusion, neovascularization, choroidal neovascularization, subfoveal choroidal neovascularization, visual impairment due to diabetic macular edema, diabetic retinopathy, dry eye syndrome (inflammation and corneal tissue damage of dry eye), retinal detachment, retinal disorders, retinitis pigmentosa, retinal vein occlusion, branch retinal vein occlusion, central retinal vein occlusion, myopia, pathological myopia, neurodegenerative diseases, ocular neovascularization, eye cancer, uveitis, glaucoma, scleritis, ocular sarcoidosis, optic neuritis, corneal ulcer, ocular autoimmune disorder, or retinitis.

In one embodiment, the methods provided herein to treat a choroidal malady (e.g., choroidal neovascularization, polyploidal choroidal vasculopathy, central sirrus choroidopathy, multi-focal choroidopathy) comprise administering to a patient in need thereof, a drug formulation comprising an effective amount of an anti-inflammatory drug to the suprachoroidal space of the eye of the patient In one embodiment, the drug delivered to the suprachoroidal space of the eye of a human patient via the non-surgical posterior ocular disorder or choroidal malady treatment methods described herein, reduces, inhibits, prevents and/or ameliorates inflammation, i.e., is an anti-inflammatory drug. In one embodiment, the drug formulation delivered to the SCS of an eye of a patient in need thereof via the methods described herein comprises an effective amount of an immunosuppressive agent. For example, in one embodiment, the immunosuppressive agent is a glucocorticoid, cytokine inhibitor, cytostatic, alkylating agent, anti-metabolite, folic acid analogue, cytotoxic antibiotic, interferon, opioid, T-cell receptor directed antibody or an IL-2 receptor directed antibody. In one embodiment, the immunosuppressive agent is an anti-metabolite and the anti-metabolite is a purine analog, pyrimidine analogue, folic acid analogue or a protein synthesis inhibitor. In another embodiment, the immunosuppressive agent is an interleukin-2 inhibitor (e.g., basiliximab or daclizumab). Other immunosuppressive agents amenable for use with the methods and formulations described herein include, but are not limited to cyclophosphamide, nitrosourea, methotrexate, azathioprine, mercaptopurine, fluorouracil, dactinomycin, anthracycline, mitomycin C, bleomycin, mithramycin, muromonab-CD3, cyclosporine, tacrolimus, sirolimus or mycophenolate. In one embodiment, the drug formulation comprises an effective amount mycophenolate.

In one embodiment, the intraocular elimination half life ($t_{1/2}$) of the immunosuppressive agent administered to the SCS is greater than the intraocular $t_{1/2}$ of the immunosuppressive agent, when the identical dosage of the immunosuppressive agent is administered intravitreally, intracamerally, topically, parenterally or orally. In another embodiment, the mean intraocular maximum concentration ($C_{max}$) of the immunosuppressive agent, when administered to the SCS via the methods described herein, is greater than the intraocular $C_{max}$ of the immunosuppressive agent, when the identical dosage of the immunosuppressive agent is administered intravitreally, intracamerally, topically, parenterally or orally. In another embodiment, the mean intraocular area under the curve ($AUC_{0-t}$) of the immunosuppressive agent, when administered to the SCS via the methods described herein, is greater than the intraocular $AUC_{0-t}$ of the immunosuppressive agent, when the identical dosage of the immunosuppressive agent is administered intravitreally, intracamerally, topically, parenterally or orally.

In one embodiment, the drug formulation delivered to the SCS of an eye of a patient in need thereof via the methods described herein comprises an effective amount of vascular permeability inhibitor. In one embodiment, the vascular permeability inhibitor is a vascular endothelial growth factor (VEGF) antagonist or an angiotensin converting enzyme (ACE) inhibitor. In a further embodiment, the vascular permeability inhibitor is an angiotensin converting enzyme (ACE) inhibitor and the ACE inhibitor is captopril.

In one embodiment, the intraocular elimination half life ($t_{1/2}$) of the vascular permeability inhibitor administered to the SCS is greater than the intraocular $t_{1/2}$ of the vascular permeability inhibitor, when the identical dosage of the vascular permeability inhibitor is administered intravitreally, intracamerally, topically, parenterally or orally. In another embodiment, the mean intraocular maximum concentration ($C_{max}$) of the vascular permeability inhibitor, when administered to the SCS via the methods described herein, is greater than the intraocular $C_{max}$ of the vascular permeability inhibitor, when the identical dosage of the vascular permeability inhibitor is administered intravitreally, intracamerally, topically, parenterally or orally. In another embodiment, the mean intraocular area under the curve ($AUC_{0-t}$) of the vascular permeability inhibitor, when administered to the SCS via the methods described herein, is greater than the intraocular $AUC_{0-t}$ of the vascular permeability inhibitor, when the identical dosage of the vascular permeability inhibitor is administered intravitreally, intracamerally, topically, parenterally or orally.

In one embodiment, the drug is a steroid or a non-steroid anti-inflammatory drug (NSAID). In another embodiment, the anti-inflammatory drug is an antibody or fragment thereof, an anti-inflammatory peptide(s) or an anti-inflammatory aptamer(s). As provided throughout the specification, the delivery of the anti-inflammatory drug to the suprachoroidal space results in benefits over administration of the same drug delivered via oral, intravitreal, intracameral, topical and/or a parenteral route of administration. For example, in one embodiment, the therapeutic effect of the drug delivered to the suprachoroidal space is greater than the therapeutic effect of the same drug, delivered at the same dosage, when the drug is delivered via oral, intravitreal, topical or parenteral route. In one embodiment, the intraocular elimination half life ($t_{1/2}$) of the anti-inflammatory drug administered to the SCS is greater than the intraocular $t_{1/2}$ of the anti-inflammatory drug, when the identical dosage of the anti-inflammatory drug is administered intravitreally, intracamerally, topically, parenterally or orally. In another embodiment, the mean intraocular maximum concentration ($C_{max}$) of the anti-inflammatory drug, when administered to the SCS via the methods described herein, is greater than the intraocular $C_{max}$ of the anti-inflammatory drug, when administered intravitreally, intracamerally, topically, parenterally or orally. In another embodiment, the mean intraocular area under the curve ($AUC_{0-t}$) of the anti-inflammatory drug, when administered to the SCS via the methods described herein, is greater than the intraocular $AUC_{0-t}$ of the anti-inflammatory drug, when the identical dosage of the anti-inflammatory drug is administered intravitreally, intracamerally, topically, parenterally or orally.

Steroidal compounds that can be administered via the methods provided herein include hydrocortisone, hydrocortisone-17-butyrate, hydrocortisone-17-aceponate, hydrocortisone-17-buteprate, cortisone, tixocortol pivalate, prednisolone, methylprednisolone, prednisone, triamcinolone, triamcinolone acetonide, mometasone, amcinonide, budesonide, desonide, fluocinonide, halcinonide, bethamethasone, bethamethasone dipropionate, dexamethasone, fluocortolone, hydrocortisone-17-valerate, halometasone, alclometasone dipropionate, prednicarbate, clobetasone-17-butyrate, clobetasol-17-propionate, fluocortolone caproate, fluocortolone pivalate, fluprednidene acetate and prednicarbate.

Specific classes of NSAIDs that can be administered via the methods provided herein include, salicylates, propionic acid derivatives, acetic acid derivatives, enolic acid derivatives, fenamic acid derivatives and cyclooxygenase-2 (COX-2) inhibitors. In one embodiment, the methods provided herein are used to deliver one or more of the following NSAIDs to the SCS of an eye of a patient in need thereof: acetylsalicylic acid, diflunisal, salsalate, ibuprofen, dexibuprofen, naproxen, fenoprofen, keotoprofen, dexketoprofen, flurbiprofen, oxaprozin, loxaprofen, indomethacin, tolmetin, sulindac, etodolac, ketorolac, diclofenac or nabumetone, piroxicam, meloxicam, tenoxicam, droxicam, lornoxicam or isoxicam, mefanamic acid, meclofenamic acid, flufenamic acid, tolfenamic acid, celecoxib, refecoxib, valdecoxib, parecoxib, lumiracoxib, etoricoxib or firocoxib.

Other examples of anti-inflammatory drugs, that can be used in the methods provided herein to treat a posterior ocular disorder or a choroidal malady, choroidal neovascularization, or subretinal exudation, include, but are not limited to: mycophenolate, remicase, nepafenac, 19AV agonist(s), 19GJ agonists, 2MD analogs, 4SC101, 4SC102, 57-57, 5-HT2 receptor antagonist, 64G12, A804598, A967079, AAD2004, AB1010, AB224050, abatacept, etaracizumab (Abegrin™), Abevac®, AbGn134, AbGn168, Abki, ABN912, ABR215062, ABR224050, cyclosporine (Abrammune®), docosanol (behenyl alcohol, Abreva®), ABS15, ABS4, ABS6, ABT122, ABT325, ABT494, ABT874, ABT963, ABXIL8, ABXRB2, AC430, Accenetra, lysozyme chloride (Acdeam®), ACE772, aceclofenac (Acebloc, Acebid, Acenac), acetaminophen, chlorzoxazone, serrapeptase, tizanidine hydrochloride, betadex, Aceclogesic Plus, Aceclon, Acecloren, Aceclorism, acecrona, Aceffein, acemetacin, asprin (Acenterine), Acetal-SP (Aceclofenac—combination, ibuprofen, Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTSS inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzumab, Alequel™, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, alpha-1-antitrypsin, α2β1 integrin inhibitors, Alphacort, Alphafen, alpha-hexidine, alpha-trypsin, Alphintern, Alpinamed mobility omega 3, Alpoxen, AL-Rev 1, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, diclofenac (Emifenac®), Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA™ (therapeutic peptide vaccine), Anflene, ANG797, Anilixin, Anmerushin, Annexin 1 peptides, annexin A5, Anodyne, Ansaid, Anspirin, Antarene, anti BST2 antibody, anti C5a MAb, anti ILT7 antibody, anti VLA1 antibody, anti-alpha11 antibody, anti-CD4 802-2, anti-CD86 monoclonal antibody, anti-chemokine, anti-DC-SIGN, anti-HMGB-1 MAb, anti-IL-18 Mab, anti-IL-1R MAb, anti-IL-1R MAb, anti-IL23 BRISTOL, anti-interleukin-1β antibody, anti-LIGHT antibody, anti-MIF antibody, anti-MIF antibody, anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN inhibitor, apo-azathioprine, Apo-dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, aeterna shark cartilage extract (Arthrovas™, Neoretna™, Psovascar™) Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATIO03, atiprimod, ATL1222, ATN103, ATN192, ATR107, Atri, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason,
Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BRO2001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, *candida albicans* antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, CaspaCIDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 antagonist, CCR6 inhibitor, CCR7 antagonist, CCRL2 antagonist, CCX025, CCX354, CCX634, CD Diclofenac, CD102, CD103 antibody, CD103 antibody, CD137 antibody, CD16 antibody, CD18 antibody, CD19 antibody, CD1d antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CellCept, Cellmune, Celosti, Celoxib, Celprot, Celudex, ceniciviroc mesylate, cenplace1-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN15051, CGEN15091, CGEN25017, CGEN25068, CGEN40, CGEN54, CGEN768, CGEN855, CGI1746, CGI560, CGI676, Cgtx-Peptides, CH1504, CH4051, CH4446, chaperonin 10, chemokine C-C motif ligand 2, chemokine C-C motif ligand 2 antibody, chemokine C-C motif ligand 5 antibody, chemokine C-C motif receptor 2 antibody, chemokine C-C motif receptor 4 antibody, chemokine C-X-C motif ligand 10 antibody, chemokine C-X-C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CNDO201, CNI1493, CNTO136, CNTO148, CNTO1959, Cobefen, CoBenCoDerm, Cobix, Cofenac, Cofenac, COG241, COL179, colchicine, *Colchicum* Dispert, Colchimax, Colcibra, Coledes A, Colesol, Colifoam, Colirest, collagen, type V, Comcort, complement component (3b/4b) receptor 1, Complement Component C1s Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM ion channel inhibitor, Cratisone, CRB15, CRC4273, CRC4342, C-reactive protein 2-methoxyethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013IL1bQb, CYT015IL17Qb, CYT020TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone prednisolone (Deltacortril), Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermol, Dermolar, Dermonate, Dermosone, Dersone, Desketo, desonide, desoxycorticosterone acetate, Deswon, Dexa, Dexabene, Dexacip, Dexacort, dexacortisone, Dexacotisil, dexadic, dexadrin, Dexadron, Dexafar, Dexahil, Dexalab, Dexalaf, Dexalet, Dexalgen, dexallion, dexalocal, Dexalone, Dexa-M, Dexamecortin, Dexamed, Dexamedis, dexameral, Dexameta, dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Dolofit, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcomethacin, Farnerate, Farnezone, Farnezone, Farotrin, fas antibody, Fastflam, FasTRACK, Fastum, Fauldmetro, FcgammaRlA antibody, FE301, Febrofen, Febrofid, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Iminoral, Immodin, IMMU103, IMMU106, Immucept, Immufine, Immunex Syrup, immunoglobulin, immunoglobulin G, Immunoprin, ImmunoRel, Immurin, IMO8400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, INO7997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, Iomab B, IOR-T3, IP751, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IW001, Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketoplus Kata Plasma, ketoprofen, Ketores, Ketorin, ketorolac, ketorolac trometh-amine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv1.3 Blocker, Kv1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LE015520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafluo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lorncrat, lornoxicam, Lorox, losmapimod, loteprednol etabonate, Loteprednol, Lotirac, Low Molecular *Ganoderma Lucidum* Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxy12, Maxy30, MAXY4, Maxy735, Maxy740, Mayfenamic, MB11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alphaluminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, NewGam, Newmafen, Newmatal, Newsicam, NEX1285, sFcRIIB, Nextomab, NF-kappaB Inhibitor, NF-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCS5, NPRCS6, NPS3, NPS4, nPTery, NU3450, nuclear factor NF-kappa-B p65 subunit oligonucleotide, Nucort, Nulojix, Numed-Plus, Nurokind Ortho, Nusone-H, Nutrikemia, Nuvion, NV07alpha, NX001, Nyclobate, Nyox, Nysa, Obarcort, OC002417, OC2286, ocaratuzumab, OCTSG815, Oedemase, Oedemase-D, ofatumumab, Ofgyl-O, Ofvista, OHR118, OKi, Okifen, Oksamen, Olai, olokizumab, Omeprose E, Omnacortil, Omneed, Omniclor, Omnigel, Omniwel, onercept, ON04057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, Oral-Fenac, Oralog, Oralpred, Ora-sed, Orasone, orBec, Orbone forte, Orcl, ORE10002, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PH5, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasca, prednisolone, Deltacortril (prednisolone), prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix *Isatidis*, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade® (infliximab), Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, S1P Receptor Agonists, S1P Receptor Modulators, S1P1 Agonist, S1P1 receptor agonist, 52474, 53013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SB1087, SC080036, SC12267, SC409, Scaflam, SCD ketoprofen, SCIO323, SCIO469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, SI615, SI636, Sigmasporin, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SNO030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSS07 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Sterio, Sterisone, Steron, stichodactyla *helianthus* peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarenac, tarenflurbil, Tarimus, Tarproxen, Tauxib, Tazomust, TBR652, TC5619, T-cell, immune regulator 1, ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypeptides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamily1B oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Valdez, Valdixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, Venimmun N, Venoforte, Venoglobulin-IH, Venozel, Veral, Verax, vercirnon, vero-dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VRS826, VT111, VT214, VT224, VT310, VT346, VT362, VTX763, Vurdon, VX30 antibody, VX467, VXS, VX509, VX702, VX740, VX745, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XToll, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In one embodiment, the anti-inflammatory drug is non-surgically delivered to the suprachoroidal space of the eye using the microneedle devices and methods disclosed herein, and is used to treat, prevent and/or ameliorate a posterior ocular disorder in a human patient in need thereof. For example, the posterior ocular disorder or disorder selected from macular degeneration (e.g., age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, subfoveal wet age-related macular degeneration, and Vitreomacular Adhesion (VMA) associated with neovascular age related macular degeneration), macular edema, diabetic macular edema, uveitis, scleritis, chorioretinal inflammation, chorioretinitis, choroiditis, retinitis, retinochoroiditis, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated reinochoroiditis, posterior cyclitis, Harada's disease, chorioretinal scars (e.g., macula scars of posterior pole, solar retinopathy), choroidal degeneration (e.g., atrophy, sclerosis), hereditary choroidal dystrophy (e.g., choroidermia, choroidal dystrophy, gyrate atrophy), choroidal hemorrhage and rupture, choroidal detachment, retinal detachment, retinoschisis, hypersentitive retinopathy, retinopathy, retinopathy of prematurity, epiretinal membrane, peripheral retinal degeneration, hereditary retinal dystrophy, retinitis pigmentosa, retinal hemorrhage, separation of retinal layers, central serous retinopathy, glaucoma, ocular hypertension, glaucoma suspect, primary open-angle glaucoma, primary angle-closure glaucoma, floaters, Leber's hereditary optic neropathy, optic disc drusen, cinflammatory disorders of the eye, inflammatory lesions in fungal infections, inflammatory lesions, inflammatory pain, inflammatory skin diseases or disorders, Sjogren's syndrome, opthalmic for Sjogren's syndrome.

In one embodiment, the drug delivered to the suprachoroidal space using the non-surgical methods described herein is an antagonist of a member of the platelet derived growth factor (PDGF) family, for example, a drug that inhibits, reduces or modulates the signaling and/or activity of PDGF-receptors (PDGFR). For example, the PDGF antagonist delivered to the suprachoroidal space for the treatment of one or more posterior ocular disorders or choroidal maladies, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFRα or PDGFRβ. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, Dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869). In one embodiment, the intraocular elimination half life ($t_{1/2}$) of the PDGF antagonist administered to the SCS is greater than the intraocular $t_{1/2}$ of the PDGF antagonist, when administered intravitreally, intracamerally, topically, parenterally or orally. In another embodiment, the mean intraocular maximum concentration ($C_{max}$) of the PDGF antagonist, when administered to the SCS via the methods described herein, is greater than the intraocular $C_{max}$ of the PDGF antagonist, when administered intravitreally, intracamerally, topically, parenterally or orally. In another embodiment, the mean intraocular area under the curve ($AUC_{0-t}$) of the PDGF antagonist, when administered to the SCS via the methods described herein, is greater than the intraocular $AUC_{0-t}$ of the PDGF antagonist, when administered intravitreally, intracamerally, topically, parenterally or orally.

In one embodiment, the drug non-surgically delivered to the suprachoroidal space using devices and methods disclosed herein treats, prevents, and/or ameliorates the posterior ocular disorder macular degeneration, or a disease or disorder associated with macular degeneration. In one embodiment, the method described herein is used to treat or ameliorate age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, Subfoveal wet age-related macular degeneration or vitreomacular adhesion (VMA) associated with neovascular age related macular degeneration in a human patient in need of treatment.

Examples of drugs that treat, prevent and/or ameliorate macular degeneration that can be delivered to the suprachoroidal space via the devices and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, sub-family A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNTO2476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, bevacizumab, ranibizumab, triamcinolone, triamcinolone acetonide, triamcinolone acetonide with verteporfin, dexamethasone, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with ranibizumab (Lucentis®), iCo-008, Icon1, I-Gold, Ilaris, Iluvien, Iluvien with Lucentis, immunoglobulins, integrin alpha5beta1 immunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with *myrtillus* extract, Lutein with zeaxanthin, M200, M200 with Lucentis, Macugen, MC1101, MCT355, mecamylamine, Microplasmin, motexafin lutetium, MP0112, NADPH oxidase inhibitors, aeterna shark cartilage extract (Arthrovas™, Neoretna™, Psovascar™), neurotrophin 4 gene, Nova21012, Nova21013, NT501, NT503, Nutri-Stulln, ocriplasmin, OcuXan, Oftan Macula, Optrin, ORA102 with bevacizumab (Avastin®), P144, P17, Palomid 529, PAN90806, Panzem, Panzem, PARP inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumabwith verteporfin, ranibizumab with voloximab, RD27, Rescula, Retaane, retinal pigment epithelial cells, RetinoStat, RG7417, RN6G, RT101, RTU007, SB267268, serpin peptidase inhibitor, clade F, member 1 gene, shark cartilage extract, Shef1, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TKI, TLCx99, TRC093, TRC105, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF antagonist (e.g., as described herein), verteporfin, Visudyne, Visudyne with Lucentis and dexamethasone, Visudyne with triamcinolone acetonide, Vivis, voloximab, Votrient, XV615, zeaxanthin, ZFP TF, zinc-monocysteine and Zybrestat. In one embodiment, one or more of the macular degeneration treating drugs described above is combined with one or more agents listed above or herein or with other agents known in the art.

In one embodiment, the methods and devices provided herein are used to delivery triamcinolone or triamcinolone acetonide to the suprachoroidal space of an eye of a human subject in need of treatment of a posterior ocular disorder or choroidal malady. In a further embodiment, the triamcinolone or triamcinolone acetonide is delivered for the treatment of sympathetic ophthalmia, temporal arteritis, uveitis and/or other posterior ocular inflammatory conditions. In one embodiment, triamcinolone or triamcinolone acetonide is delivered to the suprachoroidal space of the eye of a human subject in need of treatment of sympathetic opthalmia with the methods and devices described herein. In another embodiment, triamcinolone or triamcinolone acetonide is delivered to the suprachoroidal space of the eye in a human subject in need of treatment of temporal arteritis with the methods and devices described herein. In yet another embodiment, triamcinolone or triamcinolone acetonide is delivered to the suprachoroidal space of the eye in a human subject in need of treatment of uveitis, with the methods and devices described herein. In another embodiment, triamcinolone or triamcinolone acetonide is delivered to the suprachoroidal space of the eye in a human subject in need of treatment of one or more posterior ocular inflammatory conditions, with the methods and devices described herein. In another embodiment, triamcinolone or triamcinolone acetonide is delivered via one of the methods described herein.

The triamcinolone composition provided herein, in one embodiment, is a suspension comprising microparticles or nanoparticles of triamcinolone or triamcinolone acetonide. The microparticles, in one embodiment, have a $D_{50}$ of about 3 μm or less. In a further embodiment, the $D_{50}$ is about 2 μm. In another embodiment, the $D_{50}$ is about 2 μm or less. In even another embodiment, the $D_{50}$ is about 1000 nm or less. The microparticles, in one embodiment, have a $D_{99}$ of about 10 μm or less. In another embodiment, the $D_{99}$ is about 10 μm. In another embodiment, the $D_{99}$ is about 10 μm or less, or about 9 μm or less.

In one embodiment, triamcinolone is present in the composition at from about 1 mg/mL to about 400 mg/mL. In a further embodiment, triamcinolone is present in the composition at from about 2 mg/mL to about 300 mg/mL. In a further embodiment, triamcinolone is present in the composition at from about 5 mg/mL to about 200 mg/mL. In a further embodiment, triamcinolone is present in the composition at from about 10 mg/mL to about 100 mg/mL. In a further embodiment, triamcinolone is present in the composition at from about 20 mg/mL to about 75 mg/mL. In a further embodiment, triamcinolone is present in the composition at from about 30 mg/mL to about 50 mg/mL. In one embodiment, triamcinolone is present in the composition at about 10, about 20, about 25, about 30, about 35, about 40, about 45, about 50, about 55 about 60, or about 75 mg/mL. In one embodiment, triamcinolone is present in the composition at about 40 mg/mL.

In one embodiment, the triamcinolone composition comprises sodium chloride. In another embodiment, the triamcinolone composition comprises carboxymethylcellulose sodium.

In one embodiment, the triamcinolone composition comprises triamcinolone microparticles. In a further embodiment, the composition comprises polysorbate 80. In another embodiment, the triamcinolone composition comprises one or more of $CaCl_2$, $MgCl_2$, sodium acetate and sodium citrate. In one embodiment, the composition comprises polysorbate 80 at a w/v % of 0.02% or about 0.02%, 0.015% or about 0.015%.

In one embodiment, the pH of the composition is from about 5.0 to about 8.5. In a further embodiment, the pH of the composition is from about 5.5 to about 8.0. In a yet further embodiment, the pH of the composition os from about 6.0 to about 7.5

In another aspect, the present invention provides a method for diagnosing a patient for a choroidal malady. In one embodiment, the method comprises administering a choroidal malady diagnostic agent to the SCS of one or both eyes of the patient, visualizing the diagnostic agent, and making a determination based on the visualization whether the patient has the choroidal malady. In a further embodiment, the diagnostic agent is delivered to the SCS of one or both eyes of the patient via one of the microneedles described herein.

In one embodiment, a method is provided for diagnosing a patient for a choroidal malady. The method comprises administering to the SCS of one or both eyes of the patient, an indocyanine green (ICG) molecule. The ICG molecule is stimulated by the absorption of infrared light in the range from about 790 nm to about 805 nm. The ICG molecule allows for visualization of the choroidal vasculatures. In one embodiment, a positive diagnosis of a choroidal malady is provided when pulsatile polypoidal vessels are visualized in the macula. In a further embodiment, the choroidal malady is PCV.

In one embodiment, as provided above, one or more drugs provided herein are delivered to the suprachoroidal space of the eye of a patient in need thereof, for the treatment of one or more posterior ocular disorders or choroidal maladies, using the microneedle devices and methods disclosed herein treats, prevents, and/or ameliorates fibrosis in the posterior segment of the eye (e.g. myelofibrosis, fibrosis in diabetic nephropathy, cystic fibrosis, scarring, and skin fibrosis).

In one embodiment, as provided above, one or more drugs provided herein are delivered to the suprachoroidal space of the eye of a patient in need thereof, for the treatment of choroidal malady, using the microneedle devices and methods disclosed herein treats, prevents, and/or ameliorates choroidal dystrophy.

In one embodiment, a drug that treats, prevents and/or ameliorates fibrosis is used in conjunction with the devices and methods described herein and is delivered to the suprachoroidal space of the eye. In a further embodiment, the drug is interferon gamma 1b (Actimmune®) with pirfenidone, ACUHTR028, AlphaVBeta5, aminobenzoate potassium, amyloid P, ANG1122, ANG1170, ANG3062, ANG3281, ANG3298, ANG4011, Anti-CTGF RNAi, Aplidin, *astragalus membranaceus* extract with *salvia* and schisandra *chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In one embodiment, one or more of the fibrosis treating drugs described above is combined with one or more agents listed above or herein or with other agents known in the art.

In one embodiment, a drug that treats, prevents and/or ameliorates diabetic macular edema is used in conjunction with the devices and methods described herein and is delivered to the suprachoroidal space of the eye. In a further embodiment, the drug is AKB9778, bevasiranib sodium, Candy, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or Tri-Lipix. In one embodiment, one or more of the diabetic macular edema treating drugs described above is combined with one or more agents listed above or herein or with other agents known in the art.

In one embodiment, a drug that treats, prevents and/or ameliorates macular edema is used in conjunction with the devices and methods described herein and is delivered to the suprachoroidal space of the eye. In a further embodiment, the drug is delivered to the suprachoroidal space of a human subject in need of treatment of a posterior ocular disorder or choroidal malady via a hollow microneedle. In one embodiment, the drug is denufosol tetrasodium, dexamethasone, ecallantide, pegaptanib sodium, ranibizumab or triamcinolone. In addition, the drugs delivered to ocular tissues using the microneedle devices and methods disclosed herein which treat, prevent, and/or ameliorate macular edema, as listed above, may be combined with one or more agents listed above or herein or with other agents known in the art.

In one embodiment, a drug that treats, prevents and/or ameliorates ocular hypertension is used in conjunction with the devices and methods described herein and is delivered to the suprachoroidal space of the eye. In a further embodiment, the drug is 2-MeS-beta gamma-CC12-ATP, Aceta Diazol, acetazolamide, Aristomol, Arteoptic, AZD4017, Betalmic, betaxolol hydrochloride, Betimol, Betoptic S, Brimodin, Brimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortinol, Glaumol, Hypadil, Ismotic, isopropyl unoprostone, isosorbide, Latalux, latanoprost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to the suprachoroidal space using the microneedle devices and methods disclosed herein which treat, prevent, and/or ameliorate ocular hypertension, as listed above, may be combined with one or more agents listed above or herein or with other agents known in the art.

The drug delivered to the suprachoroidal space via the non-surgical methods described herein, is present as a drug formulation. The "drug formulation" in one embodiment, is an aqueous solution or suspension, and comprises an effective amount of the drug. Accordingly, in some embodiments, the drug formulation is a fluid drug formulation. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In one embodiment, the drug formulation (e.g., fluid drug formulation) includes microparticles or nanoparticles, either of which includes at least one drug. Desirably, the microparticles or nanoparticles provide for the controlled release of drug into the suprachoroidal space and surrounding posterior ocular tissue. As used herein, the term "microparticle" encompasses microspheres, microcapsules, microparticles, and beads, having a number average diameter of from about 1 μm to about 100 μm, for example from about 1 to about 25 μm, or from about 1 μm to about 7 μm. "Nanoparticles" are particles having an average diameter of from about 1 nm to about 1000 nm. The microparticles, in one embodiment, have a $D_{50}$ of about 3 μm or less. In a further embodiment, the $D_{50}$ is about 2 μm. In another embodiment, the $D_{50}$ of the particles in the drug formulation is about 2 μm or less. In another embodiment, the $D_{50}$ of the particles in the drug formulation is about 1000 nm or less. In one embodiment, the drug formulation comprises microparticles having a $D_{99}$ of about 10 μm or less. The microparticles, in one embodiment, have a $D_{50}$ of about 3 μm or less. In a further embodiment, the $D_{50}$ is about 2 μm. In another embodiment, the $D_{50}$ of the particles in the drug formulation is about 2 μm or less. In another embodiment, the $D_{50}$ of the particles in the drug formulation is about 1000 nm or less. In one embodiment, the drug formulation comprises microparticles having a $D_{99}$ of about 10 μm or less. The microparticles, in one embodiment, have a $D_{50}$ of about 3 μm or less. In a further embodiment, the $D_{50}$ is about 2 μm. In another embodiment, the $D_{50}$ of the particles in the drug formulation is about 2 μm or less. In another embodiment, the $D_{50}$ of the particles in the drug formulation is about 100 nm to about 1000 nm. In one embodiment, the drug formulation comprises microparticles having a $D_{99}$ of about 1000 nm to about 10 μm. The microparticles, in one embodiment, have a $D_{50}$ of about 1 μm to about 5 μm or less. In another embodiment, the drug formulation comprises particles having a $D_{99}$ of about 10 In another embodiment, the $D_{99}$ of the particles in the formulation is less than about 10 or less than about 9 or less than about 7 μm or less than about 3 μm. In a further embodiment, the microparticles or nanoparticles comprise an anti-inflammatory drug. In a further embodiment, the anti-inflammatory drug is triamcinolone.

Microparticles and nanoparticles may or may not be spherical in shape. "Microcapsules" and "nanocapsules" are defined as microparticles and nanoparticles having an outer shell surrounding a core of another material. The core can be liquid, gel, solid, gas, or a combination thereof. In one case, the microcapsule or nanocapsule may be a "microbubble" or "nanobubble" having an outer shell surrounding a core of gas, wherein the drug is disposed on the surface of the outer shell, in the outer shell itself, or in the core. (Microbubbles and nanobubles may be respond to acoustic vibrations as known in the art for diagnosis or to burst the microbubble to release its payload at/into a select ocular tissue site.) "Microspheres" and "nanospheres" can be solid spheres, can be porous and include a sponge-like or honeycomb structure formed by pores or voids in a matrix material or shell, or can include multiple discrete voids in a matrix material or shell. The microparticles or nanoparticles may further include a matrix material. The shell or matrix material may be a polymer, amino acid, saccharride, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In one embodiment, the drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one which undergoes a phase change upon administration. For instance, a liquid drug formulation may be injected through hollow microneedles into the suprachoroidal space, where it then gels and the drug diffuses out from the gel for controlled release.

As described above, the drugs delivered to the suprachoroidal space via the methods described herein, i.e., for the treatment of one or more posterior ocular disorders or choroidal maladies, can be administered with one or more additional drugs. The one or more additional drugs, in one embodiment, are present in the same formulation as the first posterior ocular disorder treating drug or the choroidal malady treating drug. In another embodiment, the one or more additional drugs are delivered intravitreally, orally, topically or parenterally to the human subject in need of treatment of the posterior ocular disorder or choroidal malady. In one embodiment, a VEGF antagonist is delivered to the suprachoroidal space of the eye of a human subject in need of treatment of a posterior ocular disorder or choroidal malady via one of the methods disclosed herein, in conjunction with a PDGF antagonist. The PDGF antagonist is administered, for example, intravitreally, or to the suprachoroidal space. In another embodiment, a PDGF antagonist is delivered to the suprachoroidal space of the eye of a human subject via the methods described herein, in conjunction with a VEGF antagonist. The PDGF antagonist and VEGF antagonist can be administered in the same formulation or separate formulations.

In addition to suprachoroidal delivery, the one or more additional drugs delivered to the human subject can be delivered via intravitreal (IVT) administration (e.g., intravitreal injection, intravitreal implant or eye drops). Methods of IVT administration are well known in the art. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Cand5, CERE140, Ciganclor, CLT001, CLT003, CLT004, CLT005, complement component 5 aptamer (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimumab, LFG316, Lucentis, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptamer (pegylated), POT4, PRM167, PRS055, QPI1007, ranibizumab, resveratrol, Retilone, retinal pigment epithelium-specific protein 65 kDa gene, Retisert, rod derived cone viability factor, RPE65 Gene Therapy, RPGR Gene Therapy, RTP801, Sd-rxRNA, serpin peptidase inhibitor clade F member 1 gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, volocix-imab, Votrient, XG102, Xibrom, XV615, and Zybrestat. Accordingly, the methods of the present invention include administrating via IVT one or more of the drugs listed above in combination with one or more drugs disclosed herein administered into the suprachoroidal space using the microneedle device described herein.

EXAMPLES

The present invention is further illustrated by reference to the following Examples. However, it should be noted that these Examples, like the embodiments described above, are illustrative and are not to be construed as restricting the scope of the invention in any way.

Materials and Methods

Unless otherwise specified, whole rabbit eyes (Pel-Freez Biologicals, Rogers, Ark.), pig eyes (Sioux-Preme Packing, Sioux Center, Iowa) and human eyes (Georgia Eye Bank, Atlanta, Ga.), all with the optic nerve attached, were shipped on ice and stored wet at 4° C. for up to 3 days. Prior to use, eyes were allowed to come to room temperature and any fat and conjunctiva were removed to expose the sclera.

Figure 7A:
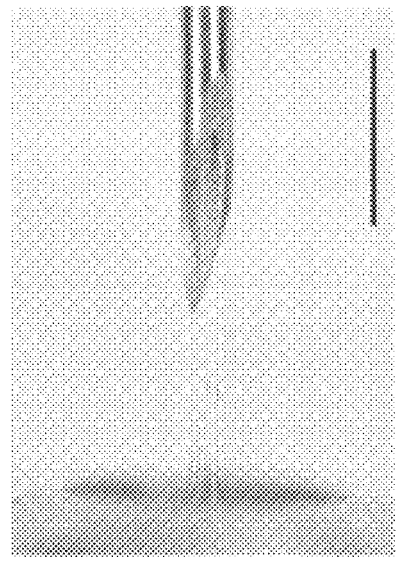
FIG. 7A shows a comparison of a hollow microneedle according to one embodiment as compared to the tip of a conventional 30 gauge hypodermic needle.

Unless otherwise specified, hollow microneedles were fabricated from borosilicate micropipette tubes (Sutter Instrument, Novato, Calif.), as described previously (J. Jiang, et al., *Pharm. Res.* 26:395-403 (2009)). FIG. 7A shows a comparison of the hollow microneedle compared to the tip of a 30 gauge hypodermic needle (scale=500 µm). A custom, pen-like device with a threaded cap was fabricated to position the microneedle and allow precise adjustment of its length. This device was attached to a micropipette holder (MMP-KIT, World Precision Instruments, Sarasota, Fla.) with tubing that was connected to a carbon dioxide gas cylinder for application of infusion pressure. The holder was attached to a micromanipulator (KITE, World Precision Instruments) which was used to control insertion of the microneedle into the sclera.

Carboxylate-modified FluoSpheres® (Invitrogen, Carlsbad, Calif.) were injected as 2 wt % solids suspension of 20 nm, 100 nm, 500 nm, and 1000 nm diameter particles. Tween 80 (Sigma-Aldrich, St. Louis, Mo.) at a final concentration of 0.5 wt %, was added to the suspension and sonicated prior to use. Sulforhodamine B (Sigma-Aldrich) was dissolved in Hanks' balanced salt solution (Mediatech, Manassas, Va.) to make a sulforhodmine solution of $10^{-4}$ M. Barium sulfate particles (Fisher Scientific, Waltham, Mass.) measuring 1 µm in diameter were suspended in balanced salt solution (BSS Plus, Alcon, Fort Worth, Tex.) to form a 1.5 wt % suspension.

Figure 7B:
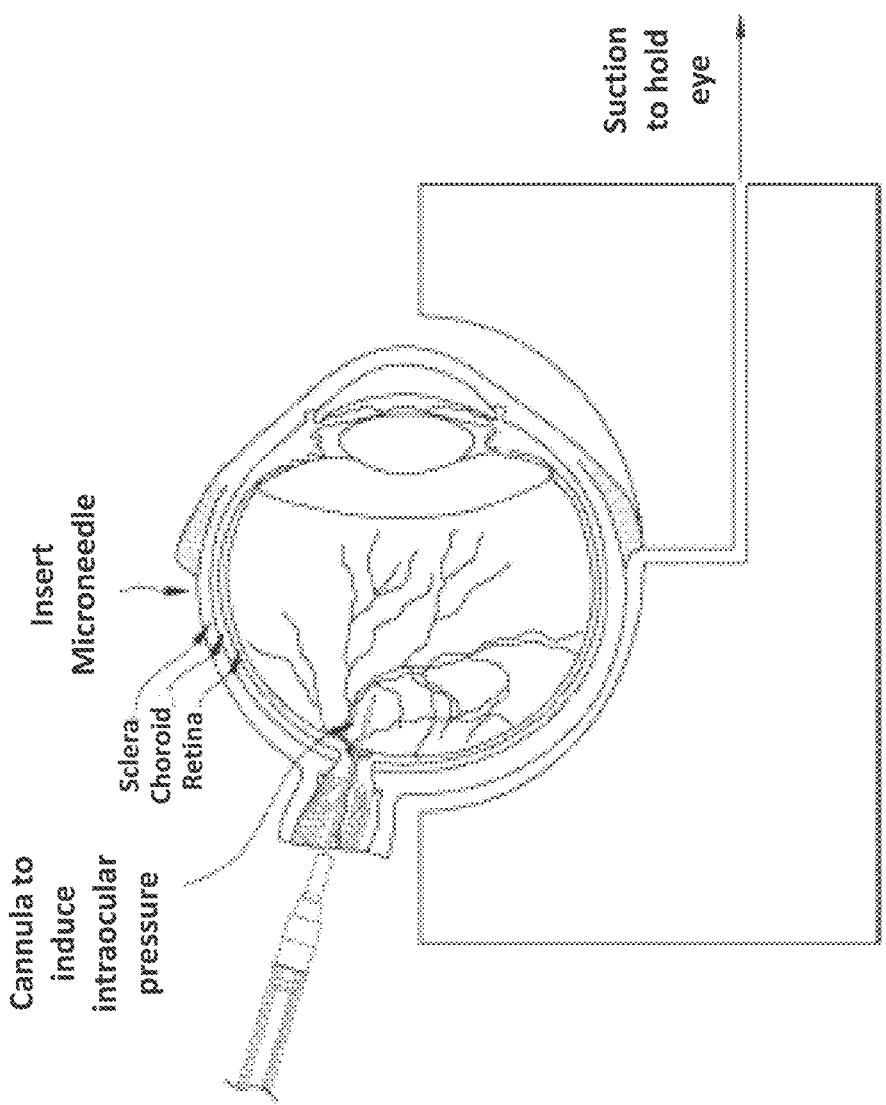
FIG. 7B shows a schematic illustration of a custom acrylic mold shaped to fit a whole eye.

A custom acrylic mold, shaped to fit a whole eye, was built to hold the eye steady and used for all experiments (FIG. 7B). A catheter was inserted through the optic nerve into the vitreous and connected to a bottle of BSS Plus raised to a height to generate internal eye pressure (18 or 36 mm Hg). Suction was applied to a channel within the mold to hold the external surface of the eye steady during microneedle insertion and manipulation. Each microneedle was pre-filled with a desired volume of the material to be injected. The microneedle was placed in the device holder at a set microneedle length, attached to the micromanipulator and connected to the constant pressure source. Microneedles were then inserted perpendicular to the sclera tissue 5-7 mm posterior from the limbus. A set pressure was applied to induce infusion. Thirty seconds were allowed to see if infusion of the solution began. If infusion occurred, the pressure was stopped immediately upon injection of the specified volume. If visual observation of the injected material showed localization in the suprachoroidal space, the injection was considered a success. If infusion had not begun within that timeframe, then the applied pressure was stopped and the needle was retracted. This was considered an unsuccessful delivery.

Eyes to be imaged using microscopy were detached from the set-up within minutes after delivery was completed. The eyes were placed in acetone or isopentane kept on dry ice or liquid nitrogen, causing the eye to freeze completely within minutes after placement. The frozen eye was removed from the liquid and portions of the eye were hand cut using a razor blade for imaging of injected material. Imaging was performed using a stereo microscope using brightfield and fluorescence optics (model SZX12, Olympus America, Center Valley, Pa.). The portions containing the sclera, choroid and retina were placed in Optimal Cutting Temperature media (Sakura Finetek, Torrance, Calif.) and frozen under dry ice or liquid nitrogen. These samples were cryosectioned 10-30 µm thick (Microm Cryo-Star HM 560MV, Walldorf, Germany) and imaged by brightfield and fluorescence microscopy (Nikon E600, Melville, N.Y.) to determine the location of injected material in the eye. Images were collaged as necessary using Adobe Photoshop software (Adobe Systems, San Jose, Calif.).

Pig eyes used for microcomputed tomography imaging were not frozen after injection. Instead, pig eyes were injected with a barium sulfate suspension and stabilized in a 30 mm diameter sample tube and scanned in air using a Scanco µCT40 desktop conebeam system (Scanco Medical AG, Brüttisellen, Switzerland) at 30 µm isotropic voxel size, E=55 kVp, I=145 µA, and integration time=200 ms. Through a convolution backprojection algorithm based on techniques from Feldkamp et. al. (*J. Opt. Soc. Am. A-Opt. Image Sci. Vis.* 1:612-619 (1984)), raw data were automatically reconstructed to generate 2D grayscale tomograms. Global segmentation values (Gauss sigma, Gauss support, and threshold) were chosen for the contrast-enhanced region as well as general eye tissue. Grayscale tomograms were stacked, and 3D binarized images were produced by applying the optimal segmentation values (one image for the entire eye and another for the region injected with contrast agent). These images were overlayed using Scanco image processing language to demonstrate the relative 3D position of the contrast-enhanced region within the entire eye.

Figure 8B:
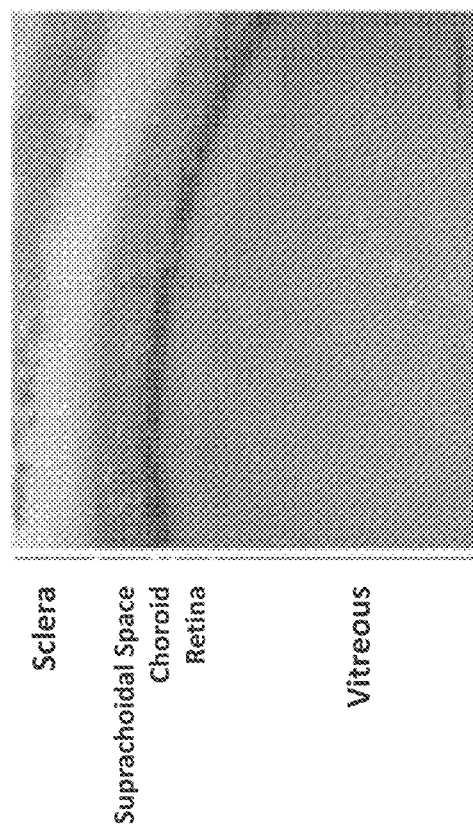
FIGS. 8A and 8B are brightfield microscopic images of saggital cross sections of a pig eye before and after infusion of sulforhadamine, respectively.
Figure 8A:
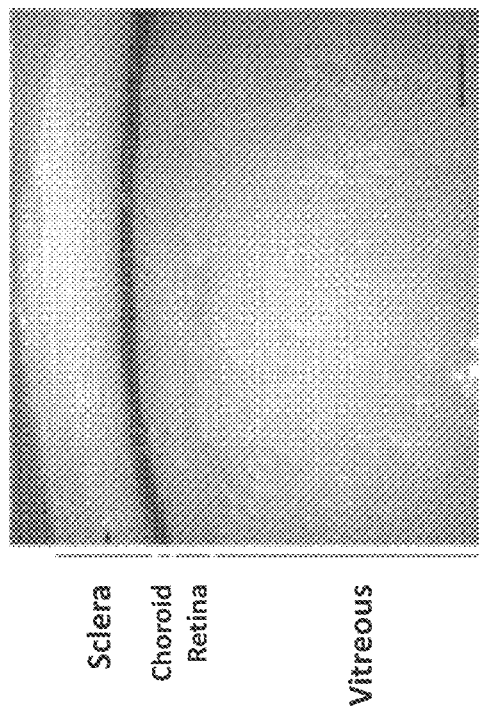

Example 1. Delivery of a Model Compound to the Suprachoroidal Space Using a Hollow Microneedle Red-fluorescent sulforhodamine B was used as a model compound and injected into pig eyes ex vivo using a single hollow microneedle inserted just to the base of the sclera in order to target the suprachoroidal space. A brightfield microscopic image of the saggital cross section of an untreated pig eye, shown in FIGS. 8A and 8B (Scale bar: 500 µm), was taken both before and after injection of 35 µL of sulforhodamine B. The normal ocular tissue (FIG. 8A) can be distinguished to identify the sclera, choroid, retina, and vitreous humor. After infusion of the model compound (FIG. 8B), the sulforhodamine solution can be seen just below the sclera and above the choroid in the suprachoroidal space, confirming that the solution was injected and spread within the suprachoroidal space from the initial injection site. Volumes up to 35 µL were able to be injected without leakage, but larger volumes leaked out from openings on the surface of the eye where vortex veins would be attached in vivo. However, subsequent experiments in pigs and rabbits in vivo have demonstrated suprachoroidal delivery of up to 100 µL without leakage through these openings (data not shown).

Example 2. Delivery of Particles to the Suprachoroidal Space Using Hollow Microneedles Particles with diameters of 500 nm or 1000 nm were injected into the suprachoroidal space of rabbit, pig and human eyes ex vivo and imaged to evaluate the distribution and localization of the particles just below the sclera. The sclera (1), choroid (2), and retina (3) were identified in a fluoroscopic image of a cryosection of a pig eye with no infusion into the suprachoroidal space (FIG. 9A, Scale bar: 500 µm). Fluoroscopic images of cryosections of a rabbit eye after injection of 500 nm particles were taken in the axial plane and the images were collaged to form a panoramic view (FIG. 9B, Scale bar: 500 µm). The spread of the fluorescent particles (which appear as the bright white regions in the images) was observed along the equator of the eye in a thin sheath just below the sclera. A volume of 15 µL was injected and, in this particular cross-section taken in the plane of the insertion site, the injection had spread approximately 20 mm, which corresponds to about 36% of the total circumference of the eye.

Figure 9C:
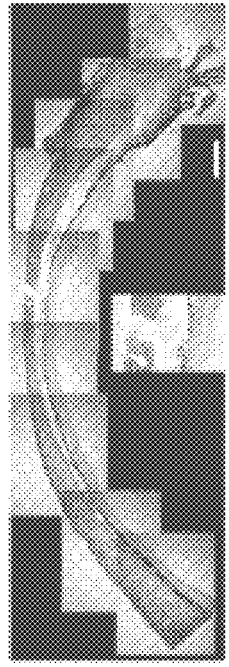
FIGS. 9A, 9B, 9C, and 9D are fluoroscopic images of a cryosection of a pig eye with no infusion into the suprachoroidal space (9A), a cryosection of a rabbit eye after infusion of 500 nm fluorescent particles in the axial plan and collaged to form a panoramic view (9B), a cryosection of a pig eye after infusion of 500 nm fluorescent particles in the saggital direction and collaged to show the spaces both anterior and posterior to the microneedle insertion site (9C), and a cryosection of a human eye after infusion of 500 nm fluorescent particles in the saggital direction and collaged to show spaces both anterior and posterior to the microneedle insertion site (9D). The insets of FIGS. 9B, 9C, and 9D show magnified views of the microneedle insertion site.
Figure 9D:
Figure 9A:
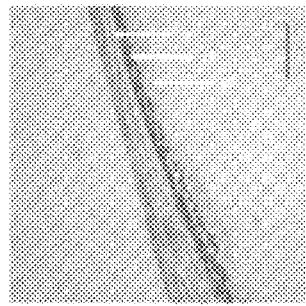
Figure 9B:
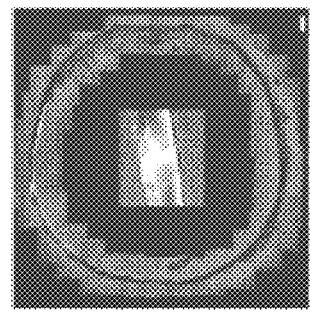

Fluoroscopic images of cryosections of pig and human eyes were taken in the sagittal directions so that the images show the anterior of the eye to the right and the posterior of the eye to the left (FIGS. 9C and 9D, respectively). These images show the ability of microinjected particles (which appear bright white) to spread in the suprachoroidal space both in the anterior and posterior direction of the eye from the injection site. In these experiments, a single microneedle delivered 30 µL of a 2 wt % particle suspension into the suprachoroidal space of both species. Leakage was observed at the vortex vein openings away from the injection site similar to what was observed with sulforhodamine injections.

The insets in these images show magnified views of the microneedle insertion site. In each case, the insertion site within the sclera was filled with particles. In the case of the pig (FIG. 9C) and human (FIG. 9D), the retina was still attached and visible, and it was clear that the microneedle had not penetrated to the retina. In the case of the rabbit (FIG. 9B), the retina separated during the cryosectioning procedure and was not visible. These results confirmed that a microneedle was able to target the suprachoroidal space of rabbit, pig, and human eyes to deliver particles up to 1000 nm in diameter. The results further confirmed that these particles spread from the injection site circumferentially in all directions within the suprachoroidal space.

Figure 10A:
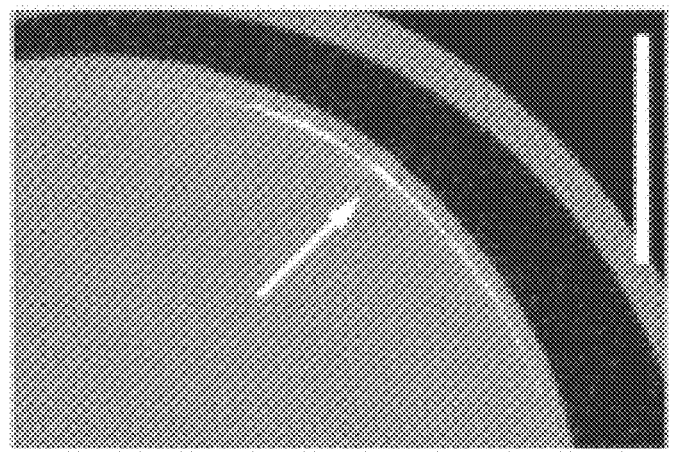
FIGS. 10A and 10B are microcomputed tomography images showing the circumferential spread of 1 µm contrast particles infused into the suprachoroidal space of a pig eye in a cross-sectional image (10A) and a three-dimensional reconstruction of the cross-sectional images (10B).
Figure 10B:

Microcomputed tomography (µCT) was utilized to image the circumferential spread and localization of injected material in the suprachoroidal space in three dimensions using a noninvasive method. After injecting 35 µL of 1 µm diameter barium sulfate contrast agent particles into the suprachoroidal space of a pig eye, cross sectional images showed the particles distributed as a thin white strip that circled just below the outer edge of the eye, i.e., just below the sclera (FIG. 10A). This profile is characteristic of suprachoroidal delivery and similar to the results from fluorescence imaging. The three-dimensional reconstruction of these cross-sectional images showed the spread of the particles in the posterior segment of the eye (FIG. 10B, Scale Bar: 5 mm). The particles spread was approximately 5 mm in radius, although asymmetrically distributed around the injection site, and covered an approximate area of 70 mm$^2$ (which represents 7% of the surface area of the back of the eye). This further confirmed the ability of microneedles to spread particles over a significant portion of the posterior segment of the eye by targeting the suprachoroidal space.

Figure 11A:
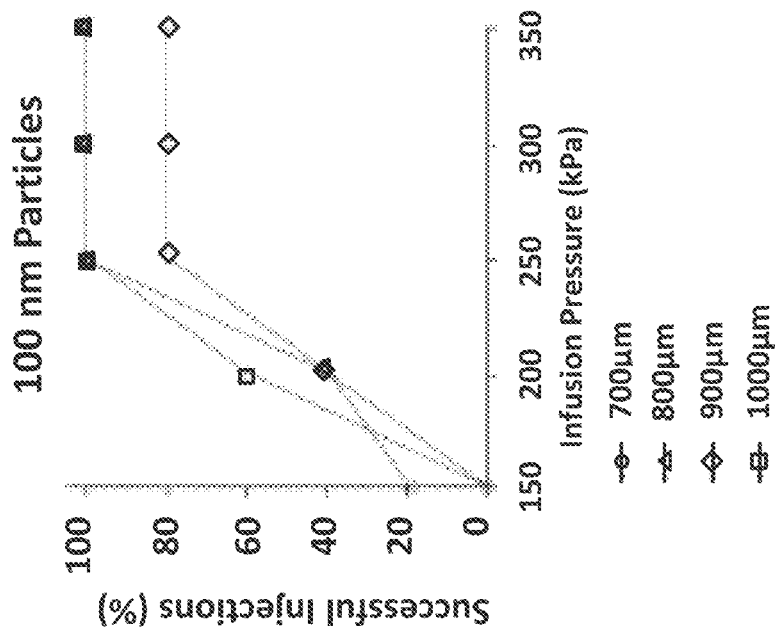
FIGS. 11A, 11B, 11C, and 11D are graphs showing the effect of infusion pressure and microneedle length on the success rate of suprachoroidal delivery of 20 nm particles (1A), 100 nm particles (11B), 500 nm particles (11C), and 1000 nm particles (11D) into pig eyes.
Figure 11B:
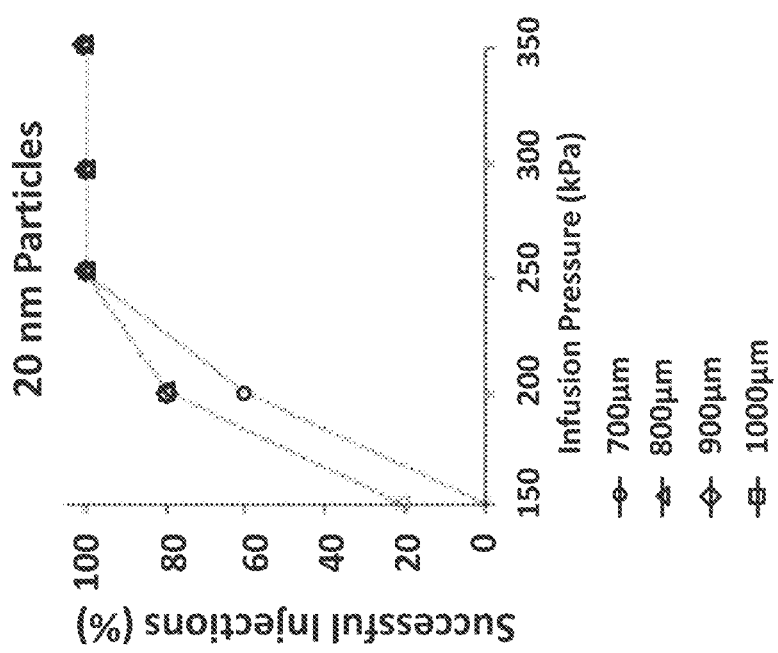
Figure 11D:
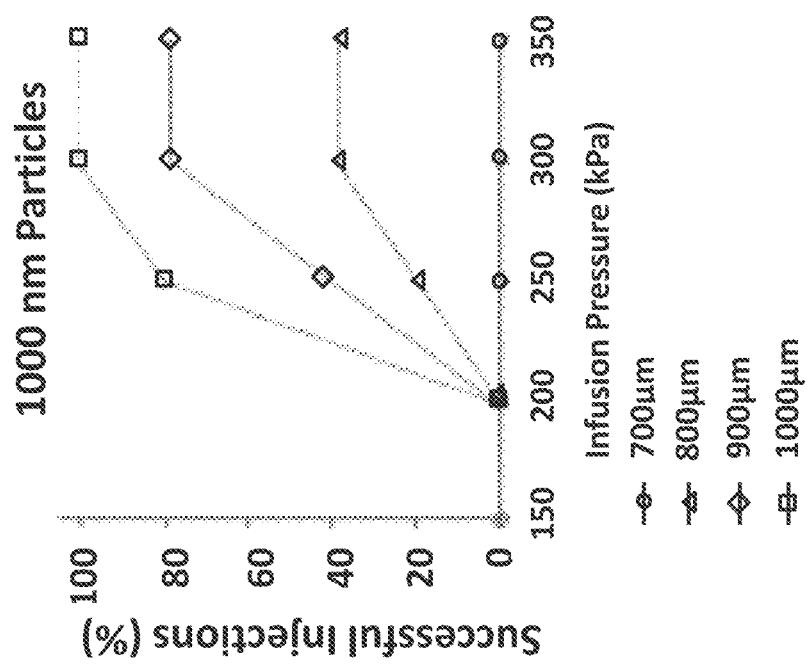
Figure 11C:
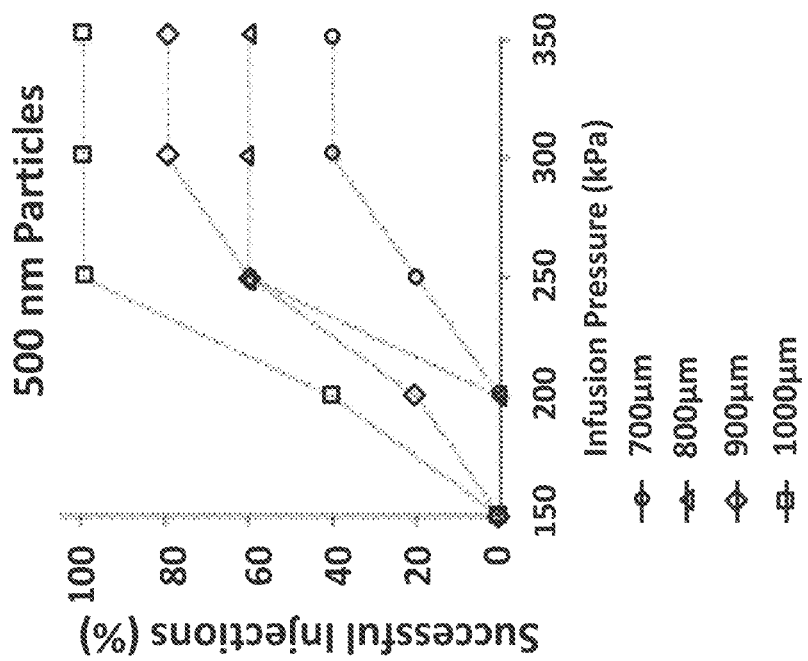

Example 3. Effect of Operating Parameters on Particle Delivery to the Suprachoroidal Space Particles of 20, 100, 500, and 1000 nm diameter were injected into pig eyes ex vivo using a range of different microneedle lengths and infusion pressures to determine the success rate of suprachoroidal delivery. An attempted injection was considered to be either fully successful (complete injection of the 25 μL particle suspension into the suprachoroidal space) or fully unsuccessful (an inability to inject at all). No partial injections were observed. The effect of infusion pressure and microneedle length on the success rate of suprachoroidal delivery of particles are shown for 20 nm (FIG. 11A), 100 nm (FIG. 11B), 500 nm (FIG. 11C), and 1000 nm (FIG. 11D) particles into pig eyes.

The success rate increased with greater infusion pressure and with greater microneedle length (ANOVA, $p<0.05$). For the 20 nm particles (FIG. 11A), 100% successful injections were achieved using a pressure of 250 kPa at all microneedle lengths. For 100 nm particles (FIG. 11B), the effects of pressure similarly plateaued at 250 kPa and 100% success was achieved at all but the shortest microneedle length (700 μm). For the larger particles (500 and 1000 nm) (FIGS. 11C and 11D, respectively), the effects of pressure generally plateued at 300 kPa and success rate significantly decreased for shorter microneedles. Not wishing to be bound by any theory, it is believed that short microneedles lengths inject within the sclera, such that particles must be forced through a portion of the sclera to reach the suprachoroidal space. Smaller particles (20 and 100 nm) can more easily force through a portion of the sclera to reach the suprachoroidal space because the spacing of collagen fiber bundles in the sclera is on the order of 300 nm. Larger particles (500 and 1000 nm), however, have more difficulty crossing this anatomical barrier, such that infusion pressure becomes a more important parameter and injection success rate decreases significantly.

A statistical comparison of the injection rates of particles of different sizes at different microneedle lengths was made using ANOVA and is summarized in the following table. Significance was considered to be a $p<0.05$ and indicated by an asterisk (*).

| Microneedle Length | 20 vs. 100 nm | 100 vs. 500 nm | 500 vs. 1000 nm | 20 vs. 1000 nm |
|---|---|---|---|---|
| 700 μm | 0.02* | 0.02* | 0.09 | 0.02* |
| 800 μm | 0.37 | 0.00* | 0.10 | 0.01* |
| 900 μm | 0.18 | 0.03* | 0.18 | 0.03* |
| 1000 μm | 0.18 | 0.37 | 0.21 | 0.18 |

The statistical analysis showed that at a microneedle length of 700 μm, where the most scleral tissue must be traversed to reach the suprachoroidal space, success rate depended strongly on particle size. Using 800 and 900 μm microneedles, particles smaller than the collagen fiber spacing (20 and 100 nm) behaved similarly and particles larger than the collagen fiber spacing (500 and 1000 nm) also behaved similarly, but there was a significant difference between 100 nm and 500 nm particles. The longest microneedles (1000 μm), which probably reached the base of the sclera, showed no significant dependence on particle size, suggesting that overcoming the collagen barrier in the sclera was no longer needed.

Figure 12B:
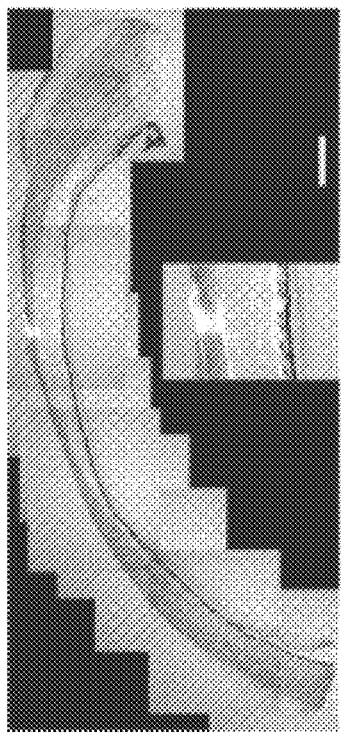
FIGS. 12A and 12B are fluoroscopic images of a cryosection of a pig eye after infusion of 20 nm particles (12A) and 1000 nm particles (12B) in the saggital direction and collaged to show spaces both anterior and posterior to the microneedle insertion site. The insets of FIGS. 12A and 12B show magnified views of the microneedle insertion site.
Figure 12A:
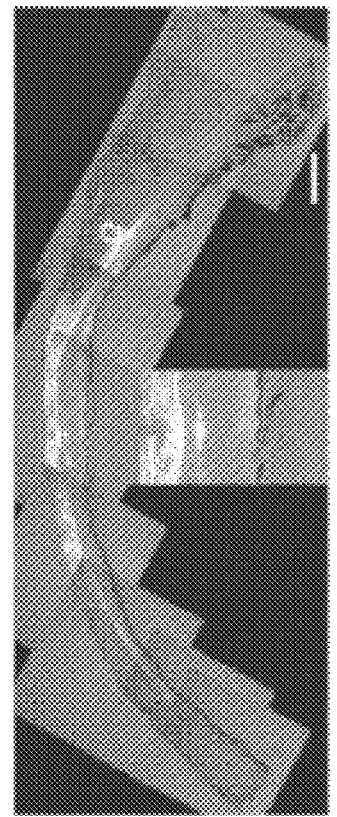

Not wishing to be bound by any particular theory, the foregoing further suggested that particles of 20 and 100 nm can spread within the sclera as well as the suprachoroidal space, whereas particles of 500 and 1000 nm should localize exclusively in the suprachoroidal space. The spread of 20 nm particles (FIG. 12A) was compared to the spread of 1000 nm particles (FIG. 12B) under identical conditions. As expected, the smaller particles exhibited significant spread in the sclera as well as the suprachoroidal space. In contrast, the larger particles were relegated primarily to the suprachoroidal space and were largely excluded from the sclera. This localization of large particles was consistent with the results shown in FIG. 11.

Thus, 20 and 100 nm particles were reliably injected using a minimum microneedle length of 800 μm and a minimum pressure of 250 kPa. To deliver 500 and 1000 nm particles, a minimum microneedle length of 1000 μm and a minimum pressure of 250-300 kPa was required.

Figure 13B:
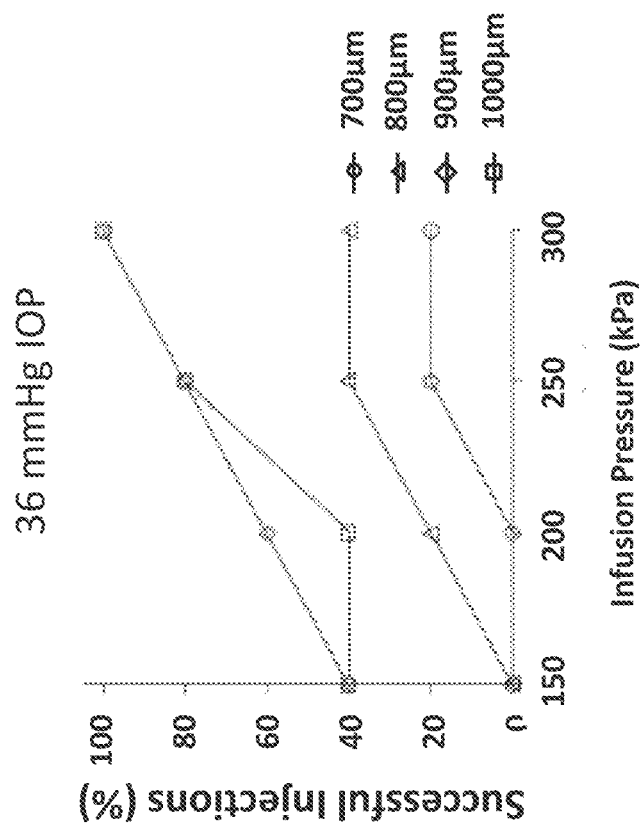
FIGS. 13A and 13B are graphs showing the effect of the intraocular pressure and microneedle length on the success rate of suprachoroidal delivery of 1000 nm particles for a simulated intraocular pressure of 18 mmHg (13A) and 36 mmHg (13B).
Figure 13A:
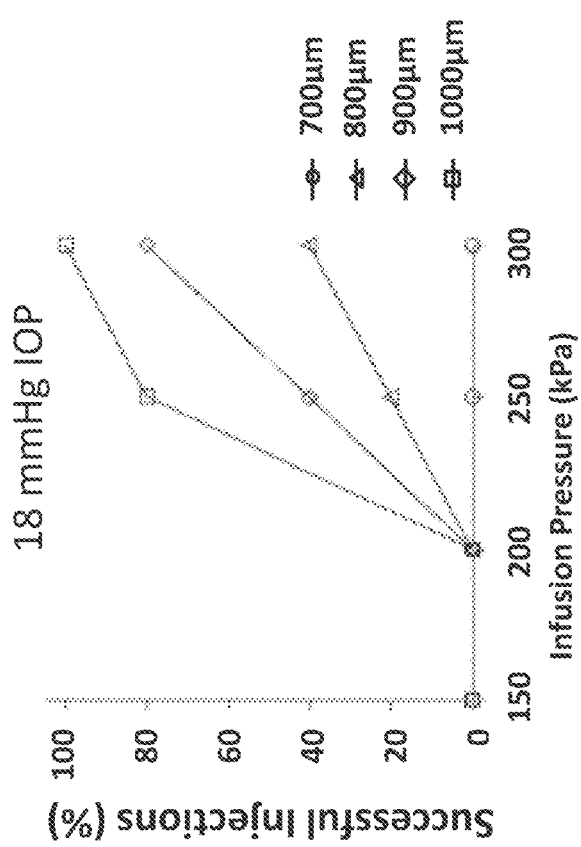

Example 4. Effect of Intraocular Pressure on Delivery of Particles to the Suprachoroidal Space Intraocular Pressure (TOP) is the internal pressure within the eye that keeps the eye inflated. It provides a back pressure that can counteract the infusion pressure. To evaluate the effect of intraocular pressure on particle delivery to the suprachoroidal space, 1000 nm particles were injected at two different levels of IOP, 18 and 36 mmHg. The effect of infusion pressure and microneedle length on the success rate of suprachoroidal delivery of 1000 nm particles at simulated TOP levels of 18 mmHg and 36 mmHg is shown in FIG. 13A and FIG. 13B, respectively. The delivery success rate generally increased with an increase in TOP. Notably, at normal TOP, no particles were delivered at the lowest infusion pressure (150 kPa) or using the shortest microneedles (700 μm) and only the longest microneedles (1000 μm) achieved 100% success rate at the highest infusion pressure (300 kPa) (FIG. 13A). In contrast, at elevated TOP, particles were sometimes delivered at the lowest infusion pressure and using the shortest microneedles, and a 100% success rate was achieved using both 900 and 1000 μm microneedles at the highest infusion pressure (FIG. 13B).

Not wishing to be bound by any theory, it is believed that the main effect of elevated TOP is to make the sclera surface more firm, reducing tissue surface deflection during microneedle insertion and thereby increasing the depth of penetration into sclera for a microneedle of a given length. Although microneedle insertion depth was not measured directly, these results suggest that microneedle insertion may be more effective at elevated TOP because the microneedles insert deeper into the sclera and thereby increase infusion success rate.

Figure 14:
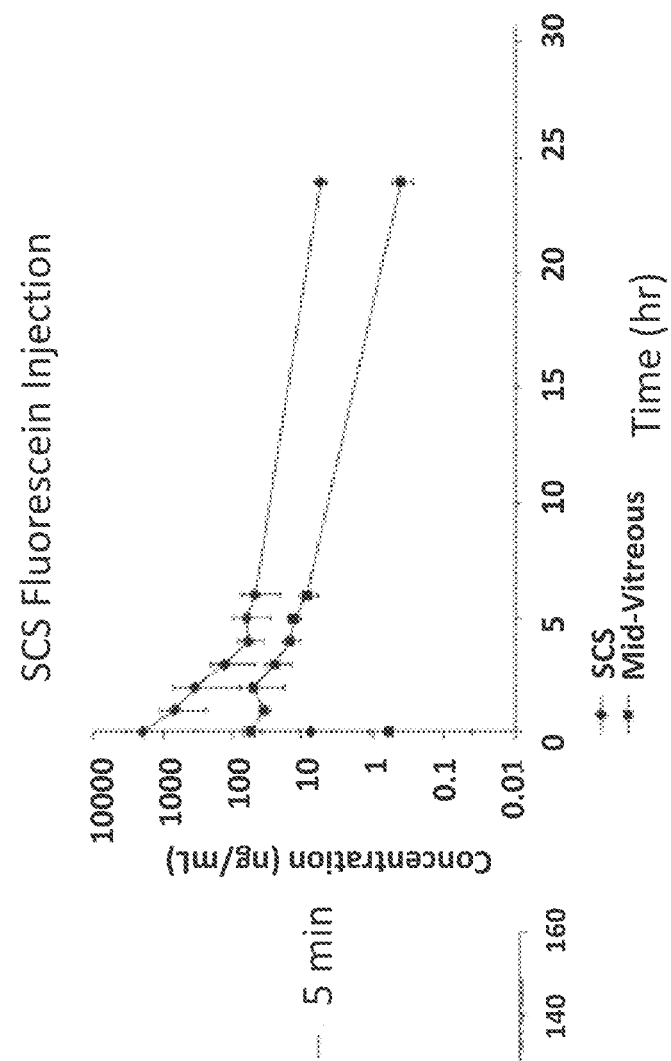
FIG. 14 is a one-dimensional line of sight scan of rabbit eyes taken after injection of sodium fluorescein to the suprachoroidal space, with the x-axis representing the position in the eye from back (0) to front (160) and the y-axis representing the fluorescent intensity at that position.

Example 5. Delivery of Model Compound to Suprachoroidal Space in Live Animal Models The delivery of a fluorescent molecule (sodium fluorescein) to the suprachoroidal space was evaluated using rabbits according to approved live animal experimental protocols. A one dimensional scan of the eye (through line of sight) was taken within the first five minutes after injection to determine the dispersion of the fluorescent molecule in the eye (FIG. 14). The y-axis indicates the fluorescent intensity (i.e., the concentration) and the x-axis represents the position in the eye from front (160) to back (0). Thus, the results illustrate that within the first 5 minutes after injection, the fluorescein had already flowed through the suprachoroidal space to the back of the eye, with some remaining at the initial insertion site.

Figure 15:
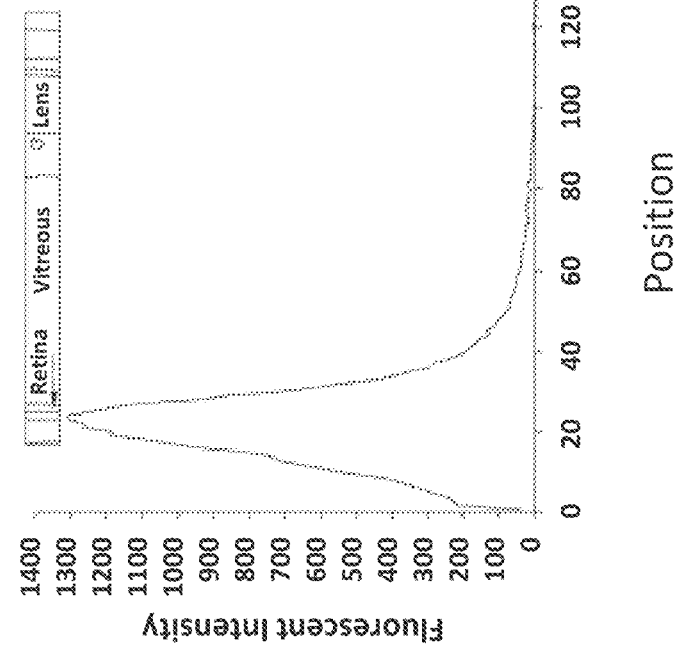
FIG. 15 is a graph showing the rate of clearance of sodium fluorescein from the suprachoroidal space over time.

Similar scans were taken to evaluate the rate of clearance of fluorescein from the suprachoroidal space over time (FIG. 15). The fluorescent intensity was measured in two regions of the eye (the suprachoroidal space and mid-vitreous region) over time. The results illustrate that the bulk of the material injected remains in the suprachoroidal space without passing into the mid-vitreous region and that the material substantially cleared the suprachoroidal space within 24 hours.

Example 6. Delivery of Particles to Suprachoroidal Space in Live Animal Models

Live animal experiments also were conducted to evaluate the delivery of particles to the suprachoroidal space. Fluorescent particles having a diameter of 20 nm and 500 nm were infused into rabbit eyes and the fluorescent intensity was evaluated to determine the length of time the particles remained in two regions of the eye (the suprachoroidal space and mid-vitreous region).

Figure 17:
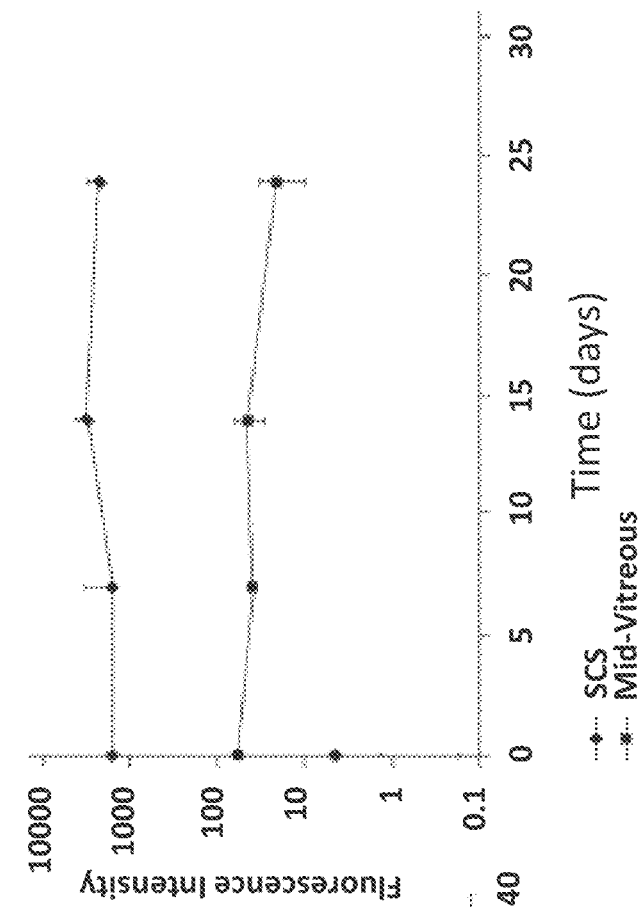
FIG. 17 is a graph showing the rate of clearance of 500 nm particles from the suprachoroidal space over time.
Figure 16:
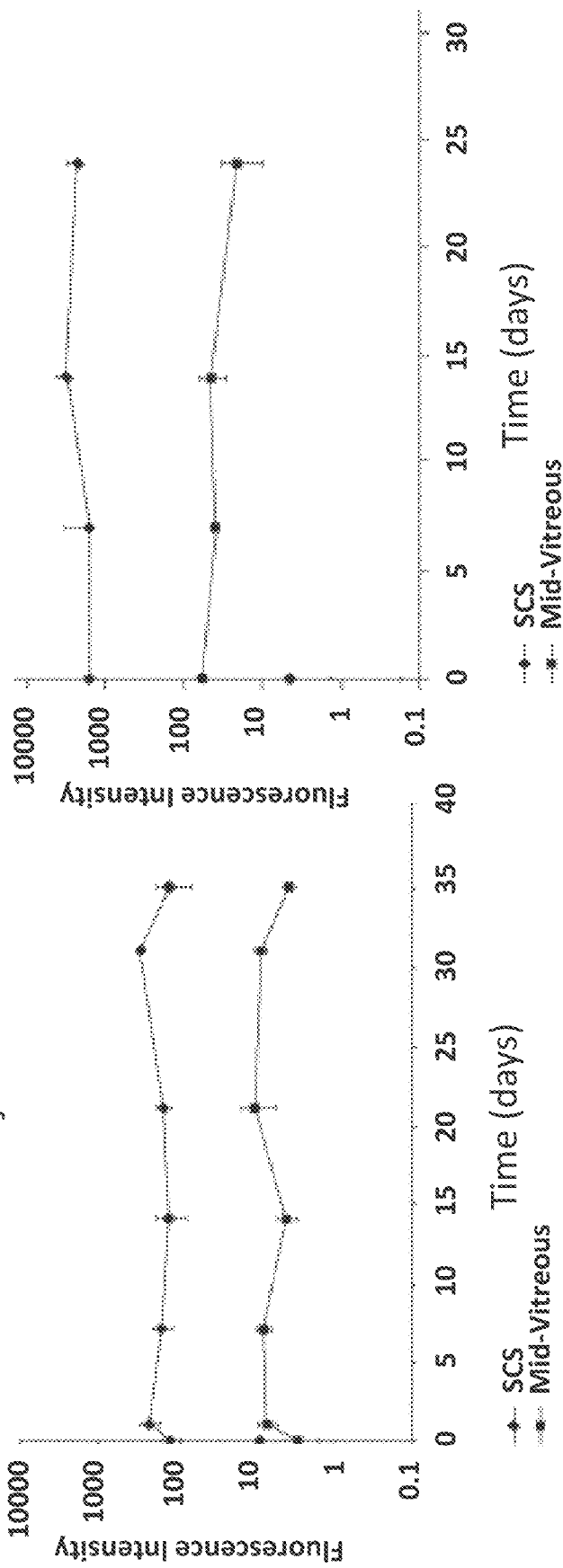
FIG. 16 is a graph showing the rate of clearance of 20 nm particles from the suprachoroidal space over time.

The smaller particles (FIG. 16) were successfully delivered to the suprachoroidal space and remained in the suprachoroidal space for at least 35 days. The larger particles (FIG. 17) also were successfully delivered to the suprachoroidal space and remained in the suprachoroidal space for at least 24 days. Notably, both the smaller and larger particles were well localized as indicated by the low level of fluorescence in the mid-vitreous region.

Example 7. Triamcinolone Formulations for Delivery to the Suprachoroidal Space

Triamcinolone is delivered to the suprachoroidal space using the methods and devices provided herein. The triamcinolone formulation, in one embodiment, is selected from one of the following three formulations.

into the suprachoroidal space using a hollow microneedle or into the vitreous using a standard 30 gauge needle was compared.

On Day 0, pigmented rabbits were injected with either intravitreal or bilateral suprachoroidal injections of 2 mg/100 µl TA Triesence® (TA; Alcon Labs). Intravitreal injections were performed using a 30 g needle (Becton-Dickinson) and suprachoroidal injections were performed using a 33 g 750 µm microneedle. The residual amount of TA present in the syringe/needle assembly after injection was determined by RP-HPLC. Clinical observations, slit lamp biomicroscopy with McDonald-Shadduck scoring, intraocular pressure assessment (TOP), electroretinography (ERG), and systemic exposure were assessed up to 120 days post-dose. Animals were sacrificed at 30 minutes, 7 days, 30 days, 60 days, and 120 days for macroscopic observations, ocular toxicokinetics, and ocular histopathology.

Figure 19B:
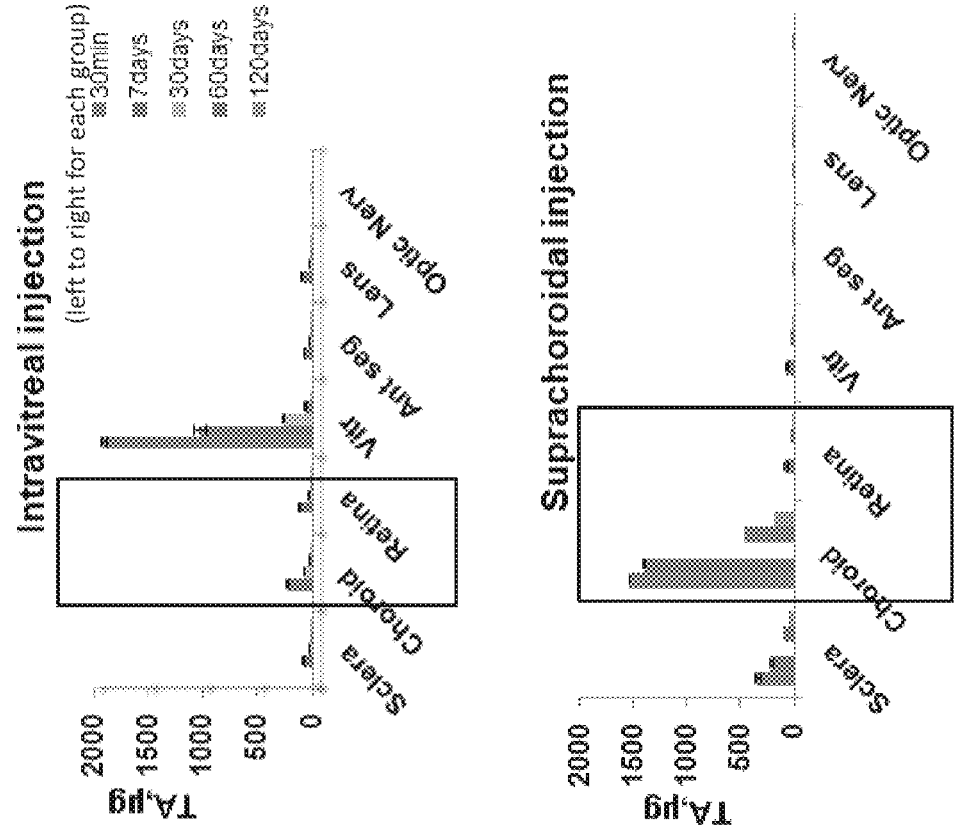
FIG. 19B are graphs showing the increased retention of triamcinolone (TA) in the choroid and retina when administered to the SCS (bottom) compared with TA administered intravitreally (top).
Figure 19A:
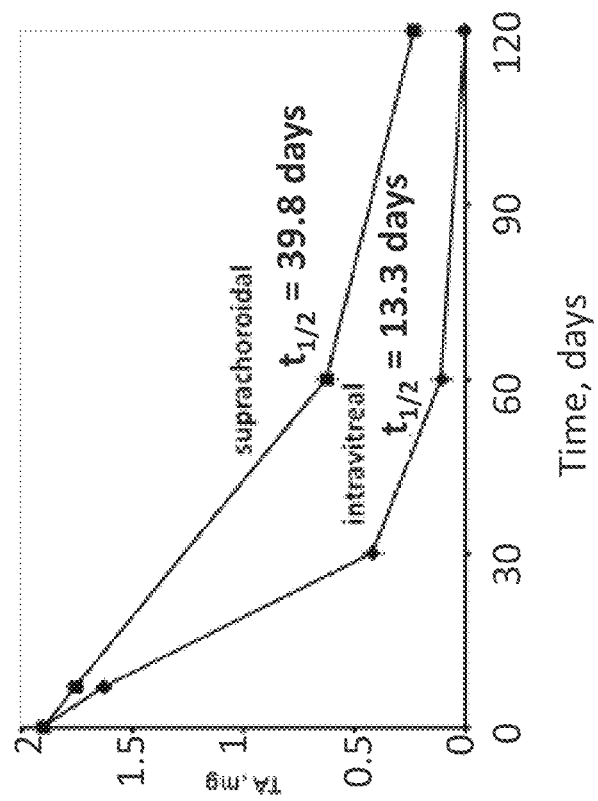
FIG. 19A is a graph showing the amount of triamcinolone (TA) retained in the posterior segment of the eye as a function of time after administration. (circles—SCS injection, diamonds intravitreal injection).

As demonstrated in FIG. 19A, the TA was retained longer in the eye after administration to the SCS than after intravitreal administration. On average, the $t_{1/2}$ of intravitreally administered drug was 13.3 days, while the drug delivered to the SCS had a $t_{1/2}$ of 39.8 days.

Figure 19C:
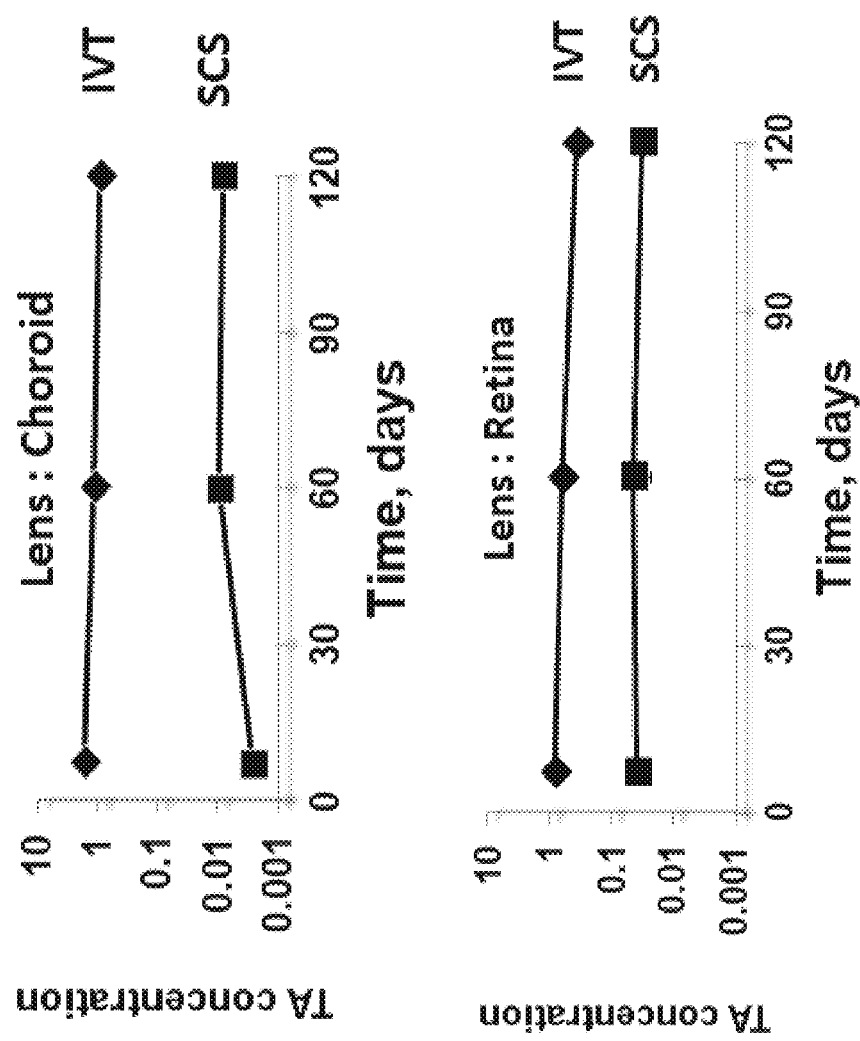
FIG. 19C, top, is a graph showing the ratio of the amount of triamcinolone (TA) in the lens of the eye to the amount of TA in back of the eye (choroid) as a function of time after administration.

Furthermore, the drug that was delivered to the SCS was targeted to the back of the eye, i.e., the posterior segment of the eye. FIG. 19B shows that a higher concentration of TA found in the choroid and retina when the drug was administered to the SCS. SCS administration not only directed the drug to the posterior portion of the eye, but also limited the amount of drug found in anterior portions, such as the lens, and in the vitreous fluid. When the drug was administered intravitreally, the opposite was observed: the highest concentrations of the drug were found in the vitreous, with lower doses being found in the choroid and retina. Higher TA concentrations in the anterior of the eye after intravitreal administration are also shown in FIG. 19C. This figures shows that the ratio of TA administered intravitreally was approximately 1:1 for both Lens:Chroroid and Lens:Retina while the ratio for SCS delivered TA was much lower.

These data show that administration of TA to the SCS instead of intravitreally results a longer half-life of the TA in

| Ingredient | Formulation A | Formulation B | Formulation C | Formulation D | Formulation E |
| --- | --- | --- | --- | --- | --- |
| Triamcinolone acetonide | 40 mg/mL | 40 mg/mL | 40 mg/mL | 40 mg/mL | 40 mg/mL |
| Particle Size | $D_{50}$: ~2 µm $D_{99}$: <10 µm | $D_{50}$: ~2 µm $D_{99}$: <10 µm | $D_{50}$: ~2 µm $D_{99}$: <10 µm | $D_{50}$: ~2 µm $D_{99}$: <10 µm | $D_{50}$: ~2 µm $D_{99}$: <10 µm |
| Sodium Chloride | 0.64% w/v | 0.64% w/v | 0.64% w/v | 0.64% w/v | 0.64% w/v |
| Carboxymethylcellulose sodium | 0.5% w/v | 0.5% w/v | 0.5% w/v | 0.5% w/v | 0.5% w/v |
| Polysorbate 80 | 0.02% w/v | 0.015% w/v | ≥0.015% w/v | 0.015% w/v | 0.02% w/v |
| NaOH/HCl | Adjust to pH 6.0-7.5 | Adjust to pH 6.0-7.5 | Adjust to pH 6.0-7.5 | Adjust to pH 6.0-7.5 | Adjust to pH 6.0-7.5 |
| KCl | 0.075% w/v | 0.075% w/v | 0.075% w/v | 0.075% w/v | 0.075% w/v |
| CaCl2 (dihydrate) | 0.048% w/v | 0.048% w/v | 0.048% w/v | 0.048% w/v | 0.048% w/v |
| MgCl2 (hexahydrate) | 0.030% w/v | 0.030% w/v | 0.030% w/v | 0.030% w/v | 0.030% w/v |
| Sodium acetate (trihydrate) | 0.39% w/v | 0.39% w/v | 0.39% w/v | 0.39% w/v | 0.39% w/v |
| Sodium citrate (dihydrate) | 0.17% w/v | 0.17% w/v | 0.17% w/v | 0.17% w/v | 0.17% w/v |

Example 8. Comparison of the Total Amount of Triamcinolone Acetonide Delivered Via Suprachoroidal or Intravitreal Administration In this study, the total amount of triamcinolone acetonide (TA) delivered into live pigmented rabbit eyes when injected the eye, and better targeting of the TA to the back of they eye. The administration of TA to the SCS using a microneedle also shows a favorable safety profile with no marked inflammation, edema, apoptosis, or necrosis at any time point. Finally, administration of Triesence® into the suprachoroidal space using a microneedle delivered approximately the same total dose of TA as a standard intravitreal injection in this model.

Example 9. Suprachoroidal Microinjection of Triamcinolone Acetonide in the New Zealand White Rabbit In this study, the ocular tolerability and toxicokinetics of suprachoroidal administration of triamcinolone acetonide (TA) using a microneedle in a GLP study in the New Zealand White rabbit.

On Day 0, New Zealand White (NZW) rabbits were administered a single bilateral suprachoroidal injection of vehicle, 3.2 mg (80 µL) or 5.2 mg (130 µL) of TA (Triesence®, Alcon labs) using a 33 g 750 µm microneedle. Clinical observations, slit lamp biomicroscopy with McDonald-Shadduck scoring, intraocular pressure assessment (IOP), electroretinography (ERG), and systemic exposure were assessed up to 26 weeks post-dose. Animals were sacrificed on Day 1, Week 13, and Week 26 for macroscopic observations, ocular toxicokinetics, and ocular histopathology. Results of ophthalmic examinations at 13 weeks post administration are provided in Table 1, below. Findings absorbed during slit lamp biomicroscopy and fundus examination were generally mild and transient in nature, and demonstrated excellent ocular tolerability for up to 13 weeks following suprachoroidal administration. Results of electroretinography experiments are provided in Table 2. There was no administration or TA-related effect on a-wave or b-wave implicit time or amplitude as assessed by scotopic ERG.

TABLE 1

Results of ophthalmic examinations

| | Dose level (mg TA/eye) | | | | | |
|---|---|---|---|---|---|---|
| | 0 | | 3.2 | | 5.2 | |
| | Number of Animals | | | | | |
| | M: 15 | F: 15 | M: 25 | F: 15 | M: 25 | F: 15 |
| Conjunctival congestion (slight, transient) | — | 1 | — | 2 | 1 | — |
| Conjunctival discharge (slight, transient) | — | — | — | 2 | — | 1 |
| Corneal Staining (slight, transient) | 2 | 1 | 1 | 1 | 4 | 2 |
| Hyperemia (severe, transient) | — | — | — | 1 | — | — |
| Lens Defect* | 1 | 1 | — | 1 | — | — |

*Anatomic defect unrelated to administration

TABLE 2

Electroretinography results

| | | | | Scotopic | | | |
|---|---|---|---|---|---|---|---|
| | | | | OdB wave A Right & left eye | | OdB wave B Right & left eye | |
| Dose level (mg TA/eye) | Time point | # of eyes | Protocol | Mean | SD | Mean | SD |
| 0 | Baseline | 60 | Time (ms) | 11.7 | 0.7 | 42.5 | 8.7 |
| | | | Amplitude (µV) | −126.4 | 27.1 | 273.7 | 68.6 |
| | Day 1 | 60 | Time (ms) | 11.7 | 0.9 | 42.4 | 8.2 |
| | | | Amplitude (µV) | −121 | 25.8 | 255.2 | 57 |
| | Week 13 | 20 | Time (ms) | 11.7 | 0.6 | 41.9 | 8.2 |
| | | | Amplitude (µV) | −101.1 | 11 | 248.1 | 60.2 |
| 3.2 | Baseline | 60 | Time (ms) | 11.6 | 0.8 | 42.1 | 8.5 |
| | | | Amplitude (µV) | −133.2 | 24.5 | 285.8 | 59.5 |
| | Day 1 | 60 | Time (ms) | 11.4 | 0.8 | 47.5 | 6.7 |
| | | | Amplitude (µV) | −132 | 22.2 | 276.5 | 58.7 |
| | Week 13 | 20 | Time (ms) | 11.7 | 0.6 | 51.1 | 1.1 |
| | | | Amplitude (µV) | −132.6 | 17.2 | 299.8 | 72.8 |
| 5.2 | Baseline | 60 | Time (ms) | 11.7 | 0.6 | 42.3 | 8.7 |
| | | | Amplitude (µV) | −137.3 | 22.1 | 286.4 | 60.5 |
| | Day 1 | 60 | Time (ms) | 11.4 | 0.7 | 43.1 | 8.4 |
| | | | Amplitude (µV) | −130.8 | 21.2 | 265.7 | 48.2 |
| | Week 13 | 20 | Time (ms) | 12.6 | 3.3 | 45.7 | 8.6 |
| | | | Amplitude (µV) | −117.1 | 44.5 | 264.6 | 90.1 |

Figure 20A:
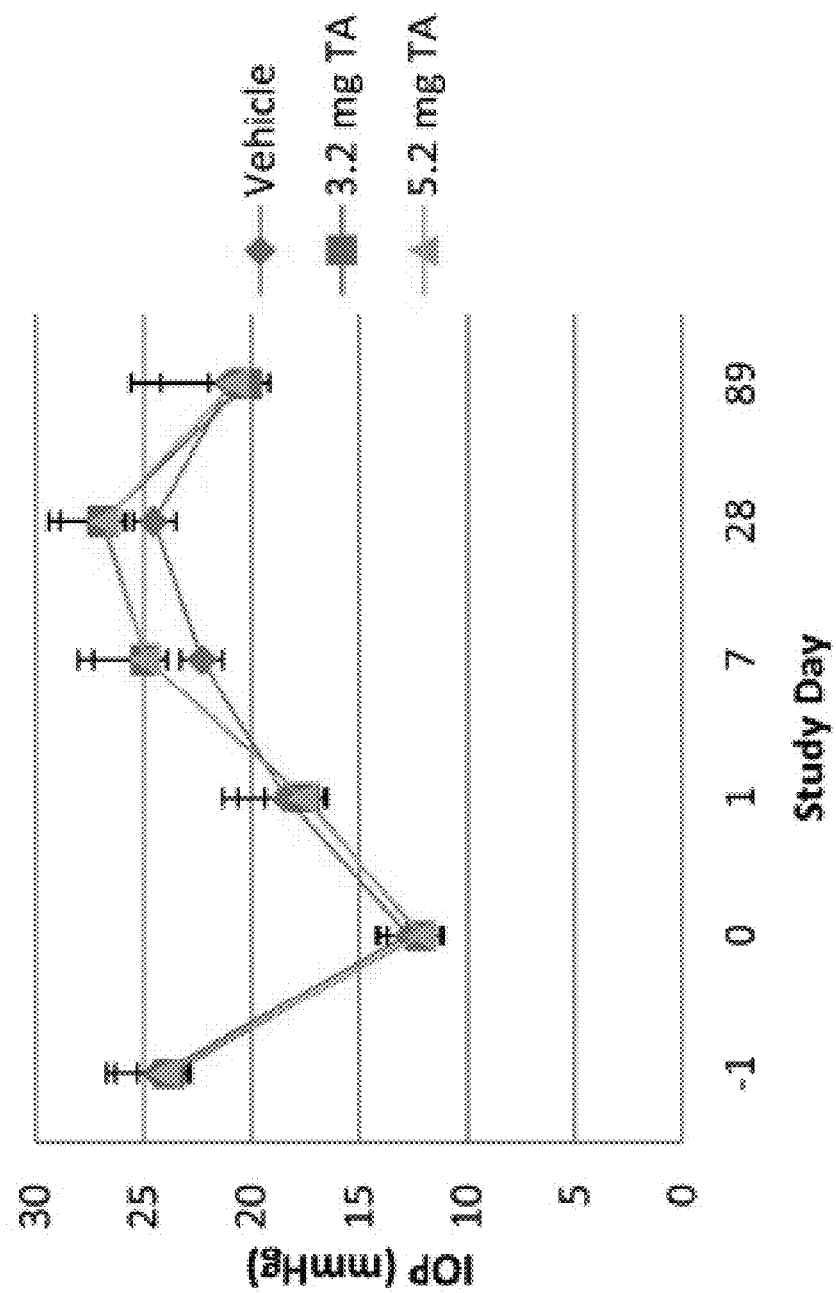
FIG. 20A is a graph of intraocular pressure (TOP, mmHg) in rabbit eyes as a function of time after TA administration. Rabbits were injected with vehicle, 3.2 mg TA or 5.2 mg TA at study day 0.

There were no adverse effects related to test article, dose or method of administration on clinical observations, body weight, or ophthalmic examinations. No effect on IOP was noted in any animal (FIG. 20A).

Inflammatory cells and test article were observed in the suprachoroidal space of TA-treated animals on Day 1 but not Week 13 as assessed by histopathology. Additionally, TA was easily visualized within the suprachoroidal space on day 1 and no adverse effects related to the method of administration or treatments, as assessed by histopathology (FIG. 20B, Table 3).

TABLE 3

Histopathology results

| Time point | | Dose level (mg TA/eye) | | | | | |
|---|---|---|---|---|---|---|---|
| | | 0 | | 3.2 | | 5.2 | |
| | | # animals | | | | | |
| | | M: 15 | F: 15 | M: 25 | F: 15 | M: 25 | F: 15 |
| Day 1 | Conjunctival subepithelial inflammatory cells | 4 | 3 | 3 | — | 2 | 3 |
| | Corneal epithelial thinning | 2 | 1 | 3 | 2 | 3 | 1 |
| | Ciliary process edema | 5 | 4 | 4 | 4 | 4 | 5 |
| | Dilated choroidal vessels | — | — | — | — | — | — |
| | Inflammatory cells in SCS | — | — | 5 | 4 | 5 | 5 |
| | TA in SCS | — | — | 5 | 5 | 4 | 5 |
| | Small area of retinal damage* | — | 1 | — | — | — | 1 |
| Week 13 | Conjunctival subepithelial inflammatory cells | — | — | — | — | — | — |
| | Corneal epithelial thinning | — | — | — | — | — | — |
| | Ciliary process edema | 3 | 3 | 3 | 1 | 1 | 3 |
| | Dilated choroidal vessels | — | — | — | 1 | 1 | — |
| | Inflammatory cells in SCS | — | — | — | — | — | — |
| | TA in SCS | — | — | — | — | — | — |
| | Small area of retinal damage* | — | — | — | 1 | — | — |

*attributed to needle insertion

Plasma and ocular matrixes (aqueous humor (AH), lens, iris/ciliary body (ICB), vitreous humor (VH), sclera/choroid (SC), and retina) were sampled on Days 1, 14, 28, and 60. Plasma (LLOQ 0.5 ng/mL) and ocular matrixes (LLOQ 2-15 ng/mL) were analyzed using LC-MS/MS, and resulting data were assessed for noncompartmental PK parameters. Systemic exposure to TA was minimal (FIG. 20C).

Figure 20D:
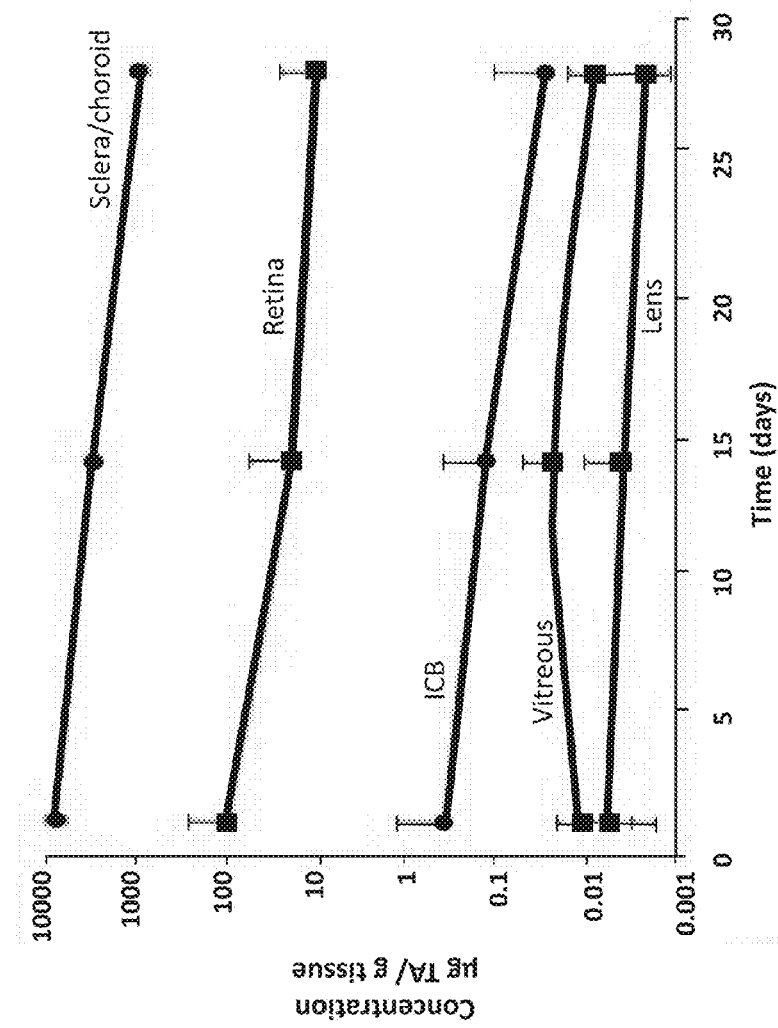
FIG. 20D is a graph showing the retention of triamcinolone (TA) (µg TA/g tissue) in various tissues after administration to the SCS. The greatest amount of the drug is retained in the tissues in the back of the eye (choroid, retina) with lesser amounts retained in anterior portions of the eye (lens, vitreous fluid).

There were no observed adverse effects related to treatment. TA in plasma peaked on Day 1 around 12 ng/mL in both the high and low TA dose groups. Following SCS TA, TA was observed (in decreasing order) in SC>retina>ICB>VH>lens>AH. TA was observed at high concentrations in the sclera/choroid and retina, to a lesser extent in the iris/ciliary body, and was present only at low concentrations in the aqueous humor, lens, and vitreous (FIG. 20D). Specifically, sclera/choroid tissue concentration of TA can be achieved at greater than 100 μg/g tissue for longer than 28 days after a single dose. The majority of the dose delivered is retained in the posterior ocular tissue with very little drug delivered to the anterior tissues. The levels of TA in the sclera/choroid were 6 orders of magnitude different from the levels found in the vitreous. This is the opposite of what one would expect to find after administration of the agent intravitreally. The concentration of TA observed in the posterior portion of the eye provide efficacy in animal models of posterior inflammation even though there is very little drug concentration in the vitreous.

Figures 20E, 20F:
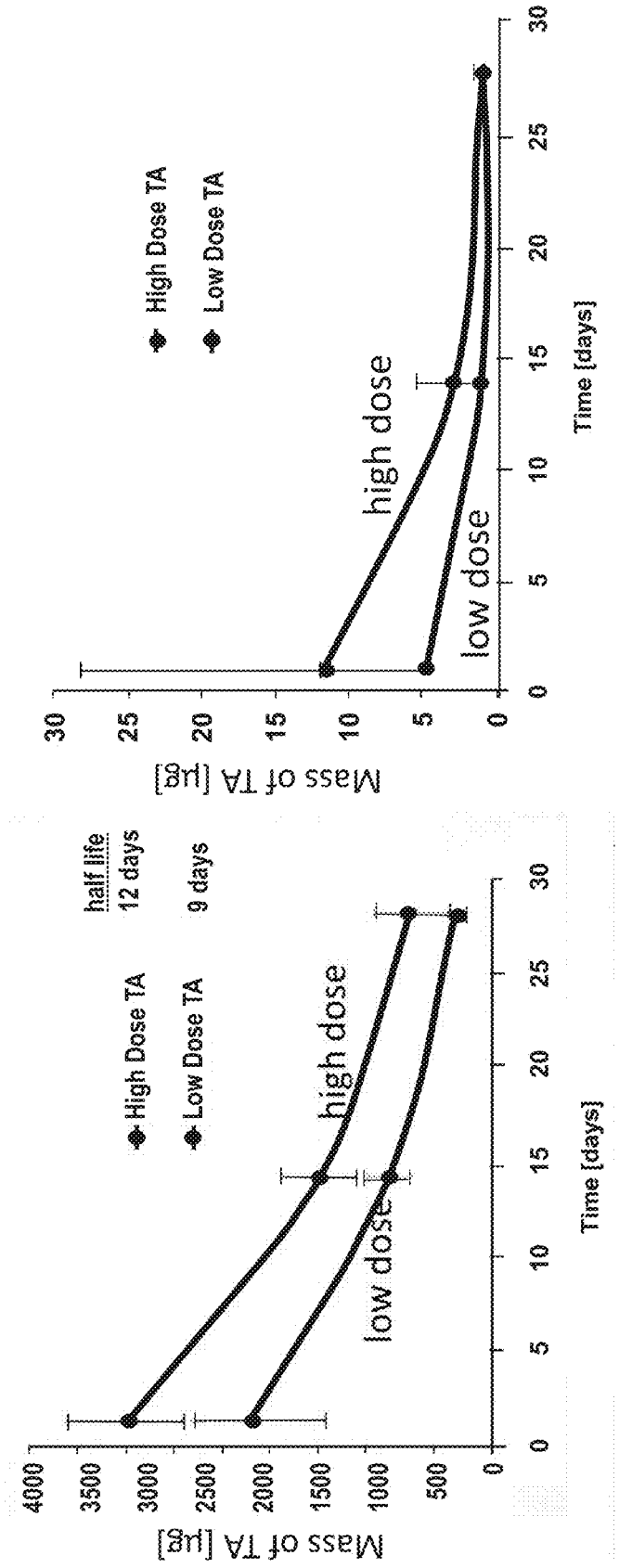
FIG. 20E is a graph showing the amount of triamcinolone (TA) (µg) in the sclera and choroid as a function of time after TA administration.
FIG. 20F is a graph showing the amount of triamcinolone (TA) (µg) in the retina as a function of time after TA administration.

Furthermore, the amount of TA retained in the sclera/choroid and the retina delivered to the SCS did not significantly differ depending on the dose. Comparison of the mass of TA (μg) found in the sclera/choroid over time showed that, by day 30 the amount of TA retained in the sclera/choroid of animals treated with the high dose of TA and those treated with the low dose of TA did not significantly differ (FIG. 20E). The amount of TA retained in the retina did not significantly differ by day 15 (FIG. 20F).

These data suggest that suprachoroidal drug delivery is well tolerated, results in distribution of TA to the sclera/choroid and retina, structures that are important targets for anti-inflammatory agents in posterior segment disease, and limits TA exposure in the anterior segment.

Example 10. Suprachoroidal Microinjection Delivers TA to Therapeutically-Relevant Posterior Ocular Structures and Limits Exposure in the Anterior Segment In this study, the ocular and systemic pharmacokinetics (PK) of triamcinolone acetonide (TA) in the New Zealand White rabbit following intravitreal (IVT) injection or administration into the suprachoroidal space (SCS) using a hollow microneedle were evaluated.

On Day 0, male rabbits (5 per group) received a single bilateral administration of 4 mg TA (100 μL Triesence® triamcinolone formulation, Alcon Labs) via SCS injection using a 33 g 750 μm microneedle or an IVT injection using a standard 30 g needle. The study design is shown below in Table 4.

TABLE 4

Study design.

| Group | # of animals | Dose administration | | | | Schedule | |
|---|---|---|---|---|---|---|---|
| | | Dose level | Route | Dose volume | Day of dosing | Euthanasia | |
| 1 | 5 | 4 mg TA | SCS | 100 μL | 0 | day 1, 14, 28, 56 or 91 | |
| 2 | 5 | 4 mg TA | IVT | 100 μL | 0 | day 1, 14, 28, 56 or 91 | |

Clinical observations, body weights, and intraocular pressure (IOP) were assessed up to 13 weeks post-dose. Plasma and ocular matrixes (aqueous humor (AH), lens, iris/ciliary body (ICB), vitreous humor (VH), sclera/choroid (SC), and retina) were sampled on Days 1, 14, 28, 56, and 91. Plasma (LLOQ 0.5 ng/mL) and ocular matrixes (LLOQ 2-15 ng/mL) were analyzed using LC-MS/MS, and resulting data were assessed for noncompartmental PK parameters.

There were no observed adverse effects related to treatment or method of administration. TA in plasma peaked on Day 1 at 4 ng/mL in both groups, and TA was quantifiable in all ocular matrixes through Day 91. Following SCS injection, $C_{max}$ and $AUC_{0-t}$ values were greatest in the sclera/choroid, followed by the retina, vitreous humor, iris, lens, aqueous humor, and plasma, in order of decreasing values. Following IVT injection, $C_{max}$ and $AUC_{0-t}$ values were greatest in the vitreous humor, followed by the iris, retina, lens, sclera/choroid, aqueous humor, and plasma, in order of decreasing values.

SCS TA $C_{max}$ and AUC (area under the concentration curve) was increased in the sclera/choroid ($C_{max}$: 10-fold, AUC: 11-fold) compared with IVT TA (Table 5). SCS and IVT TA retina $C_{max}$ and AUC were roughly equivalent (Table 5), but SCS TA peaked more quickly (Day 1) compared with IVT TA (Day 14). Exposure to TA was higher in the sclera/choroid following SCS injection compared to IVT injection. The SCS:IVT $C_{max}$ and $AUC_{0-t}$ ratios for the sclera/choroid were 12.2 and 11.7, respectively (Table 5).

IVT TA $C_{max}$ and AUC was increased in lens ($C_{max}$: 290-fold, AUC: 690-fold), aqueous Humor ($C_{max}$: 250-fold, AUC: 63-fold), Iris/ciliary body ($C_{max}$: 24-fold, AUC: 44-fold) and VH ($C_{max}$: 4-fold, AUC: 52-fold) compared with SCS TA (Table 5).

The data suggested that both IVT and SCS TA were well tolerated in the albino rabbit and systemic exposure was minimal by either route (FIG. 29). In addition, SCS TA is absorbed at much greater proportions into the clear/choroid and retina, while IVT TA distributes throughout the eye, indicating that SCS administration using a microneedle is a targeted approach for delivering TA to therapeutically-relevant ocular structures of posterior segment disease and limiting anterior segment exposure.

Example 11. Evaluation of Suprachoroidal Microinjection of Triamcinolone Acetonide in a Model of Posterior Uveitis in New Zealand White Rabbits In this study, the effects of pretreatment with suprachoroidal or intravitreal triamcinolone acetonide (TA) in a subretinal endotoxin-induced model of posterior segment uveitis in New Zealand White rabbits was evaluated.

On Day 1, female rabbits (4 eyes/group) received a single unilateral injection of vehicle or 4 mg TA (Triesence®, 40 mg/mL suspension, Alcon Labs) into the suprachoroidal space (SCS) using a 33 g 750 μm microneedle, or a 4 mg TA IVT injection using a standard 30 g needle. On Day 6, each animal received a single unilateral subretinal injection of lipopolysaccharide (LPS, 20-30 μL, 203 μg/g of 1% sodium hylauronate) to induce ocular inflammation in the treated eye. Animals were monitored for 22 days following dose administration. Endpoints included body weights, ocular observations, slit lamp biomicroscopy with McDonald-Shadduck scoring and photography, indirect ophthalmoscopy, fundus photography, intraocular pressure (IOP), and histopathology. A summary of the study design is shown below, in Table 6.

TABLE 5

Pharmacokinetics of IVT vs. SCS treatment.

| Matrix | Treatment | $C_{max}$ (ng/mL) | $T_{max}$ (day) | $C_{last}$ (ng/mL) | $T_{last}$ (day) | $AUC_{0-t}$ (ng · day/mL) | $AUC_{0-\infty}$ (ng · day/mL) | $T_{1/2}$ (day) | SCS: IVT $C_{max}$ | SCS: IVT $AUC_{0-t}$ |
|---|---|---|---|---|---|---|---|---|---|---|
| Aqueous Humor | SCS | 16 | 28 | 16 | 28 | NA[a] | NA | NC | 0.06 | NA[a] |
|  | IVT | 269 | 14 | 42 | 91 | 8,500 | NA | NC |  |  |
| Iris/Ciliary body | SCS | 50,200 | 1 | 247 | 91 | 1,190,000 | 1,190,000 | 9 | 0.04 | 0.03 |
|  | IVT | 1,260,000 | 1 | 463,000 | 91 | 40,900,000 | NA | NC |  |  |
| Lens | SCS | 1,870 | 1 | 9 | 91 | 27,400 | NA | NC | 0.00 | 0.00 |
|  | IVT | 540,000 | 14 | 40,300 | 91 | 12,600,000 | NA | NC |  |  |
| Vitreous Humor | SCS | 287,000 | 1 | 10 | 91 | 3,460,000 | NA | NC | 0.18 | 0.04 |
|  | IVT | 1,640,000 | 1 | 218,000 | 91 | 77,600,000 | 85,500,000 | 25 |  |  |
| Retina | SCS | 907,000 | 1 | 2,600 | 91 | 24,600,000 | NA | NC | 1.16 | 0.98 |
|  | IVT | 781,000 | 14 | 41,500 | 91 | 25,100,000 | 26,300,000 | 21 |  |  |
| Sclera/choroid | SCS | 2,860,000 | 1 | 34,000 | 91 | 101,000,000 | 101,000,000 | 11 | 12.20 | 11.70 |
|  | IVT | 235,000 | 14 | 27,100 | 91 | 8,640,000 | 10,300,000 | 43 |  |  |

[a] $AUC_{0-t}$ could not be calculated for aqueous humor following SCS injection since there were not at least three measureable concentration values.

TABLE 6

Study design

| Group | # of eyes | Ocular Injections (OD) | | | | Schedule | |
|---|---|---|---|---|---|---|---|
| | | Formulation | Route | Dose Volume | Day of Dosing | Subretinal LPS injection | Euthanasia |
| A | 4 | Vehicle | SCS | 100 μL | Day 1 | Day 6 | Day 22 |
| B | 4 | TA | SCS | 100 μL | Day 1 | Day 6 | Day 22 |
| C | 4 | TA | IVT | 100 μL | Day 1 | Day 6 | Day 22 |

TABLE 6-continued

Study design

| Group | Toxin | Toxin location | Treatment | Treatment location |
|---|---|---|---|---|
| A | LPS | Sub-retinal | Vehicle | suprachoroidal |
| B | LPS | Sub-retinal | TA 4 mg | suprachoroidal |
| C | LPS | Sub-retinal | TA 4 mg | intravitreal |

There were no test article- or administration-related effects on mortality, body weights, or ocular observations. Additionally, no significant increase in IOP was observed after SCS TA administration (FIG. 21D). Thirteen days following LPS injection, eyes that were administered the SCS vehicle displayed greater panuveitis than SCS TA or IVT TA eyes (FIG. 21A). SCS administration of TA caused a reduction in the overall inflammatory response as compared to control (FIG. 21A). Vitritis, aqueous flare, and cellularity were substantially less severe in both SCS and IVT TA groups of eyes compared to SCS vehicle eyes (FIG. 21B). Iris vessel dilation and tortuosity was reduced in SCS TA animals and reduced to a lesser extent in IVT TA animals when compared with the SCS vehicle group. SCS TA caused a significant reduction in inflammatory endpoints when compared with the vehicle group throughout the study. There was a marked reduction in inflammation as assessed histopathologically in eyes administered either SCS or IVT TA when compared with the vehicle group (FIG. 21C).

The results of the study showed that SCS administration of 4 mg TA using a hollow microneedle was as effective as 4 mg IVT TA in reducing the inflammatory response in this subretinal endotoxin-induced model of posterior uveitis in the albino rabbit.

Example 12. Treatment of Acute Posterior Uveitis in a Porcine Model by Injection of Triamcinolone Acetonide into the Suprachoroidal Space Using Microneedles Versus Triamcinolone Acetonide Intravitreal Injection In this study, the effects of microneedle injection of triamcinolone acetonide (TA) into the suprachoroidal space (SCS) were compared to the effects of intravitreal (IVT) TA injection in a model of acute posterior uveitis.

Ten weanling pigs had IVT injection with BSS or lipopolysaccharide (LPS) followed 24 hours later with an injection of 0.2 mg or 2.0 mg of TA into the SCS or by IVT. The SCS was accessed using hollow microneedles provided herein. A measurement of each eye under the Hackett/McDonald scoring system was performed on −1, 0, and 3 days after treatment. Pigs were then euthanized, aqueous and vitreous humor collected for cell counts and protein levels, and the eyes were processed for histopathology.

Injection of TA to the SCS using microneedles was associated with a significant reduction in inflammatory response in the pigs treated. (FIG. 22A). Furthermore, this reduction in inflammatory response can be achieved at lower doses when TA is delivered to the SCS than when TA is delivered intravitreally. FIG. 22B shows that a reduction in inflammation was observed with in 3 days with a dose of TA administered to the SCS that was ten percent of the dose of TA required when administered intravitreally.

Results from this study suggest that delivery of TA to the SCS provides effective control of inflammation, and may do so at a significantly lower dose than TA delivered intravitreally.

Example 13. Treatment of Acute Posterior Uveitis in a Porcine Model by Injection of Triamcinolone Acetonide into the Suprachoroidal Space Using Microneedles Use of animals in this study adhered to the ARVO Statement for the Use of Animals in Ophthalmic and Visual Research and was approved and monitored by the North Carolina State University Institutional Animal Care and Use Committee. Animals were acclimated to the study environment for 1 week prior to uveitis induction.

A total of 20 domestic weanling pigs (*Sus scrofa domesticus*), male or female, (12-20 kg) were used in this study. Only the left eye was tested in this study; the right eye was not injected, examined, or treated. All injections were performed with the pigs anesthetized (intramuscular Telazol-Ketamine-Xylazine and isoflorane in oxygen via mask) and the eye prepared aseptically (sterile 5% betadine solution followed by irrigation with sterile eyewash). Immediately following the injections, 1 drop of moxifloxacin ophthalmic solution (Vigamox®, Alcon Laboratories, Fort Worth, Tex.) was applied topically.

Twenty-four hours prior to SCS or IVT injection of TA or vehicle (Day −1), 100 ng of lipopolysaccharide (LPS; *E. coli* 055:B55; Sigma, Inc. St. Louis, Mo.) in 100 µL BSS (Balanced Salt Solution, Alcon Laboratories, Inc., Fort Worth, Tex.), was injected using a 27 gauge needle into the posterior central vitreous.

Twenty-four hours after the LPS injection (Day 0), 0.2 mg or 2.0 mg of commercially-available TA (Triesence®; Alcon Laboratories, Inc, Fort Worth, Tex.) or vehicle was injected either intravitreally (27 gauge needle) or into the SCS (33 gauge, 850 µm microneedle) in eyes prepared aseptically (Table 7). The dose of TA was selected to represent a typical therapeutic dose (e.g., 2.0 mg) and a dose 10 times less to compare therapeutic effect.

All injections were made superiorly, approximately 5-6 mm posterior to the limbus. To help stabilize the eye for SCS injection, a sterile laboratory spatula (Corning sterile flat end spatula, Corning Life Sciences, Corning, N.Y.) was placed in the inferior conjunctival fornix. To become proficient at the SCS injection technique with microneedles, approximately 10-15 SCS injections were made in cadaver porcine eyes prior to conducting this study. TA was diluted using vehicle to provide a low dose (0.2 mg/100 µL) or high dose (2.0 mg/100 µL). The vehicle (100 uL) was also used in the control groups, but without TA. Treatment groups are listed in Table 7.

TABLE 7

Treatment groups and study design

| Group | Treatment 100 μL (Day −1/Day 0) | Number of animals | Examinations |
|---|---|---|---|
| 1 | BSS IVT/Vehicle SCS | 2 | Ocular inflammatory scores: |
| 2 | 100 ng LPS IVT/Vehicle SCS | 2 | Days −1, 0, 1, 2, & 3 |
| 3 | 100 ng LPS IVT/0.2 mg TA SCS | 4 | IOP: |
| 4 | 100 ng LPS IVT/2.0 mg TA SCS | 4 | Days −6, −4, −1, 0, 1, 2, & 3* |
| 5 | 100 ng LPS IVT/0.2 mg TA IVT | 4 | ERG, OCT, Photo: |
| 6 | 100 ng LPS IVT/2.0 mg TA IVT | 4 | Days −1, 0, & 3 |

Days of the Week/Study Time (Hours)

| M | T | W | R | F | S | S | M | T | W | R | F |
|---|---|---|---|---|---|---|---|---|---|---|---|
| −192 | −168 | −144 | −120 | −96 | −72 | −48 | −24 | 0 | 24 | 48 | 72 |
| ↑ Start acclimation | | IOP | | IOP | | | GA LPS | GA TA | IOP Exam | IOP Exam | IOP Exam GA Euthanasia |

BSS—balanced salt solution;
IVT—intravitreal;
SCS—suprachoroidal space;
LPS—lipopolysaccharide;
TA—triamcinolone acetanide;
ERG—electroretinography;
OCT—optical coherence tomography;
Photo: ocular fundus photography.
*plus 1, 3, and 6 hours after treatment injections Ocular Inflammatory Scores A Hackett-McDonald microscopic ocular inflammatory scoring system, modified for use in pigs (instead of New Zealand White rabbits) as described below, was used to evaluate the ocular anterior segment and anterior vitreous. Scores of the conjunctiva (congestion, swelling, discharge, 0-4); aqueous flare (0-3); pupillary light reflex (0-2); iris involvement (0-4); cornea (involvement and area, 0-4); pannus (vascularization, 0-2); and anterior vitreal cellular infiltrate (0-4) were summed to provide a single inflammatory score for each animal for each examination. Using a portable slit lamp biomicroscope (Zeiss HSO-10, Carl Zeiss Meditec, Inc. USA), ocular inflammatory scores were evaluated at Day −1 (prior to LPS injection), at Day 0 (prior to vehicle or TA injection), then at 1, 2 and 3 days after injection.

Intraocular Pressure

Intraocular pressure (TOP) was measured at −6, −4, −1, 0, 1, 2, and 3 days using a TonoVet Tonometer (iCare, Finland). In addition, IOP was measured 1, 3, and 6 hours after SCS or IVT injections on Day 0. The measurements were collected without use of topical anesthetic, per manufacturer recommendation. Conditioning of the pigs during acclimation permitted routine ocular examinations and IOP measurements to be done with minimal manual restraint. The tip of the tonometer probe was directed to contact the central cornea and 6 measurements were made consecutively. After the six measurements, the mean IOP was shown on the display providing the IOP that was recorded.

Electroretinography (ERG)

With the pigs anesthetized on Days −1, 0 and 3, and pupils dilated with 1% tropicamide HCL and corneas anesthetized with 0.5% proparacaine HCl, whole field ERGs were recorded from the left eye prior to injections. All animals were dark adapted for 15 minutes prior to ERG. A monopolar contact lens electrode (ERG-jet, La Chaux des Fonds, Switzerland) was placed on the cornea to serve as an active electrode. A subdermal electrode at the lateral canthus served as the indifferent electrode. A Barraquer eyelid speculum was placed to maintain open eyelids and a subdermal needle electrode was inserted dorsally as the ground electrode. ERGs were elicited by brief flashes at 0.33 Hz delivered with a mini-ganzfeld photostimulator (Roland Instruments, Wiesbaden, Germany) at maximal intensity. Twenty responses were amplified, filtered, and averaged (Retiport Electrophysiologic Diagnostic Systems, Roland Instruments, Wiesbaden, Germany). B wave amplitudes were recorded from each pig at the designated times.

Wide-Field Ocular Fundus Digital Photography

On study days −1, 0 and 3, with the animals anesthetized and pupils dilated with tropicamide 1%, the ocular fundus was photographed using standardized illumination and focus by a wide-field digital imaging system (Retcam II, Clarity Medical Systems, Pleasanton, Calif.).

Optical Coherence Tomography

Following wide-field ocular fundus photography on Days −1, 0, and 3, the central retina was imaged with spectral-domain optical coherence tomography (SD-OCT) (Bioptigen SDOCT EnVisu Ophthalmic Imaging System, Durham, N.C.) using 6 imaging protocols (including rectangular volume scans of 6, 8, and 12 mm, and doppler rectangular volume). The SD-OCT allowed in vivo assessment of retinal pathology and retinal thickness was measured, using internal calipers, of three representative areas one disc diameter superior to the optic disc then averaged to provide a mean value retinal thickness per eye per time period.

Ocular Histopathology

Pigs were euthanized on study day 3 after clinical scoring, OCT, ERG, and wide-field ocular fundus photography was completed. After euthanasia with an overdose of intravenous barbiturate, both eyes were removed. Aqueous humor (AH) was aspirated and a 1 mL sample of vitreous humor (VH) was collected from each eye immediately after euthanasia. The globe was then fixed in Davidson's solution for 24 hours, followed by alcohol. Central, saggital sections of each globe, including the optic nerve, were stained with hematoxylin and eosin and examined by light microscopy. Two pathology-trained observers, masked to the study groups, graded degree of inflammatory infiltrate of the ocular anterior and posterior segments. The grading scale for the anterior and posterior ocular segment used was as follows: 0=no evidence of cellular infiltrate; 1=a few cells infiltrated (mild)—focal; 2=a few cells infiltrated (mild)—diffuse; 3=moderate number of cells infiltrated; and 4=high amount of cellular infiltrate.

Aqueous and Vitreous Humor Inflammatory Cell Counts and Protein Concentration

After aspiration from the eyes, AH and VH were immediately placed on ice, transferred to the laboratory, then frozen at −80° C. until processing. Samples where thawed at room temperature, vortexed, and total cell counts were performed with a hemocytometer. Total protein concentration was measured using the Bradford Assay (Pierce BCA Protein Assay Kit, Thermo Scientific Pierce, Rockford, Ill.).

Data and Statistical Analysis

For histologic grading, two independent observers masked to the treatment group evaluated each eye at each time point and the average resulting scores for each animal were used for analysis. Parametric normally distributed data (i.e., IOP, ERG, retinal thickness, cell counts, protein concentration) were compared by time point for each group using 1-way ANOVA models with Tukey-Kramer post-hoc analysis. For non-parametric data (i.e., clinical scores, histologic grades), Wilcoxon tests were conducted per animal by time point. Differences were considered significant at P<0.05. Results and probabilities were calculated using computerized statistical software (JMP 10, SAS Inc. Cary, N.C.).

Results

Injections of TA or vehicle into the SCS were accomplished using microneedles without difficulty or adverse effect. Eyes were examined via slit lamp biomicroscopy and indirect ophthalmoscopy following each injection. No evidence of back-leakage of treatment materials through the microneedle scleral perforation or leakage of the white drug suspension into the vitreous was observed following SCS injection. Intravitreal TA injections were visible as central vitreal white depots on indirect ophthalmoscopy. Furthermore, there was no evidence of injection site or vitreal hemorrhage following any injections (SCS or IVT).

Ocular Inflammatory Scores

Following intravitreal injection of LPS on Day −1, cumulative inflammatory scores elevated to between 6 and 10 in all groups (FIG. 23). Scores in eyes injected with LPS were significantly higher than in eyes injected with BSS (P<0.02). Following treatment injections on Day 0, inflammatory scores generally decreased, although 24 hours after treatment, eyes treated with vehicle (Group 2) had mean scores significantly higher than the other treatment groups (P<0.02) and eyes treated with IVT 0.2 mg TA (Group 5) had mean scores that were significantly higher (P<0.03) than Groups 1, 3, 4 and 6. At 48 and 72 hours after treatment, eyes treated with 0.2 mg IVT TA (Group 4) had significantly higher mean scores than eyes treated with SCS TA (0.2 and 2.0 mg; Groups 3 and 4) and vehicle (Group 1). Eyes treated with SCS TA (0.2 and 2.0 mg; Groups 3 and 4) and IVT TA (2.0 mg; Group 6) had mean inflammatory scores not significantly different than eyes treated with vehicle at each examination day (i.e., Days 1, 2, and 3) after treatment (FIG. 23).

Intraocular Pressure

Intraocular pressure ranged from 19 to 24 mmHg during acclimation and decreased slightly over time as pigs became accustomed to being handled. On induction of uveitis, the IOP decreased by time 0 to between 12 and 16 mmHg in groups receiving LPS. Following treatment injections, TOP remained low in all groups through 6 hours post injection, then returned to baseline. Group 1 eyes, which did not receive LPS, had significantly higher TOP 1 and 3 hours after treatment injections than Group 2 eyes (P=0.01; 0.04). Otherwise, there were no significant differences between the groups (FIG. 24) and there were no acute elevations in TOP noted immediately (i.e., 1, 3, 6 hours) after injections.

Electroretinography

Scotopic B wave amplitudes were not significantly different between any of the groups evaluated at each time point (i.e., Days −1, 0, and 3), except for Group 4 at Day −1, which was significantly higher than Groups 1, 3, 5, and 6 (P<0.007). This pretreatment result was likely a result of biologic variation and is not clinically significant. However, no evidence of retinal dysfunction (i.e., decrease in b wave amplitude) was noted after injections.

Wide-Field Ocular Fundus Digital Photography

Wide-field ocular fundus images revealed substantial cloudiness of the ocular posterior segment 24 hours after LPS injection, except in Group 1, which was injected with BSS and remained normal in appearance. The cloudiness observed in the LPS injected eyes was a result of exudative and cellular infiltrate into the vitreous humor. In vehicle treated eyes (Group 2), the cloudiness appeared to increase from Days 1 to 3 post-injection. Treatment with 0.2 and 2.0 mg TA into the SCS and 2.0 mg TA IVT resulted in ocular fundus images with less vitreal cloudiness and similar to the pre-treatment fundus appearance. However, treatment with 0.2 mg TA IVT resulted in images only slightly improved over vehicle treated eyes. Eyes with 2.0 mg TA IVT injections had a solid large depot of TA visible in the central vitreous (FIGS. 25A-B).

Optical Coherence Tomography

There was no significant difference in retinal thickness in any of the groups prior to or following the injections. Overt retinal pathology was not observed after the induction of uveitis or treatments, however, cells were observed emanating from retinal vasculature.

Ocular Histopathology

None of the eyes examined in any group had evidence of substantial tissue structural or toxicologic changes on histopathology. However, all eyes, except Group 1 (BSS intravitreal/vehicle SCS), had cellular infiltrate in the anterior uvea, vitreous, and retina. The cellular infiltrate was predominantly neutrophils. Group 2 eyes (LPS intravitreal/vehicle SCS) had moderate to severe neutrophilic infiltrate in the iris, iris root and iridocorneal angles. Additionally, there was moderate to severe neutrophilic infiltrate in the vitreous body, inner retinal layers, and retinal perivascular cuffing of inflammatory cells (FIG. 26). In Group 3 eyes (LPS intravitreal/low dose TA SCS), there was mild neutrophilic infiltrate in the iris, and moderate infiltrate of neutrophils in the inner retinal layers and vitreous. The anterior segment of Group 4 eyes (LPS intravitreal/high dose TA SCS) was normal, with only an occasionally observed inflammation cell. The vitreous had very mild neutrophilic infiltration and very mild inner retinal cellular infiltrate. TA was visible in the SCS space on each eye in Group 4 (FIG. 26) indicating that the injection technique indeed delivered TA to the SCS. There was no inflammation or histologic evidence of toxicity in the SCS as a result of the TA or injection. In Group 5 eyes (LPS intravitreal/low dose TA IVT), there was mild neutrophilic infiltrate in the anterior uvea and moderate to severe cellular infiltrate in the vitreous and moderate infiltrate in the inner retina including moderate perivascular infiltrate. In Group 6 eyes (LPS intravitreal/high dose TA SCS), there was mild neutrophilic infiltrate in the anterior uvea, and moderate vitreal infiltrates, including mild perivascular infiltrate (FIG. 26).

Review of ocular histopathologic inflammatory scores (FIG. 27) of the anterior and posterior segment revealed that Group 1 eyes (BSS intravitreal/vehicle SCS) had mean histologic inflammatory scores that were significantly lower than the other groups (P<0.04). Eyes in Group 5 (LPS intravitreal/low dose TA IVT) had mean histologic inflammatory scores in the anterior segment that were significantly higher than eyes receiving high dose TA either in the SCS (Group 4) or intravitreally (Group 6) (P<0.04). Eyes of Group 4 (LPS intravitreal/high dose TA SCS) had mean histologic inflammatory scores in the ocular posterior segment that were significantly lower than vehicle treated eyes (Group 2) and eyes treated with IVT TA (Groups 5 and 6) (P<0.04). Eyes treated with high dose IVT TA had mean histologic inflammatory scores that were significantly lower than vehicle treated eyes (Group 2) (P=0.018) (FIG. 27).

Aqueous and Vitreous Humor Inflammatory Cell Counts and Protein Concentration

Mean aqueous humor (AH) cell counts ranged from 2,000 cells/ml in Group 1 (BSS intravitreal/vehicle SCS) eyes to 27,800±SD 530 cells/ml in Group 2 (LPS intravitreal/vehicle SCS) eyes, which were significantly higher than each other group (P<0.0023). Mean AH cell counts of Groups 5 (LPS intravitreal/low dose TA IVT) and 6 (LPS intravitreal/high dose TA IVT) were significantly higher than Group 1 (BSS intravitreal/vehicle SCS) (P=0.022; P=0.021). Mean AH cell counts of Groups 3 (LPS intravitreal/low dose TA SCS) and 4 (LPS intravitreal/high dose TA SCS) were not significantly different than AH cell counts of Group 1 (BSS intravitreal/vehicle SCS), Group 5 (LPS intravitreal/low dose TA IVT), or 6 (LPS intravitreal/high dose TA IVT) (FIG. 28).

Mean vitreous humor (VH) cell counts ranged from 6,300 cells/ml in Group 1 (BSS intravitreal/vehicle SCS) eyes to 55,000±SD 1,620 cells/ml in Group 2 (LPS intravitreal/vehicle SCS) eyes, which was significantly higher than each other group (P<0.018). Mean VH cell count of Group 3 (LPS intravitreal/low dose TA SCS) was significantly higher than Group 1 (BSS intravitreal/vehicle SCS) (P=0.031) and Group 4 (LPS intravitreal/high dose TA SCS) (P=0.048). Mean VH cell count of Group 5 (LPS intravitreal/low dose TA IVT) also was significantly higher than VH cell counts in Group 1 (BSS intravitreal/vehicle SCS) (P=0.023) and Group 4 (LPS intravitreal/high dose TA SCS) (P=0.032). Mean VH cell count of Group 3 (LPS intravitreal/low dose TA SCS) was not significantly different than VH cell counts in Groups 5 (LPS intravitreal/low dose TA IVT) and 6 (LPS intravitreal/high dose TA IVT). Furthermore, mean VH cell counts of Group 4 (LPS intravitreal/high dose TA SCS) were not significantly different than the VH cell counts of Group 1, the untreated control (FIG. 28).

Mean aqueous humor (AH) protein concentration ranged from 0.0 mg/ml in Group 1 (BSS intravitreal/vehicle SCS) eyes to 3.0±SD 3.5 mg/ml in Group 6 eyes. There were no significant differences in mean aqueous humor protein concentration among the groups. Mean vitreous humor (VH) protein concentration ranged from 0.0 mg/ml in Group 1 (BSS intravitreal/vehicle SCS) eyes to 4.0±SD 0.8 mg/ml in Group 6 (LPS intravitreal/high dose TA IVT) eyes. Group 1 (BSS intravitreal/vehicle SCS) and Group 4 (LPS intravitreal/high dose TA SCS) had significantly lower mean vitreous humor protein concentrations than Groups 3 (LPS intravitreal/low dose TA SCS), 5 (LPS intravitreal/low dose TA IVT), and 6 (LPS intravitreal/high dose TA IVT) (P<0.033).

These data show that delivery of TA to the SCS using microneedles was effective and tolerated with an acceptable safety profile for up to three days after injection in porcine eyes. Furthermore, SCS injection of 0.2 mg and 2.0 mg of TA was as effective in reducing inflammation in this model as 2.0 mg TA IVT injection. Mean inflammatory scores, vitreal cellular infiltrate OCT scores, and histologic grades of eyes receiving 0.2 mg and 2.0 mg of TA in the SCS were not significantly different from 2.0 TA injected IVT. There was evidence that 0.2 mg TA injected in the SCS was as effective in reducing acute ocular inflammation as was 2.0 mg TA IVT, while 0.2 mg TA IVT was less effective. A 10-fold decrease in effective dose when the drug is delivered to the SCS may have occurred because of more targeted delivery of the TA to the choroid and retina.

There was no evidence of injection site complications, acute elevated intraocular pressure, or retinal toxicity after SCS injections. Acutely elevated TOP was not observed in this study after SCS injections.

Delivery of TA to the SCS provides effective therapy to reduce acute posterior uveitis in a model that is similar in anatomy, size, and retinal vascular pattern to the human eye. There were no adverse effects, increased TOP, or evidence of procedural or acute drug toxicity following injection of TA into the SCS in porcine eyes.

Example 14. Suprachoroidal Microinjection of Bevacizumab is Well Tolerated in Human Patients The safety and tolerabilty of a single microneedle injection of bevacizumab into the suprachoroidal space (SCS) using a microneoeedle was evaluated. Four adult patients with choroidal neovascularization (CNV), secondary to wet age-related macular degeneration (AMD), were enrolled in a phase 1, single-center, open-label study. Each subject provided informed consent and was screened for eligibility. Following application of topical anesthesia, each patient was administered a single unilateral injection of 100 µL bevacizumab (Avastin®) into the SCS using an 850 µm 33 gauge microneedle. The microneedle was inserted into the sclera approximately 8-12 mm posterior to the limbus in the superior temporal quadrant. Treated patients remained in the clinic for 4 hours for observation and then returned multiple times for follow-up during a 2 month period. Major safety examinations included intraocular pressure (TOP), angiograms, biomicroscopy, indirect ophthalmoscopy, fundus photography, optical coherence tomography (OCT), visual acuity (VA) (Table 8), and assessment of pain.

Four patients were successfully dosed into the SCS which was confirmed via ophthalmoscope immediately following injection. A moderate level of pain was recorded for the administration. There were no unexpected or serious adverse events related to bevacizumab or the method of administration on ophthalmic examinations. No negative effect on IOP, OCT (FIG. 30) or VA was noted in any subject. No patients required rescue therapy or reinjection during the two months following treatment. The results of the study showed that the SCS can be successfully and safely dosed via the microneedle using only topical anethesia. The results of the study also demonstrate that 100 µL of bevacizumab can be delivered into the SCS without unexpected or serious adverse events.

TABLE 8

Visual Acuity of Patients.

| Patient | Screening | Pre-does | 28 day post dose | 56 day post dose |
|---|---|---|---|---|
| 1 | 20/40 | 20/80 | 20/40 | 20/40 |
| 2 | 20/40 | 20/40 | 20/20 | 20/20 |
| 3 | 20/320 | 20/320 | 20/250 | 20/250 |
| 4 | 20/400 | 20/400 | 20/400 | 20/400 |

Example 15. Comparison of the Total Amount of Triamcinolone Acetonide Delivered Via Suprachoroidal or Intravitreal Administration In this study, the total amount of triamcinolone acetonide (TA) delivered into a pig eye when injected into the suprachoroidal space using a hollow microneedle or into the vitreous using a standard 30 gauge needle was compared. Whole pig cadaver eyes (Sioux-Preme Packing) enucleated within 24 hours after death were used for all injections. Intravitreal and suprachoroidal injections of TA were performed using Triesence® (TA; Alcon Labs). Intravitreal injections were performed using a 30 g needle (Becton-Dickinson) and suprachoroidal injections were performed using a hollow microneedle. 1 mL syringes (Becton-Dickinson) were loaded with the required amount of TA at each of the three volumes assessed: 50, 100, and 150 μL (2, 4, and 6 mg, respectively). The residual amount of TA present in the syringe/needle assembly after injection was determined by RP-HPLC. The total amount of TA delivered to the eye for each dose volume was determined as the difference in the total amount loaded into a syringe before injection into the pig eye versus the residual amount of TA recovered from the syringe/needle assembly after injection.

Average total dose administered following 50, 100 and 150 μL TA injected into the suprachoroidal space ranged from 86-92% of the target dose level, while average total dose administered following 50 and 100 μL TA injected into the vitreous ranged from 88-89%. Virtually no difference was observed between the two routes of administration and needles for each volume. The results of the study showed that the target dose level of TA can be consistently delivered into the SCS using a microneedle or into the vitreous using a 30 g needle. Total amount of TA delivered was similar between the two administration routes.

Example 16. Suprachoroidal Microinjection of 4 mg Triamcinolone Acetonide in the New Zealand White Rabbit In this study, the ocular tolerability and toxicokinetics of suprachoroidal administration of 4 mg triamcinolone acetonide (TA) using a microneedle was determined, in the New Zealand White rabbit as an animal model.

On Day 0, New Zealand White (NZW) rabbits (4/sex/group/terminal time point, 48 total) were administered a single bilateral suprachoroidal injection of 100 μL of 4 mg TA (40 mg/mL) or vehicle, using a 33 g 750 μm microneedle. Clinical observations, body weights, food consumption, slit lamp biomicroscopy with McDonald-Shadduck scoring, indirect ophthalmoscopy, intraocular pressure assessment (IOP), central corneal thickness (CCT), electroretinography (ERG), serum chemistry and hematology, and systemic exposure were assessed up to 13 weeks postdose. Animals were sacrificed on Day 1 or Week 13 and were evaluated for macroscopic observations at necropsy and ocular histopathology. Four animals/sex were given an additional suprachoroidal administration on Day 90, and will be followed for an additional 13 weeks.

TA injection into the suprachoroidal space using the microneedle was performed successfully in 96 eyes. There were no administration- or TA-related adverse effects on clinical observations, body weight, body weight gain, food consumption, or serum chemistry and hematology.

Findings observed during slit lamp biomicroscopy and fundus examination were generally mild and transient in nature, and demonstrated excellent ocular tolerability for up to 13 weeks following suprachoroidal administration (Table 9).

TABLE 9

Ophthalmic Examinations

| | Vehicle | | 40 mg/mL TA | |
|---|---|---|---|---|
| | Number of Animals | | | |
| Treatment | M: 12 | F: 12 | M: 12 | F: 12 |
| Conjunctival Congestion (Slight, Transient) | — | 1 | — | 2 |
| Conjunctival Discharge (Slight, Transient) | — | — | — | 2 |
| Corneal Staining (Slight, Transient) | 2 | 1 | 1 | 1 |
| Corneal Scratch (Trace, Transient) | 1 | 1 | 1 | — |
| Fibrin in Vitreous (Transient) | — | 1 | 1 | — |
| Retina, Abnormal Area (Small, Transient) | — | 1 | — | — |

A decrease in intraocular pressure (IOP) related to the injection procedure was observed in both groups at 24 hours following suprachoroidal administration (FIG. 31). This has also been observed in studies employing intravitreal injection. A mild increase in TOP of approximately 2-3 mmHg was observed in the 4 mg TA group when compared with the vehicle group on Days 7-90, but was not considered adverse due to the small magnitude of change (FIG. 31). A decrease in TOP was observed in the vehicle group on Day 28, and was investigated, but no contributing factors to this unexpected dataset were uncovered.

On Day 1, a slight decrease in central corneal thickness (CCT), as measured by pachymetery, was observed in both groups, which resolved by Day 90. There was no significant difference in CCT between treatments (FIG. 32).

There was no administration- or 4 mg TA-related effect on a-wave or b-wave implicit time or amplitude, as assessed by scototopic electroretinography (ERG) (Table 10).

TABLE 10

Electroretinography

| | | | Scotopic | | | |
|---|---|---|---|---|---|---|
| | Time | | a-wave | | b-wave | |
| Treatment | Point | Protocol | Mean | SD | Mean | SD |
| Vehicle | Baseline | Time (ms) | 12.7 | 0.9 | 39.3 | 7 |
| | | Amplitude (μV) | 116.1 | 22 | 256.6 | 69 |
| | Day 1 | Time (ms) | 12.9 | 0.9 | 52.5 | 1.3 |
| | | Amplitude (μV) | −121.5 | 20.3 | 244.5 | 50.6 |
| | Day 90 | Time (ms) | 12.6 | 0.7 | 51.6 | 1 |
| | | Amplitude (μV) | −115.9 | 19.9 | 290.4 | 53.7 |
| Triamcinolone | Baseline | Time (ms) | 12.5 | 0.06 | 43.4 | 8.6 |
| | | Amplitude (μV) | −131.6 | 28.2 | 257.3 | 33.6 |

TABLE 10-continued

Electroretinography

| | | | Scotopic | | | |
| | | | a-wave | | b-wave | |
| Treatment | Time Point | Protocol | Mean | SD | Mean | SD |
|---|---|---|---|---|---|---|
| | Day 1 | Time (ms) | 12.5 | 0.6 | 51.8 | 1.7 |
| | | Amplitude (μV) | −123.15 | 21.3 | 239.8 | 38.6 |
| | Day 90 | Time (ms) | 12.8 | 0.7 | 52.4 | 1.2 |
| | | Amplitude (μV) | −145.8 | 31.5 | 338.1 | 56.1 |

FIG. 33 shows the mean TA concentration in plasma, ±SD, as measured in 8 rabbits. Systemic exposure to TA following suprachoroidal administration was minimal with a mean $C_{max}$ of 12 ng/mL on Day 1.

Histopathologically, TA was easily visualized within the suprachoroidal space on Day 1, and vehicle was not discernible. There were no adverse effects related to the method of administration or 4 mg TA as assessed by histopathology (Table 11).

TABLE 11

Histopathological assessments

| | Vehicle | | 40 mg/mL TA | |
| | Number of Animals | | | |
| Treatment | M: 4 | F: 4 | M: 4 | F: 4 |
|---|---|---|---|---|
| Conjunctival Extravasated Lymphocytes | — | 3 | 2 | 3 |
| Conjunctival Epithelial Thinning | — | 1 | 1 | 3 |
| Ciliary Process Edema | 2 | 1 | 1 | 2 |
| Inflammatory Cells in Stroma Limbus | — | 1 | — | 1 |
| TA in SCS | — | — | 4 | 4 |
| Small Area of Retinal Damage (Mild) | — | — | — | 1 |

These data provide further evidence that administration into the suprachoroidal space using a microneedle may be a safe, non-surgical option for ocular drug delivery of drug formulation, e.g., triamcinolone. A single bilateral suprachoroidal injection of 4 mg TA (40 mg/mL) using a 33 g 750 μm microneedle was well tolerated in the albino rabbit and resulted in limited systemic exposure to TA.

Publications, patents and patent applications cited herein are specifically incorporated by reference in their entireties. While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

The invention claimed is:

1. A method of treating macular edema in a human subject in need thereof, the method comprising, non-surgically administering an effective amount of a drug formulation comprising an anti-inflammatory drug to the suprachoroidal space (SCS) of the eye of the human subject in need of treatment of the macular edema; and further comprising non-surgically administering a second drug to the eye of the subject, wherein the second drug comprises a vascular endothelial growth factor (VEGF) antagonist.

2. The method of claim 1, wherein the macular edema is diabetic macular edema.

3. The method of claim 1, wherein the VEGF antagonist is selected from a VEGF-receptor kinase antagonist, an anti-VEGF antibody or fragment thereof, an anti-VEGF receptor antibody, an anti-VEGF aptamer, a small molecule VEGF antagonist, a thiazolidinedione, a quinoline or a designed ankyrin repeat protein (DARPin).

4. The method of claim 1, wherein the VEGF antagonist is aflibercept.

5. The method of claim 1, wherein the anti-inflammatory drug is selected from mycophenolate, infliximab, nepafenac, azathioprine, cyclophosphamide, dexamethasone, difluprednate, fluocinolone, fluorometholone, leteprednol, prednisolone acetate, prednisolone sodium phosphate, rimexolone, triamcinolone, bromfenac, diclofenac, fluibiprofen, ketorolac, adalimumab, etanercept, certolizumab, gotimumab, daclizumab, rituximab, abatacept, basiliximab, belimumab, anakinra, efaliquma, alefacept, and natalizumab.

6. The method of claim 1, wherein the anti-inflammatory drug is triamcinolone.

7. The method of claim 1, wherein the anti-inflammatory drug is triamcinolone acetonide.

8. The method of claim 1, wherein the second drug is administered to the suprachoroidal space (SCS) of the eye of the subject.

9. The method of claim 1, wherein the second drug is administered intravitreally in a second drug formulation.

10. The method of claim 1, wherein the first drug and second drug are administered to the subject in one dosing session.

11. The method of claim 1, wherein upon administration of the drug formulation to the SCS, the drug formulation flows away from the insertion site and is substantially localized to the posterior segment of the eye.

12. The method of claim 1, wherein the macular edema is macular edema secondary to retinal vein occlusion.

* * * * *